(12) United States Patent
Rubin-Bejerano et al.

(10) Patent No.: US 8,580,253 B2
(45) Date of Patent: Nov. 12, 2013

(54) IMMUNOMODULATING COMPOSITIONS AND METHODS OF USE

(75) Inventors: Ifat Rubin-Bejerano, Belmont, MA (US); Gerald R. Fink, Chestnut Hill, MA (US); Claudia Abeijon, Worcester, MA (US); Danial S. Kohane, Newton, MA (US); Jason E. Fuller, Boston, MA (US); Robert S. Langer, Newton, MA (US)

(73) Assignees: Whitehead Institute, Cambridge, MA (US); Massachusetts Institute of Technology, Cambridge, MA (US); Trustees of Boston University, Boston, MA (US); The General Hospital Corporation, Boston, MA (US)

( * ) Notice: Subject to any disclaimer, the term of this patent is extended or adjusted under 35 U.S.C. 154(b) by 423 days.

(21) Appl. No.: 12/513,830

(22) PCT Filed: Nov. 6, 2007

(86) PCT No.: PCT/US2007/023307
§ 371 (c)(1),
(2), (4) Date: Nov. 15, 2010

(87) PCT Pub. No.: WO2008/057501
PCT Pub. Date: May 15, 2008

(65) Prior Publication Data
US 2011/0045049 A1 Feb. 24, 2011

Related U.S. Application Data

(60) Provisional application No. 60/856,834, filed on Nov. 6, 2006, provisional application No. 60/880,384, filed on Jan. 16, 2007, provisional application No. 60/929,755, filed on Jul. 11, 2007.

(51) Int. Cl.
*A61K 39/395* (2006.01)
*A61K 38/00* (2006.01)

(52) U.S. Cl.
USPC .......................... 424/130.1; 514/8; 514/23

(58) Field of Classification Search
None
See application file for complete search history.

(56) References Cited

U.S. PATENT DOCUMENTS

| | | |
|---|---|---|
| 4,036,945 A | 7/1977 | Haber |
| 4,331,647 A | 5/1982 | Goldenberg |
| 4,590,181 A | 5/1986 | McCarthy |
| 4,816,567 A | 3/1989 | Cabilly et al. |
| 4,818,752 A | 4/1989 | Williams et al. |
| 4,946,778 A | 8/1990 | Ladner et al. |
| 4,992,540 A | 2/1991 | Jamas et al. |
| 5,322,841 A | 6/1994 | Jamas |
| 5,488,040 A | 1/1996 | Jamas |
| 5,504,079 A | 4/1996 | Jamas |
| 5,532,223 A | 7/1996 | Jamas |
| 5,545,806 A | 8/1996 | Lonberg et al. |
| 5,545,807 A | 8/1996 | Surani et al. |
| 5,569,825 A | 10/1996 | Lonberg et al. |
| 5,607,677 A | 3/1997 | Jamas |
| 5,622,939 A | 4/1997 | Jamas |
| 5,625,126 A | 4/1997 | Lonberg et al. |
| 5,633,369 A | 5/1997 | Jamas |
| 5,633,425 A | 5/1997 | Lonberg et al. |
| 5,661,016 A | 8/1997 | Lonberg et al. |
| 5,663,324 A | 9/1997 | Jamas |
| 5,741,495 A | 4/1998 | Jamas |
| 5,783,569 A | 7/1998 | Jamas |
| 5,811,542 A | 9/1998 | Jamas |
| 5,817,643 A | 10/1998 | Jamas |
| 5,849,720 A | 12/1998 | Jamas |
| 5,965,714 A | 10/1999 | Ryall |
| 6,046,323 A | 4/2000 | Park |
| 6,048,551 A | 4/2000 | Hilfinger et al. |
| 6,242,594 B1 | 6/2001 | Kelly |
| 6,369,216 B1 | 4/2002 | Patchen et al. |
| 6,476,003 B1 | 11/2002 | Jordan et al. |
| 6,998,115 B2 | 2/2006 | Langer et al. |
| 7,011,845 B2 | 3/2006 | Kozbor |
| 7,060,299 B2 | 6/2006 | Alavattam et al. |
| 7,566,704 B2 | 7/2009 | Patchen et al. |
| 2002/0035217 A1 | 3/2002 | Uhrich |
| 2003/0035787 A1 | 2/2003 | Uhrich |

(Continued)

FOREIGN PATENT DOCUMENTS

| | | |
|---|---|---|
| EP | 0 640 348 | 3/1995 |
| EP | 1 891 970 | 2/2008 |
| WO | WO03097091 | 11/2003 |
| WO | WO 2009/134891 | 11/2009 |

OTHER PUBLICATIONS

Niskikawa et al. Polysaccharides in lichens and fungi. III. Further investigation on the structures and the antitumor activity of the polysaccharides from *Gyrophora esculenta* miyoshi and *Lasallia papulose* Liano. Chem Pharm Bull (Tokyo) Sep. 1969, vol. 17, No. 9 pp. 1910-1916.
Shibata et al. Polysaccharides in lichens and funig. I. Antitumour active polysaccharides of *Gyrophora esculenta* Miyoshi and *Lasallia papilosa* (Ach.) Lano. hem Pharm Bull (Tokyo) Dec. 1968, vol. 16, No. 9 pp. 2362-2369.
Olafsdottir et al. Polysaccharides from lichens: structural characteristics and biological activity Planta Med. Apr. 2001, vol. 67, No. 3, pp. 199-208.
Hong et al. "Mechanism by Which Orally Administered β-1,3-Glucans Enhance the Tumoricidal Activity of Antitumor Monoclonal Antibodies in Murine Tumor Models" J Immunol 2004 173:797-806.
Li et al. "Yeast β-Glucan Amplifies Phagocyte Killing of iC3b-Opsonized Tumor Cells via Complement Receptor 3-Syk-Phosphatidylinositol 3-Kinase Pathway" *J Immunol* 2006; 177:1661-1669.

(Continued)

*Primary Examiner* — Yunsoo Kim
(74) *Attorney, Agent, or Firm* — Pearl Cohen Zedek Latzer LLP; Mark S. Cohen

(57) ABSTRACT

This invention is directed to β-1-6-glucans, compositions and devices comprising the same, and methods of use thereof in modulating immune responses. The β-1-6-glucans of certain embodiments of the invention are enriched for O-acetylated groups and/or conjugated to a solid support or linked to a targeting moiety.

45 Claims, 12 Drawing Sheets

(56) References Cited

U.S. PATENT DOCUMENTS

| | | | |
|---|---|---|---|
| 2004/0127458 | A1 | 7/2004 | Hunter et al. |
| 2005/0053577 | A1 | 3/2005 | Uhrich |
| 2005/0191361 | A1 | 9/2005 | O'Connor et al. |
| 2005/0208079 | A1* | 9/2005 | Cassone et al. ............ 424/274.1 |
| 2005/0255565 | A1 | 11/2005 | Engstad et al. |
| 2006/0009419 | A1 | 1/2006 | Ross |
| 2006/0020128 | A1 | 1/2006 | Cheung |
| 2006/0165700 | A1* | 7/2006 | Ostroff et al. ............. 424/155.1 |
| 2007/0141084 | A1 | 6/2007 | Lee et al. |
| 2008/0167268 | A1 | 7/2008 | Yan |
| 2008/0260724 | A1 | 10/2008 | Wheeler et al. |

OTHER PUBLICATIONS

U.S. Appl. No. 60/817,075, filed Jun. 29, 2006, Zumbuehl et al.
Valdivia et al. "Transglutaminase-catalyzed site-specific glycosidation of catalase with aminateddextran" Journal of Biotechnology vol. 122, Issue 3, pp. 326-333, Apr. 10, 2006.
Perez and Walker, J. Immunol. 142:32-37, (1990).
Natali et al. "Immunohistochemical Detection of Antigen in Human Primary and Metastatic Melanomas by The Monoclonal Antibody 140.240 and Its Possible Prognostic Significance." Cancer 59:55-63, (1987).
European Search Report of Application No. PCT/US2007023307 Date of Mailing Jan. 26, 2010.
International Search Report of Application No. PCT/US 07/23307 Date of Mailing May 29, 2008.
Klis et al. "Molecular organization of the cell wall of *Candida albicans*" Med Mycol. 39 Suppl 1:1-8, (2001).
Klis et al. "Dynamics of cell wall structure in *Saccharomyces cerevisiae*" FEMS Microbiology Reviews 26, p. 239-256. (2002).
Brown et al. "Immune recognition A new receptor for beta-glucans" Nature. 413(6851):36-7, Sep. 6, 2001.
Brown et al. "Fungal beta-glucans and mammalian immunity" Immunity. 19(3):311-5, Sep. 2003.
Mbadugha et al. "Sugar/Steroid/Sugar Conjugates: Sensitivity of Lipid Binding to Sugar Structure" Org. Lett., 5 (22), pp. 4041-4044, (2003).
Bystrický et al. "Conjugation of yeast mannans with protein employing cyanopyridinium agent (CDAP)—an effective route of antifungal vaccine preparation" Glycoconj J. 17(10):677-80, Oct. 2000.
Chen et al. "Nature-Inspired Creation of Protein-Polysaccharide Conjugate and Its Subsequent Assembly onto a Patterned Surface" Langmuir, 19 (22), pp. 9382-9386, (2003).
Wakshull et al. "PGG-Glucan, a soluble β-(1,3)-glucan, enhances the oxidative burst response, microbicidal activity, and activates an NF-κB-like factor in human PMN: Evidence for a glycosphingolipid β-(1,3)-glucan receptor" Immunopharmacology vol. 41, Issue 2, pp. 89-107, Feb. 1999.
Taylor et al. "The beta-glucan receptor, dectin-1, is predominantly expressed on the surface of cells of the monocyte/macophage and neutrophil lineages" *J Immunol*, 169(7):3876-82. Oct. 1, 2002.
Drouillat et al. "Novel liposaccharide conjugates for drug and peptide delivery" Journal of Pharmaceutical Sciences vol. 87, Issue 1, pp. 25-30, Jan. 1998.
Nishikawa et al. "Polysaccharides in Lichens and Fungi. III. Further Investigation on the Structures and the Antitumor Activity of the Polysaccharides from *Gyrophora esculenta* MIYOSHI and *Lasallia papulosa* LLANO" Chem. Pharm. Bull. vol. 17, No. 9, pp. 1910-1916 Sep. 1969.
Shibata et al. "Polysaccharides in Lichens and Fungi. I. Antitumour Active Polysaccharides of *Gyrophora esculenta* MIYOSHI and *Lasallia papulosa* (ACH.) LANO" Chem. Pharm. Bull. vol. 16, No. 12, pp. 2362-2369 Dec. 1968.
Olafsdottir et al. "Polysaccharides from Lichens: Structural Characteristics and Biological Activity" Planta Med; 67: 199-208, (2001).
Alban and Franz. "Partial synthetic glucan sulfates as potential new antithrombotics: A review" *Biomacromolecules*. 2(2):354-361, (2001).
Alban et al. "Synthesis of laminarin sulfates with anticoagulant activity" Arzneimittelforschung. Aug. 1992;42(8):1005-8.
Rubin-Bejerano et al. "Phagocytosis by neutrophils induces an amino acid deprivation response in *Saccharomyces cerevisiae* and *Candida albicans*" Proc Natl Acad Sci U S A. 100(19):11007-12, Sep. 16, 2003.
Wheeler and Fink. "A Drug-Sensitive Genetic Network Masks Fungi from the Immune System" PLoS Pathog; 2(4): e35, Apr. 2006.
Schlesinger et al. "Binding of the terminal mannosyl units of lipoarabinomannan from a virulent strain of *Mycobacterium tuberculosis* to human macrophages" J Immunol. 152(8):4070-9, Apr. 15, 1994.
Palma et al. "Ligands for the beta-glucan receptor, Dectin-1, assigned using "designer" microarrays of oligosaccharide probes (neoglycolipids) generated from glucan polysaccharides" J Biol Chem. 281(9):5771-9, Mar. 3, 2006.
International Search Report of Application No. PCT/US2009/042117 Date of Mailing Feb. 18, 2010.
Ukawa Y, Ito H, Hisamatsu M. "Antitumor effects of (1→3)-beta-D-glucan and (1→6)-beta-D-glucan purified from newly cultivated mushroom, Hatakeshimeji (*Lyophyllum decastes* Sing.)". J Biosci Bioeng. 2000;90(1):98-104.
Hong F, et al. "Mechanism by which orally administered beta-1,3-glucans enhance the tumoricidal activity of antitumor monoclonal antibodies in murine tumor models." J Immunol. Jul. 15, 2004;173(2):797-806.
Hong F et al., "Beta-glucan functions as an adjuvant for monoclonal antibody immunotherapy by recruiting tumoricidal granulocytes as killer cells." Cancer Res. Dec. 15, 2003;63(24):9023-31.
Li B et al. "Combined yeast {beta}-glucan and antitumor monoclonal antibody therapy requires C5a-mediated neutrophil chemotaxis via regulation of decay-accelerating factor CD55." Cancer Res. Aug. 1, 2007;67(15):7421-30.
Stephanie Dillon, et. al. "Yeast zymosan, a stimulus for TLR2 and dectin-1, induces regulatory antigen presenting cells and immunological tolerance". J Clin Invest. Apr. 2006;116(4):916-28.
Brian W. LeBlanc, et al., The effect of $PGG_{[-glucan}$ on neutrophil chemotaxis in vivo J Leukoc Biol. Apr. 2006;79(4):667-75.
Antonio García Trinidad, et al. "Coupling of C3bi to IgG inhibits the tyrosine phosphorylation signaling cascade downstream Syk and reduces cytokine induction in monocytes" J Leukoc Biol. May 2006;79(5):1073-82.
Torbjørn Breivik et al., "Soluble β-1,3/1,6-glucan from yeast inhibits experimental periodontal disease in Wistar rats." J Clin Periodontol. Apr. 2005;32(4):347-52.
Umeyama T, et al. "Deletion of the CaBIG1 Gene Reduces $_{[-1,6-}$Glucan Synthesis, Filamentation, Adhesion, and Virulence in *Candida albicans*" Infect Immun. Apr. 2006;74(4):2373-81.
Herrero AB, et al., "KRE5 Gene Null Mutant Strains of *Candida albicans* Are Avirulent and Have Altered Cell Wall Composition and Hypha Formation Properties" Eukaryot Cell. Dec. 2004;3(6):1423-32.
EJ Olson, et al. "Fungal b-Glucan Interacts with Vitronectin and Stimulates Tumor Necrosis Factor Alpha Release from Macrophages" Infect Immun. Sep. 1996;64(9):3548-54.
Torosantucci A, et al., "Differential chemokine response of human monocytes to yeast and hyphal forms of *Candida albicans* and its relation to the b-1,6 glucan of the fungal cell wall"J Leukoc Biol. Dec. 2000;68(6):923-32.
Sato T. et al., "Induction of human neutrophil chemotaxis by *Candida albicans*-derived_-1,6-long glycoside side-chain-branched_-glucan" J. Leuk. Biol. May 2006, vol. 80, epublication No. DOI:10.1189/jlb.0106069.

* cited by examiner

A

B

IMMUNOMODULATING COMPOSITIONS AND METHODS OF USE

CROSS-REFERENCE TO RELATED APPLICATIONS

This application is a National Phase Application of PCT International Application No. PCT/US07/23307, International Filing Date Nov. 6, 2007, claiming priority of U.S. Provisional Patent Applications, 60/856,834, filed Nov. 6, 2006, 60/880,384, filed Jan. 16, 2007 and 60/929,755, filed Jul. 11, 2007 all of which are incorporated herein by reference in their entirety.

GOVERNMENT INTEREST STATEMENT

This invention was made in whole or in part with government support under Grant Number GM035010-22 awarded by the National Institutes of Health. The government may have certain rights in the invention.

BACKGROUND OF THE INVENTION

The cell walls of fungi evoke a powerful immuno-stimulatory response, and have been proposed for use as potential anti-infective and anti-tumor drugs. Fungal cells can also activate dendritic cells and prime class II-restricted antigen-specific T cell responses. The majority of the cell wall (50-60%) of pathogenic (*Candida albicans*) and non-pathogenic fungi (*Saccharomyces cerevisiae*) is composed of an inner layer of β-glucan (β-1,3- and β-1,6-glucan) covalently linked to a variety of cell surface mannoproteins [Klis, F. M. et al. et al. Med Mycol 39 Suppl 1, 1-8, 2001; Klis, F. M. et al. et al., FEMS Microbiol Rev 26, 239-56, 2002].

Recognition of β-glucans by macrophages is carried out mainly through Dectin-1 with the cooperation of TLRs, including TLR2 [Brown, G. D. et al. et al. Nature 413, 36-7, 2001]. Dectin-1 activity is inhibited by β-1,3-glucans and β-1,6-glucans, with the β-1,3-glucan laminarins having the highest effect. However, oligosaccharide microarray results show that Dectin-1 binds specifically to β-1,3-glucans. Neutrophils are professional killers, whose role in phagocytosis and killing of bacteria and fungi is well characterized. Neutropenic individuals are much more susceptible to bacterial and fungal infections, with return to normal counts playing an important role in resolution of infection. Neutrophils, unlike macrophages, require serum for optimal phagocytosis and killing. The main opsonic receptors are the complement receptor CR3 and the immunoglobulin-binding receptor FcγR. CR3 has a lectin domain [Brown, G. D. et al. *Immunity* 19, 311-5, 2003] that mediates increased neutrophil motility towards a mixture of β-1,3-glucan and β-1,6-glucan (PGG-glucan) [Wakshull, E. et al. *Immunopharmacology* 41, 89-107, 1999]. Although neutrophils express Dectin-1 [Taylor, P. R. et al. *J Immunol* 169, 3876-82, 2002], its role in fungal recognition is not yet clear.

SUMMARY OF THE INVENTION

This invention provides, in one embodiment, a composition comprising β-1-6-glucan enriched for O-acetylated groups. In one embodiment, the glucan contains at least 25% by weight O-acetylated glucan. In one embodiment, the glucan is isolated or derived from lichen, which, in one embodiment, is from the genus Umbilicariaceae. In one embodiment, the glucan is isolated from a fungus. In one embodiment, the glucan is isolated from yeast, or in another embodiment the glucan is chemically synthesized or acetylated. In another embodiment, the glucan is conjugated to a particle.

In another embodiment, the composition comprises an adjuvant, an antigen, an immuno-modulatory compound, or a combination thereof.

In another embodiment, this invention provides a method of modulating an immune response in a subject, said method comprising administering to said subject a composition comprising β-1-6-glucan enriched for O-acetylated groups.

According to this aspect of the invention, and in one embodiment, modulating the immune response comprises stimulating said immune response, which, in one embodiment, is an antigen-specific response. In one embodiment, the composition further comprises an immuno-stimulatory compound, or in another embodiment, a chemotherapeutic compound. In another embodiment, the immune response is directed against an infectious agent, a cancer or other type of tumor, a pre-neoplastic lesion or a combination thereof. In another embodiment, the immune response is not directed against a cancer or other type of tumor.

In another embodiment, modulating the immune response comprises down-modulating or abrogating the immune response. According to this aspect, and in one embodiment, the composition further comprises an immunosuppressant. In one embodiment, the immune response is directed against an autoantigen or in another embodiment, an allergen, or in another embodiment, the immune response is directed against transplanted tissue or in another embodiment, transplanted cells. In one embodiment, the composition is administered to a subject suffering from an autoimmune disorder. In one embodiment the autoimmune disorder is associated with excessive neutrophil activity, neutrophil infiltration, neutrophil degranulation, etc. In one embodiment the disorder is a disorder that affects the skin; the composition may be applied directly to the skin.

In another embodiment this invention provides a composition comprising β-1-6-glucan, wherein the glucan is conjugated to a particle. According to this aspect, and in one embodiment, the glucan is enriched for O-acetylated groups, and in one embodiment, contains at least 25% by weight O-acetylated glucan. In another embodiment, the glucan is isolated or derived from a lichen or a yeast. In one embodiment, the glucan is isolated or derived from Umbilicariaceae. In another embodiment, the glucan is chemically synthesized or acetylated. In one embodiment, the glucan is conjugated to a microsphere, which, in one embodiment, has a diameter of about 0.1-15 microns.

In another embodiment, the composition comprises an adjuvant, an antigen, an immuno-modulatory compound, or a combination thereof.

In another embodiment, this invention provides a method of modulating an immune response in a subject, the method comprising administering to the subject a composition comprising β-1-6-glucan, wherein the glucan is conjugated to a solid support such as a particle.

In another embodiment, the invention provides a particle comprising β-1-6-glucan. In certain embodiments, the particle consists of at least 10%, 20%, 30%, 40%, 50%, 60%, 70%, 80%, 90%, 95%, 96%, 97%, 98%, or 99% β-1-6-glucan by dry weight. In certain embodiments, the particle consists essentially of β-1-6-glucan. Optionally, in certain embodiments, the β-1-6-glucan is enrich for O-acetylated groups. The invention further provides a method of modulating the immune response of a mammalian subject comprising administering any of the afore-mentioned particles, or a composition containing any of the afore-mentioned particles, to the subject.

In one embodiment, modulating the immune response comprises stimulating the immune response, which in one embodiment is an antigen-specific response. According to this aspect of the invention and in one embodiment, the composition further comprises an immuno-stimulatory compound or in another embodiment, a chemotherapeutic compound. In one embodiment, the immune response is directed against an infectious agent, a cancer or other type of tumor, a preneoplastic lesion or a combination thereof In another embodiment, modulating the immune response comprises downmodulating or abrogating the immune response. According to this aspect of the invention and in one embodiment, the composition further comprises an immunosuppressant. In one embodiment, the immune response is directed against an autoantigen or, in another embodiment, an allergen, or in another embodiment, transplanted tissue or, in another embodiment, transplanted cells. In one embodiment, the composition is administered to a subject suffering from an autoimmune disorder. In one embodiment the autoimmune disorder is associated with excessive neutrophil activity, neutrophil infiltration, neutrophil degranulation, etc. In one embodiment the disorder is a disorder that affects the skin, the composition may be applied directly to the skin.

In another embodiment, this invention provides a method of treating, delaying progression of, prolonging remission of, or reducing the incidence or severity of cancer in a subject, said method comprising administering to said subject a composition comprising purified β-1-6-glucan. In another embodiment, this invention provides a method of treating, delaying progression of, prolonging remission of, or reducing the incidence or severity of a tumor in a subject, said method comprising administering to said subject a composition comprising purified β-1-6-glucan.

In one embodiment, the β-1-6-glucan is enriched for O-acetylated groups, which in one embodiment contains at least 25-% by weight O-acetylated glucan. In another embodiment, the composition further comprises an adjuvant, an antigen, a peptide, an immuno-stimulatory compound, a chemotherapeutic or a combination thereof.

In one embodiment, the antigen is a tumor-associated antigen, or in another embodiment, the peptide is derived from a tumor-associated antigen.

In one embodiment, the subject has a hyperplastic or preneoplastic lesion. In another embodiment, the subject has cancer. In another embodiment, the subject has not been diagnosed with cancer. In another embodiment, the subject has not been diagnosed with a tumor.

In another embodiment, this invention provides a method of treating, delaying progression of, or reducing the incidence or severity of an infection in a subject, said method comprising administering to said subject a composition comprising purified β-1-6-glucan.

In one embodiment, the β-1-6-glucan is enriched for O-acetylated groups, which in one embodiment contains at least 25% by weight O-acetylated glucan. In another embodiment, the composition further comprises an adjuvant, an antigen, a peptide, an immuno-stimulatory compound, a to chemotherapeutic or a combination thereof.

In one embodiment, the antigen or peptide is derived from the source of the infection. In one embodiment, the immuno-stimulatory compound is a cytokine. In another embodiment, the chemotherapeutic compound is an antibiotic or antiviral compound. In one embodiment, the composition comprises a steroid. In another embodiment the composition comprises β-1,3 glucans having β-1,6-glucan branches (also referred to as beta 1,3/1,6, glucan or beta-1,6-branched beta-1,3-glucan) wherein at least some of the β-1,6-glucan branches are enriched for O-acetylated groups. In another embodiment the invention provides a composition comprising (i) β-1-6-glucan enriched for O-acetylated groups; and (ii) beta-1,6-branched beta-1,3-glucan.

In one embodiment, the invention provides a food supplement comprising β-1-6-glucan enriched for O-acetylated groups. In one embodiment, the invention provides a food product comprising β-1-6-glucan enriched for O-acetylated groups. In another embodiment, the invention provides a cosmetic composition comprising β-1-6-glucan enriched for O-acetylated groups.

In another embodiment, this invention provides a method of inducing expression of heat shock proteins in neutrophils, the method comprising contacting neutrophils with a composition comprising β-1-6-glucan, optionally enriched for O-acetylated groups. In another embodiment, this invention provides a method of inducing phagocytosis and production of reactive oxygen species in neutrophils, the method comprising contacting neutrophils with a composition comprising β-1-6-glucan, optionally enriched for O-acetylated groups. In another embodiment, this invention provides a method of inducing expression of heat shock proteins in neutrophils, the method comprising contacting neutrophils with a composition comprising β-1-6-glucan, wherein at least 25% of the glucose units in at least 5% of the glucan molecules are enriched for O-acetylated groups.

In any of the afore-mentioned embodiments the contacting may occur either outside the body of a subject or within the body. In one embodiment, cells, which in some embodiments are neutrophils, are removed from a subject, contacted with the composition, and then administered to the subject at a later time. In one embodiment the cells are contacted with the composition for a time sufficient to induce expression of heat shock proteins. In certain embodiments the cells are also contacted with serum or with one or more serum components. In one embodiment the subject receives immunosuppressive therapy prior to administration of the cells. For example, a subject may be in need of immunosuppressive therapy for organ transplantation or other purposes, e.g. chemotherapy or radiation therapy for cancer, leukemia, lymphoma, or any type of tumor, wherein the therapy would tend to render the individual immunocompromised. In one embodiment of the invention, prior to administering the immunosuppressive therapy, immune system cells are removed from the subject. The cells (which, in some embodiments, are neutrophils or in other embodiments, other immune system cells, such as other professional antigen-presenting cells, such as macrophages, dendritic cells, monocytes, NK cells, B cells or others) are contacted outside the body with a composition of this invention and are then returned to the subject a suitable period of time after the subject has received the immunosuppressive therapy. The suitable period of time could be, for example, after the therapy has been administered or its cytotoxic effects have diminished, when the subject is at risk of or exhibits symptoms or signs of infection, etc.

In one embodiment, the invention provides a method of inducing expression of heat shock proteins in a subject comprising administering β-1-6-glucan, optionally enriched for O-acetylated glucan, to a subject in an amount sufficient to induce expression of heat shock proteins in cells, e.g. neutrophils, of the subject. In one embodiment, the invention provides a method of inducing production of reactive oxygen species in a subject comprising administering β-1-6-glucan, optionally enriched for O-acetylated glucan, to a subject in an amount sufficient to induce production of reactive oxygen species by cells, e.g. neutrophils, of the subject. In one embodiment, the invention provides a method of enhancing phagocytosis in as subject comprising administering β-1-6-glucan, optionally enriched for O-acetylated glucan, to a subject in an amount sufficient to enhance phagocytosis by cells, e.g. neutrophils, of the subject.

The invention further provides a coated material comprising (a) a substrate; and (b) a compound or composition comprising β-1-6-glucan. In certain embodiments the β-1-6-glucan is enriched for O-acetylated glucan. In certain embodiments the coated material comprises a coating layer, e.g. a gel or a film, having the β-1-6-glucan physically associated therewith. In certain embodiments the coating layer comprises a polymer, e.g. an organic polymer, in addition to the β-1,6-glucan, wherein the polymer is physically associated with the β-1,6-glucan. In some embodiment the polymer is covalently bound to the β-1,6-glucan while in other embodiments the polymer is mixed with or impregnated with the β-1,6-glucan. In certain embodiments the coating layer contains between 1% and 90% β-1,6-glucan by dry weight. In certain embodiments the coating layer contains at least 10%, 20%, 30%, 40%, 50%, 60%, 70%, 80%, or 90% β-1,6-glucan by dry weight. In certain embodiments the coating layer comprises less than 10%, 20%, 30%, 40%, 50% β-1,6-glucan by dry weight.

A variety of different polymers are of use in the invention. Some suitable polymers are disclosed herein. In certain embodiments the polymer is biodegradable. In such embodiments the compound or composition may be released as the polymer degrades. In some embodiments the polymer is a poly(pyranose), poly(hydroxyl acid), poly(lactone), poly(amino acid), poly(anhydride), poly(urethane), poly(orthoester), poly(phosphazine), poly(phosphoester), poly(lactic) acid, poly(glycolic)acid, poly(lactic-co-glycolic)acid, poly(ether ester), poly(amino acid), synthetic poly(amino acid), polycarbonate, poly(hydroxyalkanoate), poly(ε-caprolactone), or poly(saccharide), or a mixture or blend of any of the foregoing. In certain embodiments the polymer is a copolymer, which in certain embodiments is a block copolymer, wherein the subunits are subunits found in any of the foregoing polymers. In certain embodiments a polymer of use in the invention has an average molecular weight (e.g. a number average or weight average molecular weight) of at least 10, 25, 50, 100, 200, or 300 kD, or a value falling within any intervening range. In certain embodiments a polymer of use in the invention is composed of, on average between 100 and 10,000 monomeric subunits, or any number of subunits falling within an intervening range. In certain embodiments the polymer is selected from polyethylene, polypropylene, polyvinyl chloride, polyethylene terephthalate, polystyrene and polycarbonate.

In one embodiment, the substrate is a part of, or in the form of a microparticle, nanoparticle, bandage, suture, catheter, stent, valve, pacemaker, implantable defibrillator, conduit, cannula, appliance, scaffold, central line (which may be a peripherally inserted central catheter (PICC or PIC line)), pessary, tube, drain, shunt, trochar, plug, or other implant or medical or surgical device. In one embodiment, the catheter is a pulmonary artery, pericardial, pleural, urinary or intra-abdominal catheter. In one embodiment, the drain is a cerebrospinal fluid drain. In one embodiment, the tube is a tracheostomy, endotracheal or chest tube. In another embodiment, the substrate is a part of, or in the form of an implant, a rod (e.g. a spinal rod such as a posterior spinal rod), a plate, a screw, washer, wire, pin, internal fixation devices (e.g. fracture fixation devices), or other implantable orthopedic hardware known to those of skill in the art.

Also provided by the present invention are methods of using the implant or other device. The implants and devices may be used in any manner in which conventional counterparts (e.g. counterparts not comprising and/or coated with a compound or composition disclosed herein) are used, such methods being known in the art. In some embodiments, a method of this invention is to be understood as comprising the treatment of any disease or condition with the implant or device of the invention. Also provided by the present invention are methods of delivering a compound or composition disclosed herein comprising a β-1,6-glucan to a subject, wherein the method comprises implanting or introducing a coated material, implant, or other device comprising a compound or composition of the invention into the body of the subject. Also provided by the present invention are methods of delivering a therapeutic agent not comprising a β-1,6-glucan to a subject using an implant or other device (e.g. a catheter, implantable pump, indwelling intravenous line, etc.) that comprises a β-1,6-glucan.

In another embodiment, this invention provides a composition comprising a β-1-6-glucan physically associated with a targeting moiety, for example one that specifically interacts with or attracts a phagocytic cell. According to this aspect of the invention and in one embodiment, the targeting moiety specifically interacts with an infected cell, a neoplastic cell, a pre-neoplastic cell, a pathogen or a component thereof, or is one that recruits phagocytic cells, for example, to sites of neoplasia, preneoplasia, infection, etc. According to this aspect of the invention and in one embodiment, the targeting moiety specifically interacts with an infected cell, a neoplastic cell, a pre-neoplastic cell, a pathogen, or a component thereof. In one embodiment, the glucan is enriched for O-acetylated groups, and in one embodiment, the glucan contains at least 25% by weight O-acetylated glucan. In another embodiment, the glucan is isolated or derived from a lichen or a yeast, which in one embodiment is Umbilicariaceae. In one embodiment, the glucan is chemically synthesized or acetylated. In another embodiment, the composition further comprises an adjuvant, an antigen, an immuno-modulatory compound, or a combination thereof. In another embodiment, the phagocytic cell is a professional antigen-presenting cell. In another embodiment, the phagocytic cell is a neutrophil.

In one embodiment, the targeting moiety is an antibody or antibody fragment.

In another embodiment, the invention provides a method modulating an immune response in a subject, the method comprising administering to the subject a composition comprising a β-1-6-glucan physically associated with a targeting moiety, for example, wherein the targeting moiety specifically interacts with or attracts a phagocytic cell, or comprises any embodiment as herein described.

In one embodiment, modulating said immune response comprises stimulating said immune response, which in one embodiment is an antigen-specific response. In one embodiment, the composition further comprises an immuno-stimulatory compound, or in another embodiment, the composition further comprises a chemotherapeutic compound. In one embodiment, the immune response is directed against an infectious agent, a cancer, a pre-neoplastic lesion or a combination thereof, and in another embodiment, the immune response is complement-dependent.

In one embodiment, this invention provides a method of treating, delaying progression of, or reducing the incidence or severity of an infection in a subject, said method comprising administering to said subject a composition comprising a β-1-6-glucan physically associated with a targeting moiety, for example, wherein the targeting moiety specifically interacts with or attracts a phagocytic cell, or comprises any embodiment as herein described. In one embodiment, the composition further comprises an adjuvant, an antigen, a peptide, an immuno-stimulatory compound, a chemotherapeutic or a combination thereof. In one embodiment, the antigen or peptide is derived from the source of the infection. In another embodiment, the immuno-stimulatory compound is a cytokine. In another embodiment, the chemotherapeutic compound is an antibiotic or antiviral compound.

In one embodiment, this invention provides a method of stimulating or enhancing heat shock protein expression in a cell, the method comprising contacting the cell with a composition comprising a β-1-6-glucan physically associated with a targeting moiety, for example, wherein the targeting moiety specifically interacts with or attracts a phagocytic cell, or comprises any embodiment as herein described.

In another embodiment, this invention provides a method of modulating an immune response in a subject, said method comprising administering to said subject a composition comprising β-1-6-glucan, wherein said glucan is conjugated to a particle, as herein described.

In another embodiment, this invention provides a method of treating, delaying progression of, prolonging remission of, or reducing the incidence or severity of cancer in a subject, said method comprising administering to said subject a composition comprising a glucan as herein described, for example, a purified β-1-6-glucan, a preparation enriched for O-acetylated β1-6-glucan, a β-1-6-glucan conjugated to a particle or a β-1-6-glucan linked to a targeting moiety or a combination thereof.

In another embodiment, this invention provides a micelle comprising β-1,6-glucan, wherein said β-1,6-glucan is optionally enriched for O-acetylated glucan. In another embodiment, this invention provides a composition comprising β-1,6-glucan and a biodegradable polymer, wherein said biodegradable polymer degrades to form biologically active salicylate or alpha-hydroxy acid moieties and said β-1,6-glucan is optionally enriched for O-acetylated glucan. In another embodiment, this invention provides for the use of any glucan, any composition, any micelle or combination thereof for any method as herein described.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or subrange within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

untreated beads, (b) beads coated with β-1,3-glucan from *Candida* (c) beads coated with laminarin (lam, β-1,3-glucan), (d) beads coated with glucan from barley (bar), (e) beads coated with pustulan (pus, β-1,6-glucan) (f) soluble pustulan. (C) β-1,6-glucan stimulates ROS production. ROS production was assayed by FACS using DHR123. β-1,3-glucan shows only a modest stimulation.

Figure 4:
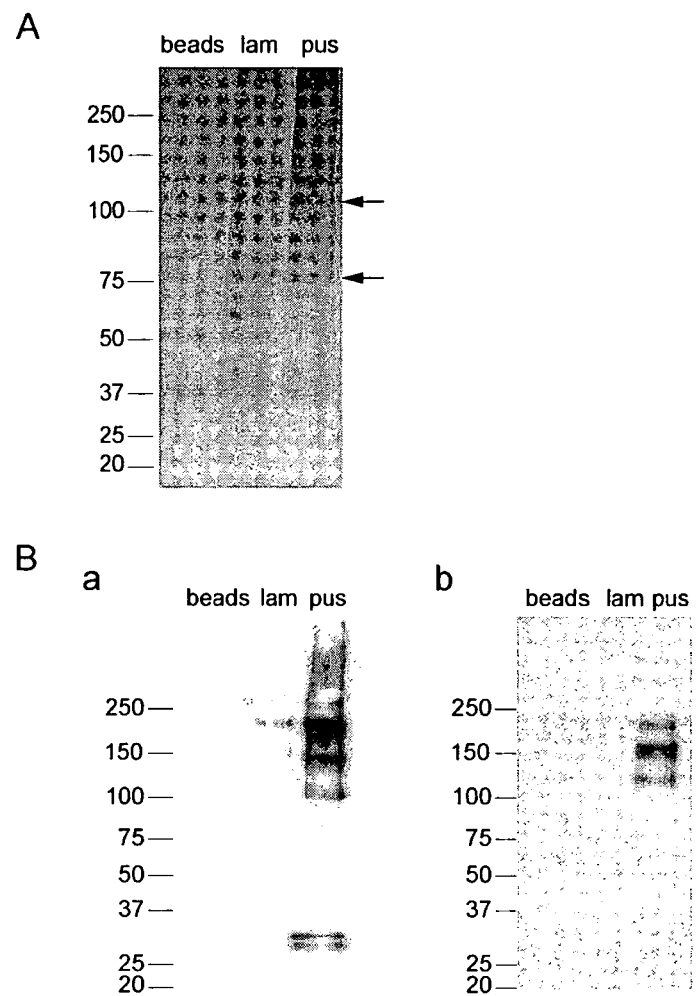

FIG. 4. C3 proteolytic fragments are deposited on β-1,6-glucan. Beads were untreated (Beads), or coated with equivalent amount of laminarin (lam, β-1,3-glucan), or pustulan (pus, β-1,6-glucan). Following opsonization, the beads were suspended in 2% SDS 1M ammonium hydroxide buffer and incubated at 37° C. for 1 hour. The supernatant solution was loaded on 4-20% acrylamide SDS gel. The migration of the molecular weight protein standards is indicated. (A) The gel was incubated with silver stain, and the bands were extracted for analysis by mass spectrometry. (B) Western analysis was performed using monoclonal antibodies directed against (a) the alpha or (b) the beta chains of C3.

Figure 5:
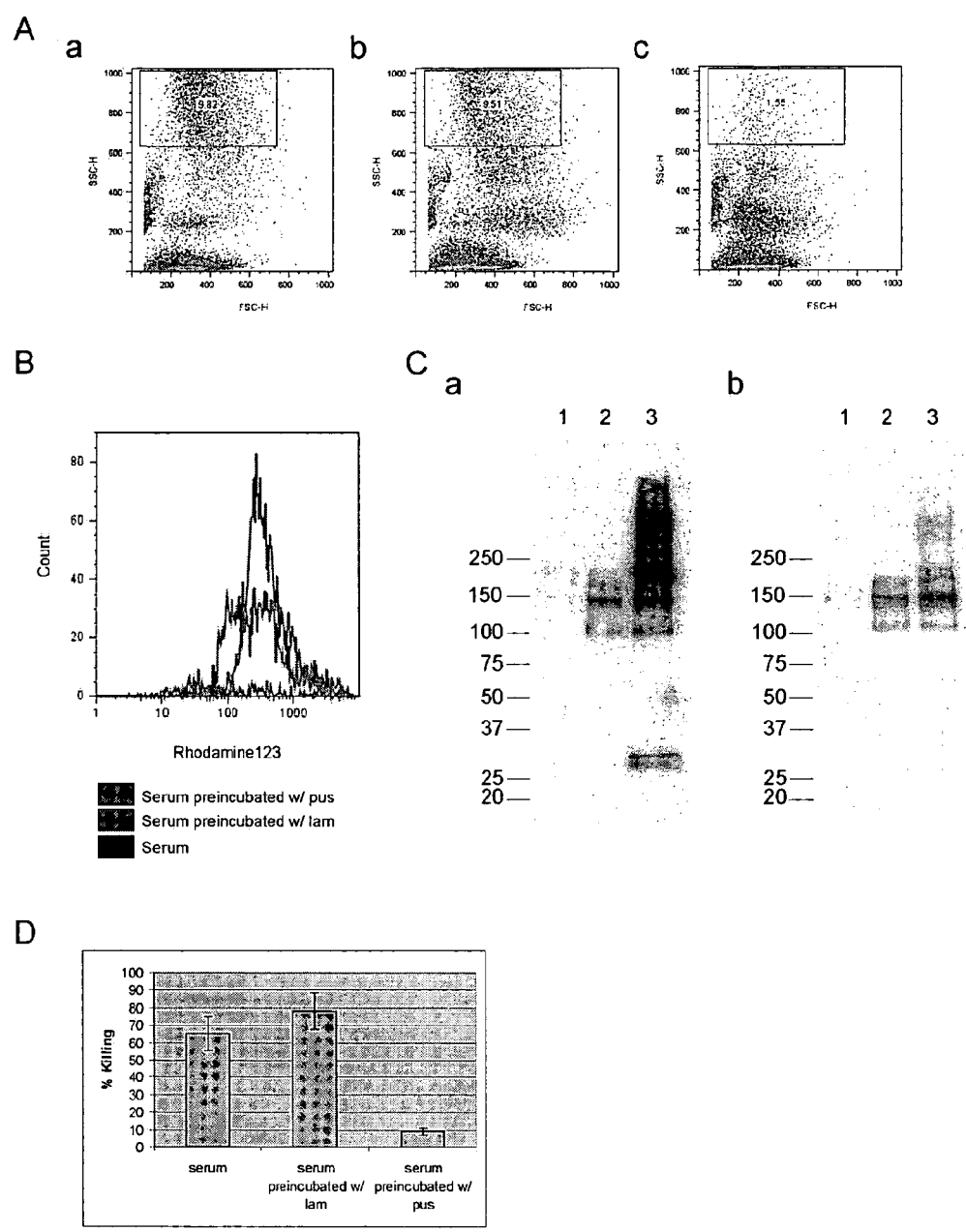

FIG. 5. Preincubation of serum with soluble pustulan (β-1, 6-glucan) abolishes stimulation of neutrophils, whereas soluble laminarin (β-1,3-glucan) does not. (A) Phagocytosis of pustulan-coated beads was assessed by FACS, by the change in side scatter. Serum was untreated (a), or incubated for 5 minutes at 37° C. with 1 mg (quantified by phenol-sulfuric acid method) of soluble laminarin (lam) (b) or pustulan (pus) (c). (B) Reactive oxygen species production in response to pustulan-coated beads was assayed by FACS using DHR123. Serum was untreated (red), incubated with soluble laminarin (green), or with pustulan (blue). (C) C3 deposition on pustulan-coated beads was eliminated by preincubation of the serum by soluble pustulan but not laminarin. C3 deposition was assayed by Western analysis using monoclonal antibodies directed against the (a) alpha or (b) the beta chains of C3. Serum was preincubated with soluble pustulan (1), laminarin (2), or was untreated (3). The molecular weight protein standard is indicated. (D) Preincubation of serum with soluble pustulan reduces *Candida* killing. Serum was untreated, or preincubated with soluble pus or lam prior to opsonization of *Candida*. *Candida* viability was assayed using XTT following incubation of 30 minutes with neutrophils.

Figure 6:
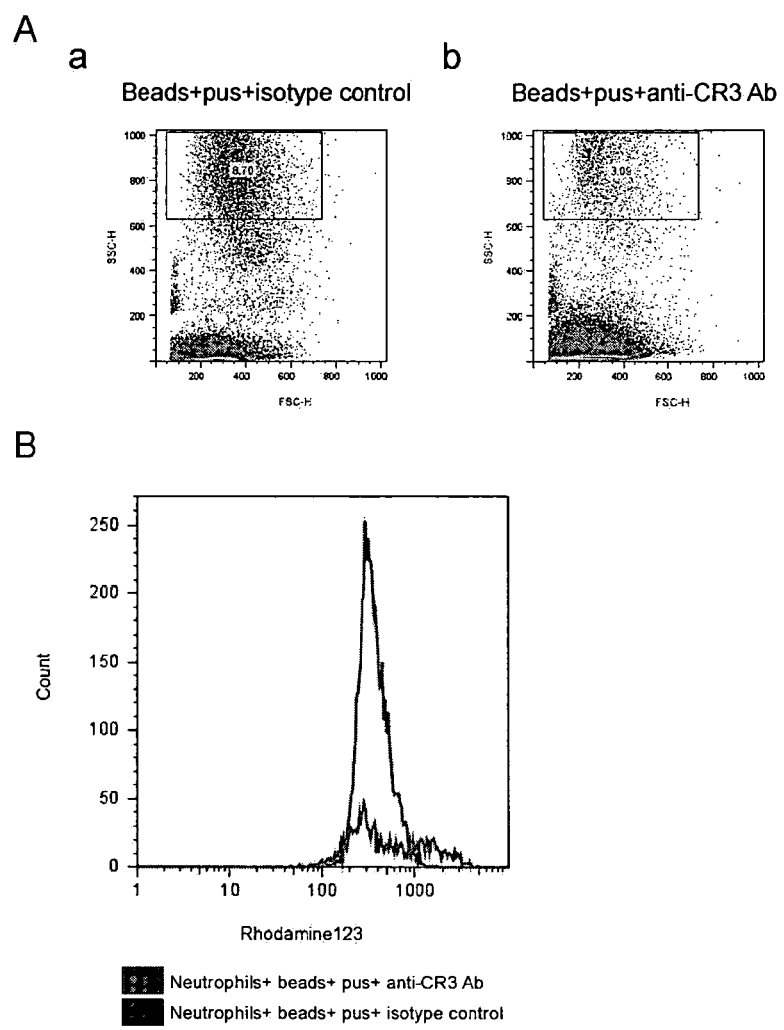

FIG. 6. CR3 mediates β-1,6-glucan stimulation of neutrophils. Polybead polystyrene 6.0 micron microspheres (beads) were coated with the β-1,6-glucan pustulan (pus). Beads were opsonized with pooled human serum and cultured with neutrophils for 15 minutes. Neutrophils were preincubated with CR3 blocking antibodies or IgG isotype control for 30 minutes on ice before culturing with pustulan-coated beads. (A) CR3 blocking antibodies reduce β-1,6-glucan-stimulated phagocytosis. Phagocytosis of pustulan-coated beads was assessed by FACS by the change in side scatter for neutrophils preincubated with: (a) isotype control IgG, or (b) anti-CR3 blocking antibodies. (B) CR3 blocking antibodies reduce β-1, 6-glucan-stimulated ROS production. ROS production in response to pustulan-coated beads was assayed by FACS using DHR123. Neutrophils were preincubated with isotype control IgG (green) or anti CR3 blocking Ab (red).

Figure 7:
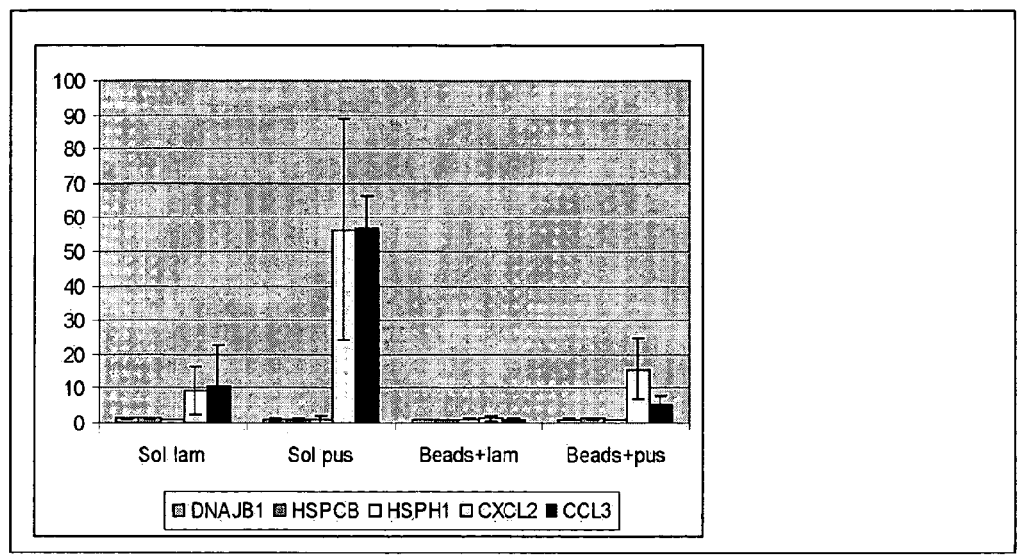

FIG. 7. β-1,6-glucan elicits chemokines in monocytes. Polybead polystyrene 6.0 micron microspheres (beads) were coated with equivalent amount of the β-1,3-glucan laminarin (lam), or the β-1,6-glucan pustulan (pus). Beads were opsonized with pooled human serum. Monocytes were cultured for 2 hours with 5 mg/ml of soluble lam or pus, or with the beads described above. Induction of chemokines was determined by quantitative real-time PCR. Results were averaged and standard deviations were calculated.

Figure 8:
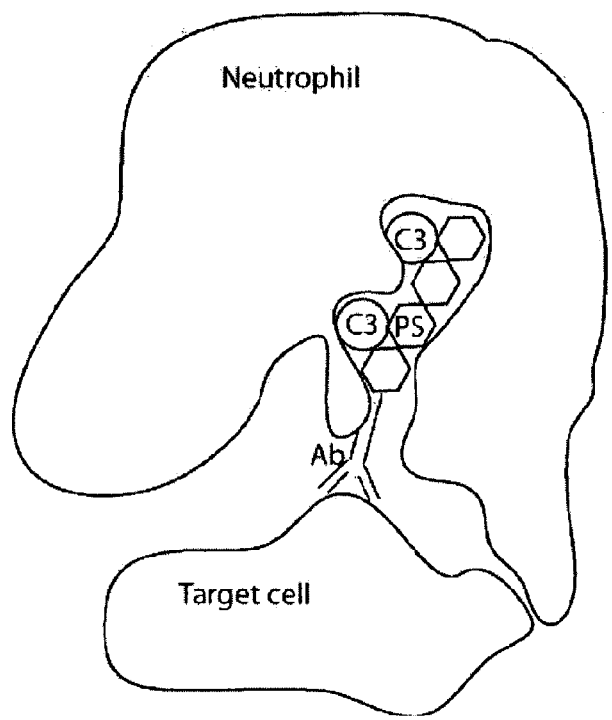
Figure 9:
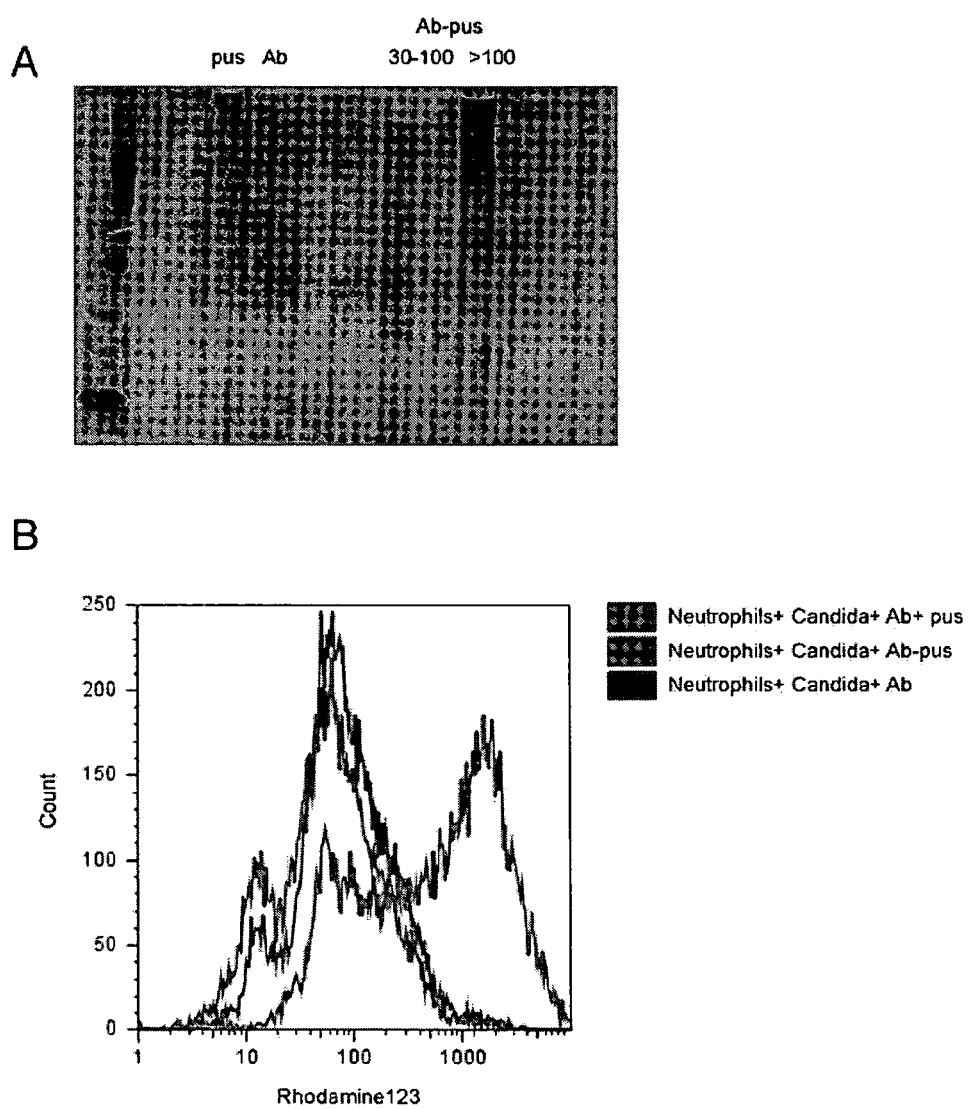

FIG. 8. Schematic depiction of pustulan-antibody chimera activity in cellular targeting and complement deposition, leading to neutrophil engulfment. Antibody (Ab) is physically linked to polysaccharide (PS). Complement (C3) deposition recruits neutrophils to target cells as a function of the antibody specificity FIG. 9. Elicitation of high reactive oxygen species by human neutrophils post-exposure to pustulan-anti-*Candida albicans* monoclonal antibody chimeras. Anti-*C. albicans* antibody (Ab)-pustulan (pus) (Ab-pus) complexes 30-100 kDa or higher than 100 kDa (>100) in size were loaded on polyacrylamide gels and silver-stained (A). ROS production was assayed by Fluorescence-Activated Cell Sorting using DHR123 (B).

Figure 10:
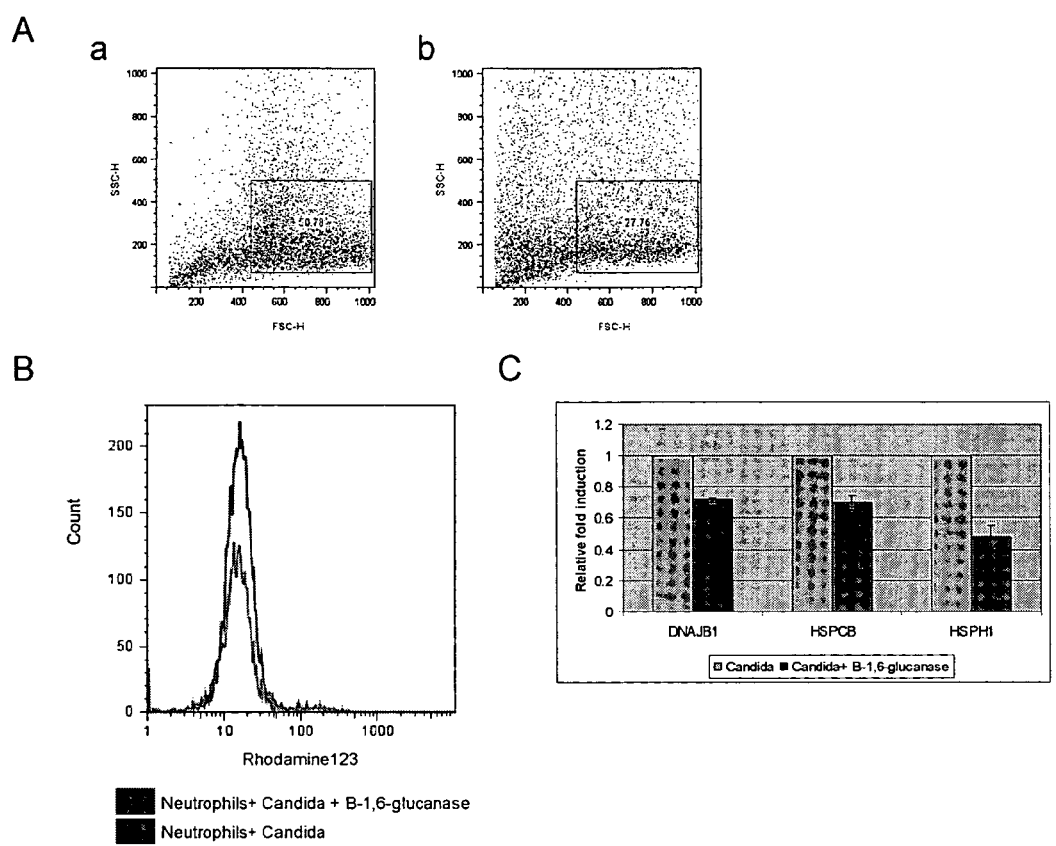

FIG. 10. β-1,6-glucan is required for efficient phagocytosis of *Candida albicans*, production of ROS, and expression of HSPs. *Candida albicans* cells were heat-killed, digested with an endo-β-1,6-glucanase, and opsonized. (A) β-1,6-glucan is required for efficient phagocytosis. Phagocytosis was assessed by Fluorescence-Activated Cell Sorting (FACS) by the change in side scatter. (B) β-1,6-glucan is required for efficient ROS production. ROS production was assayed by FACS using DHR123. (C) β-1,6-glucan is required for induction of HSPs. HSPs induction was determined by quantitative real-time PCR. Results for β-1,6-glucanase digested *Candida* were normalized to undigested *Candida*. The data represent the average of two experiments with standard deviation.

Figure 11:
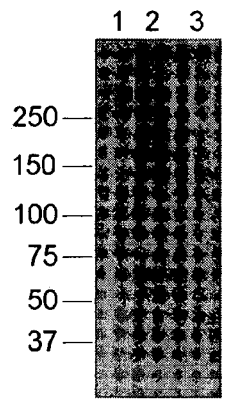
Figure 11:
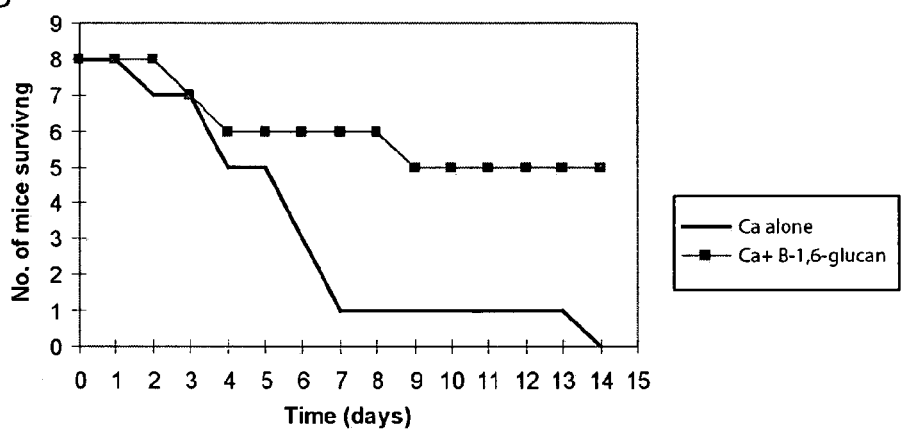

FIG. 11. (A) Mouse serum activates complement. Beads were untreated (1), or coated with equivalent amount of pustulan (β-1,6-glucan) (2) or laminarin (β-1,3-glucan) (3). Following opsonization with mouse (C57Black/6) serum, the beads were suspended in 2% SDS 1M ammonium hydroxide buffer and incubated at 37° C. for 1 hour. The supernatant solution was loaded on 4-20% to acrylamide SDS gel. The migration of the molecular weight protein standards is indicated. Western analysis was performed using anti-mouse C3 antibodies. (B) β-1,6-glucan-coated beads protect mice from systemic fungal infection. *Candida albicans* cells ($10^6$) were injected into the tail vein of C57Black/6 mice. $10^5$ β-1,6-glucan-coated beads or untreated beads were injected the next day into the tail vein of the same mice. Survival was monitored daily.

Figure 12:
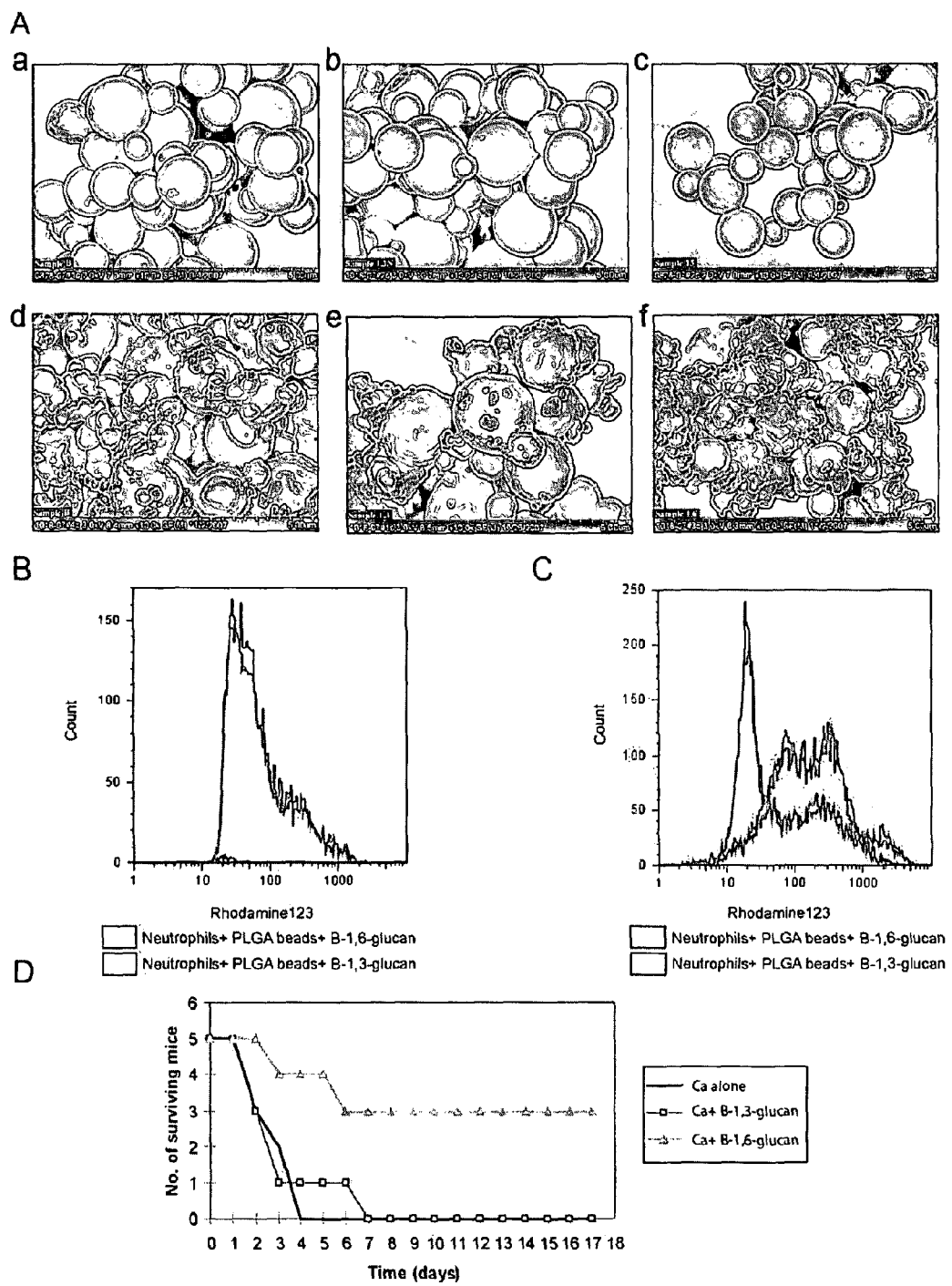

FIG. 12. PLGA beads encapsulating β-1,6-glucan elicit production of reactive oxygen species and protect mice from systemic fungal infection. PLGA beads were made with 250 mg polysaccharide per mg of PLGA. (A) SEM images of PLGA beads (a,d) or PLGA beads encapsulating β-1,3-glucan (b,e) or β-1,6-glucan (c,f) at day 0 (a-c) or after 3 days (d-f). (B) β-1,6-glucan is detected on the surface of degrading PLGA beads. β-1,6-glucan was detected on degrading PLGA beads following 3 days of incubation in PBS, using polyclonal anti-β-1,6-glucan antibodies. (C) PLGA beads encapsulating β-1,6-glucan (7.17 microgram glucose/mg of PLGA) (green) elicit higher levels of reactive oxygen species than PLGA beads encapsulating β-1,3-glucan (37.1 microgram glucose/mg of PLGA) (red). (D) PLGA beads encapsulating β-1,6-glucan protect mice from systemic fungal infection. *Candida albicans* cells ($10^6$) were injected into the tail vein of C57Black/6 mice. $10^5$ PLGA beads encapsulating β-1,6-glucan beads, PLGA beads encapsulating β-1,3-glucan or PLGA beads were injected the next day into the tail vein of the same mice. Survival was monitored daily.

Figure 13:
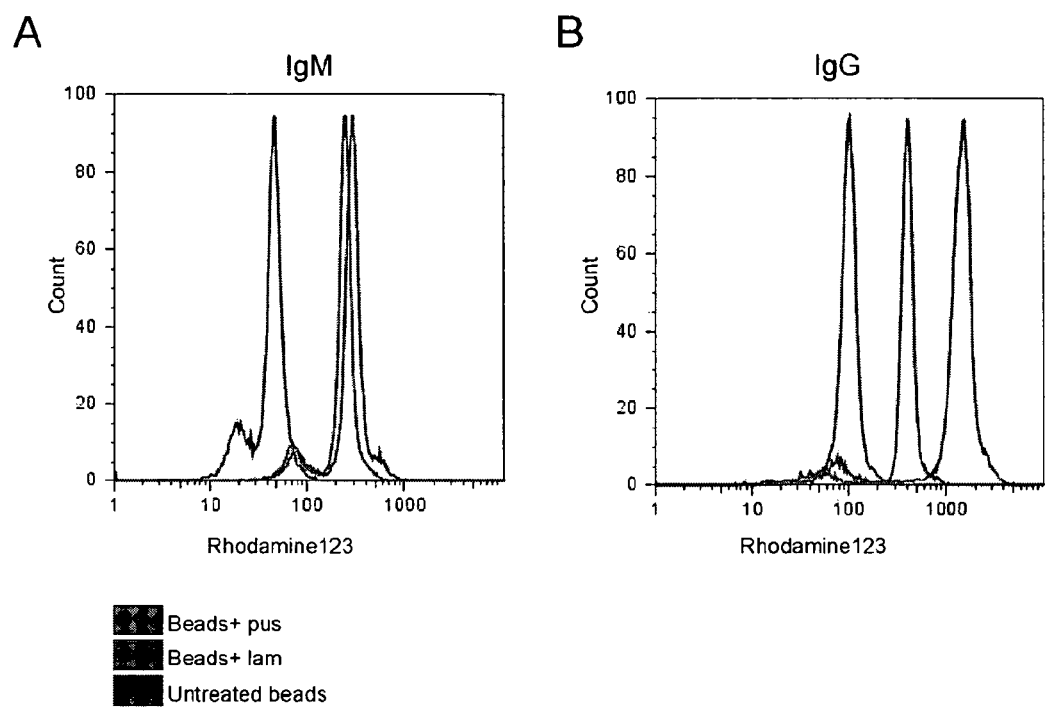

FIG. 13. High levels of IgG are detected on β-1,6-glucan. Beads were untreated (red), or coated with equivalent amount of laminarin (β-1,3-glucan) (green) or pustulan (β-1,6-glucan) (blue). Following opsonization, IgM and IgG deposition was detected using anti-human IgM and IgG antibodies.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Glucans are polysaccharides found in all studied species of lichenized fungi. Partially O-acetylated pustulans are typical of Umbilicariaceae, and have been described for several species of *Umbilicaria*, such as *U. pustulata* and *U. hirsute, U. angulata, U. caroliniana*, and *U. polyphylla*.

β-1,6-glucans, were found to induce specific gene expression in contrast to β-1,3-glucans, which activity may be useful in modulating immune responses. Without intending any limitation, O-acetylated β-1,6-glucans were found to be useful in this context. Without intending any limitation, β-1,6-glucans were also found to induce phagocytosis and reactive oxygen species production by neutrophils. Reactive oxygen species are an important component of the killing mechanism in neutrophils, and therefore, this activity of β-1,6-glucan may be useful in modulating immune responses. In one embodiment, the invention provides a method of inducing production of reactive oxygen species in a subject comprising administering β-1-6-glucan, optionally enriched for O-acetylated glucan, to a subject in an amount sufficient to induce phagocytosis and production of reactive oxygen species by cells, e.g. neutrophils, of the subject. Reactive oxygen species (ROS) include molecules such as oxygen ions, free radicals and peroxides both inorganic and organic. In certain embodiments they are small molecules and are highly reactive due to the presence of unpaired valence shell electrons. In one embodiment, the ROS is superoxide.

This invention provides a composition comprising purified β-1-6-glucan, wherein the composition is, in various embodiments of the invention, a pharmaceutical composition, a food or food product, a food supplement, or a cosmetic composition. The composition is, in some embodiments, distinct from compositions such as pustulan or preparations of fungal cell walls. In certain embodiments of the invention at least 10%, 20%, 30%, 40%, 50%, 60%, 70%, 80%, 90%, 95%, 98%, 99% or more of the glucan contained in the composition by weight is β-1-6-glucan. In certain embodiments between 20% and 50% of the glucan contained in the composition is β-1-6-glucan. In certain embodiments between 50% and 100% of the glucan contained in the composition is β-1-6-glucan. In one embodiment of any of the compositions or methods of the invention, the glucan contains from about 15% to about 30% by weight β-1-6-glucan. In another embodiment of any of the compositions or methods of the invention, the glucan contains from about 10% to about 35% by weight β-1-6-glucan, or in another embodiment, from about 20% to about 50% by weight β-1-6-glucan, or in another embodiment, from about 25% to about 60% by weight β-1-6-glucan, or in another embodiment, from about 35% to about 80% by weight β-1-6-glucan, or in another embodiment, from about 18% to about 35% by weight β-1-6-glucan, or in another embodiment, from about 15% to about 75% by weight β-1-6-glucan. In certain embodiments of the invention "weight" refers to "dry weight". In other embodiments "weight" refers to total weight. In certain embodiments of the invention the β-1-6-glucan is processed. Such processing may comprise, for example, deacetylation, treatment with enzymes that digest glucans other than β-1-6-glucan, limited digestion with enzymes that digest β-1-6-glucan, selection of particular molecular weight ranges, etc. In certain embodiments, processing comprises separation from other glucans, e.g. β-glucans, β-1-3 glucans, etc. In certain embodiments the processing comprises removing β-1-6-glucan side chains from β-1-3 glucans and optionally separating the β-1-6-glucans side chains. In certain embodiments the composition comprises processed β-1-6-glucan, wherein the processed β-1-6-glucan exhibits enhanced ability to desirably modulate the immune response relative to unprocessed glucan or relative to unprocessed β-1-6-glucan.

This invention provides, in one embodiment, a composition comprising β-1-6-glucan enriched for O-acetylated groups. In one embodiment of any of the compositions or methods of the invention, the glucan contains at least 25% by weight O-acetylated glucan. In one embodiment of any of the compositions or methods of the invention, the glucan contains from about 15% to about 30% by weight O-acetylated glucan. In another embodiment of any of the compositions or methods of the invention, the glucan contains from about 10% to about 35% by weight O-acetylated glucan, or in another embodiment, from about 20% to about 50% by weight O-acetylated glucan, or in another embodiment, from about 25% to about 60% by weight O-acetylated glucan, or in another embodiment, from about 35% to about 80% by weight O-acetylated glucan, or in another embodiment, from about 18% to about 35% by weight O-acetylated glucan, or in another embodiment, from about 15% to about 75% by weight O-acetylated glucan. In other embodiments, the glucan contains between about 75% and 100% by weight O-acetylated glucan, e.g. between 75% and 90%, or between 90% and 100% by weight O-acetylated glucan. In one embodiment of any of the compositions or methods of the invention the glucan contains approximately that percentage of O-acetylated glucose units (by weight or number, in various embodiments of the invention) that would result from digestion of a naturally occurring β-1-6-glucan (e.g. pustulan or any other β-1-6-glucan mentioned herein) with a β-1-6 endoglucanase for a time sufficient to digest at least 90% by weight of the β-1-6-glucan to oligosaccharides comprising 5 or fewer glucose units followed by (i) removal of those oligosaccharides comprising 5 or fewer glucose residues from the composition or (ii) isolation of a portion of the resulting composition having a molecular weight greater than 5 kD, or in some embodiment greater than 10, 20, 30, 50, or 100 kD.

In some embodiments, the term "enriched for O-acetylated residues" refers to the enhanced % of O-acetylated sites in individual glucose units within the glucan molecule, enhanced % of O-acetylated glucose units within the glucan molecule, or a combination thereof, as compared to a native glucan molecule. In one embodiment, reference to glucan preparations enriched by a particular weight percent for O-acetylated glucan, refers to preparations comprising an enhanced % of O-acetylated sites in individual glucose units within the glucan molecule, an enhanced % of O-acetylated glucose units within the glucan molecule, or a combination thereof, as compared to a glucan molecule.

Glucans derived from different sources may comprise varying amounts of O-acetylation in terms of O-acetylated sites in individual glucose units, O-acetylated glucose units within the glucan molecule, or a combination thereof. According to this aspect of the invention, the term "enriched for O-acetylated glucan" refers, in some embodiments, to enhanced O-acetylation as described herein, between the reference source from which the glucan is derived, and may not represent an overall enrichment as compared to any glucan source.

In one embodiment, the term "enriched for O-acetylated glucan" refers, to an enrichment of at least 25% by weight of the glucan chains, which are O-acetylated on at least one glucose unit, or at least 25% of the glucose units present in the glucan in the composition are O-acetylated, or a combination thereof. In some embodiments, at least 25% of the glucose units in at least 1%, or in another embodiment, at least 5% of the beta glucan chains are O-acetylated. In other embodiments between 25% and 35%, between 25% and 50%, between 25% and 75%, between 15% and 45%, between 20% and 60%, between 35% and 80%, or others of the glucose units in at least 5% of the beta glucan chains are O-acetylated, etc. In other embodiments, embodiments between 25% and 35%, between 25% and 50%, between 25% and 75%, between 15% and 45%, between 20% and 60%, between 35% and 80%, or others of the glucose units, in at least 10% of the beta glucan chains, or in another embodiment, in at least 15% of the beta glucan chains, or in another embodiment, in at least 20% of the beta glucan chains, are O-acetylated.

In one embodiment, the glucan is isolated or derived from a lichen, which in one embodiment is from the genus Umbilicariaceae. In one embodiment, the glucan is isolated from a fungus. In one embodiment, the fungus is an edible mushroom, inter alia, *Grifola frondosa* (maitake), *Cordyceps sinensis, Agaricus brasiliensis, Inonotus obliquus* (Chaga)). In one embodiment, the glucan is isolated from yeast, or in another embodiment the glucan is chemically synthesized or acetylated. In one embodiment, short synthetic β-1,6-glucan polymers are linked through linkers (e.g. diamine) to form long polymers. In another embodiment, the glucan is conjugated to a solid support.

Glucans are glucose-containing polysaccharides found, inter alia, in fungal cell walls. α-glucans include one or more α-linkages between glucose subunits and β-glucans include one or more β-linkages between glucose subunits β-1,6-glucans occur frequently in fungi but are rarer outside fungi. The glucan used in accordance with the invention comprises β-1,6-glucan. In some embodiments, the β-glucans are derived from Umbilicariaceae, such as *U. pustulata* and *U. hirsute, U. angulata, U. caroliniana,* and *U. polyphylla*.

In some embodiments, the β-glucans are derived from *Candida*, such as *C. albicans*. Other organisms from which β-glucans may be used include *Coccidioides immitis, Trichophyton verrucosum, Blastomyces dermatidis, Cryptococcus neoformans, Histoplasma capsulatum, Saccharomyces cerevisiae, Paracoccidioides brasiliensis,* and *Pythiumn insidiosum*. In some embodiments, the β-glucans are chemically or enzymatically synthesized, as is known in the art, or in other embodiments, the β-glucans are derived from any species producing the same, and chemically or enzymatically altered, for example, to increase O-acetylation of the molecule.

In some embodiments, the β-glucans are fungal glucans. A 'fungal' glucan will generally be obtained from a fungus but, where a particular glucan structure is found in both fungi and non-fungi (e.g. in bacteria, lower plants or algae) then the non-fungal organism may be used as an alternative source.

Full-length native β-glucans are insoluble and have a molecular weight in the megadalton range. In some embodiments, this invention provides soluble β-1,6-glucan. In some embodiments, this invention provides soluble O-acetylated β-1,6-glucan. Solubilization may be achieved by fragmenting long insoluble glucans, in some embodiments. This may be achieved by, for example, hydrolysis or, in some embodiments, by digestion with a glucanase (e.g. with a β-1,3 glucanase or limited digestion with a β-1,3 glucanase). In other embodiments, glucans can be prepared synthetically, for example, and in some embodiments, by joining monosaccharide building blocks. O-acetylation of such glucans can readily be accomplished by methods known in the art. Such methods may include chemical and/or enzymatic acetylation, such as are known in the art.

There are various sources of fungal β-glucans. For instance, pure β-glucans are commercially available e.g. pustulan (Calbiochem) is a β-1,6-glucan purified from *Umbilicaria papullosa*. β-glucans can be purified from fungal cell walls in various ways, for example, as described in Tokunaka et al. [(1999) Carbohydr Res 316:161-172], and the product may be enriched for β-1,6-glucan moieties, or O-acetylated β-1,6-glucan moieties, by methods as are known in the art.

One of ordinary skill in the art will be able to identify or select appropriate methods to enrich for β-1,6-glucan moieties and/or for O-acetylated β-1,6-glucan. In one embodiment, O-acetylation of beta-glucan is performed chemically. For example, polysaccharides (50 mg) are dried in a speed vac centrifuge and resuspended in 1.5 ml of acetic anhydride (Mallindcrockdt). After resuspension, a few crystals of 4-dimethylaminopyridine (Avocado Research Chemist, Ltd) are added as catalyst. The reaction is allowed to proceed at room temperature for 5, 20, or 120 minutes and then stopped with 2 volumes of water. Afterwards the samples are dialyzed overnight against water. It will be appreciated that this process could be varied or scaled up, as evident to one of skill in the art. In other embodiments, methods for separating O-acetylated β-1,6-glucan include one or more of the following steps, which could be performed in various orders: (a) separation based on higher hydrophobicity, such as binding to any hydrophobic matrix/resin; (b) separation based on digestion with a suitable endo- or exo-glucanase or combination thereof, wherein the O-acetylated β-1,6-glucan is resistant to digestion; (c) affinity separation using antibodies or other moieties that bind to β-1,6-glucan or to O-acetyl groups thereon; (d) separation based on molecular weight. In one embodiment, β-1,6-glucan is digested with an enzyme that digests unacetylated and/or lightly acetylated β-1,6-glucan. The resulting material is separated based on size or molecular weight and a portion comprising heavily acetylated glucan is isolated. In some embodiments, β-1,6-glucan preparations are obtained, digested and O-acetylated oligosaccharides are separated or in another embodiment, isolated, and used in the preparation of new compositions. Such compositions represent embodiments of the β-1,6-glucan preparations enriched for O-acetylated residues of this invention.

It is to be understood that the products of any process for preparing enriched O-acetylated β-1,6-glucan preparations are to be considered as part of this invention.

In some embodiments, the glucans for use in the compositions, preparations, micelles and/or according to the methods of this invention may comprise structural modifications, not present in native glucan preparations. Such modifications may comprise, O-acetylation, as described herein. In other embodiments, such modifications may comprise methylation, alkylation, alkoylation, sulfation, phosphorylation, lipid conjugation or other modifications, as are known to one skilled in the art. In some embodiments the modification comprises modification (e.g. esterification) with an acid such as formic, succinic, citric acid, or other acid known in the art.

In some embodiments, lipid conjugation to any or all free hydroxyl groups may be accomplished by any number of means known in the art, for example, as described in Drouillat B, et al., Pharm Sci. 1998 January; 87(1):25-30, B. N. A. Mbadugha, et al., Org. Lett., 5 (22), 4041-4044, 2003.

In some embodiments, methylation may be accomplished and verified by any number of means known in the art, for example, as described in Mischnick et al. 1994 Carbohydr. Res., 264, 293-304; Bowie et al. 1984, Carbohydr. Res., 125, 301-307; Sherman and Gray 1992, Carbohydr. Res., 231, 221-235; Stankowski and Zeller 1992, Carbohydr. Res., 234, 337-341; Harris, P. J., et al. (1984) Carbohydr. Res. 127, 59-73; Carpita, N. C. & Shea, E. M. (1989) Linkage structure of carbohydrates by gas chromatography-mass spectrometry (GC-MS) of partially methylated alditol acetates. In Analysis of Carbohydrates by GLC and MS (Biermann, C. J. & McGinnis, G. D., eds), pp. 157-216. CRC Press, Boca Raton, Fla.

In some embodiments, methylation can be confirmed by GLC of further-derived TMS ethers, acetates or other esters, coupled MS, or digestion to monosaccharides, de-O-methylation and analysis by derivatization and GLC/MS, for example as described in Pazur 1986, Carbohydrate Analysis—A Practical Approach, IRL Press, Oxford, pp. 55-96; Montreuil et al. 1986, Glycoproteins. In M. F. Chaplin and J. F. Kennedy, (eds.), Carbohydrate Analysis—a Practical Approach, IRL Press, Oxford, pp. 143-204; Sellers et al. 1990, Carbohydr. Res., 207, C1-C5; O'Neill et al. 1990, Pectic polysaccharides of primary cell walls. In P. M. Dey (ed.), Methods in Plant Biochemistry, Volume 2, Carbohydrates, Academic Press, London, pp. 415-441; Stephen et al. 1990, Methods in Plant Biochemistry, Volume 2, Carbohydrates, Academic Press, London, pp. 483-522; or Churms 1991, CRC Handbook of Chromatography. Carbohydrates, Volume II, CRC Press, Boca Raton, Fla., USA).

In some embodiments, phosphorylation, optionally including the introduction of other modifications, and verification of the obtained product may be accomplished by means well known to those skilled in the art, see for example, Brown, D. H., Biochem. Biophys. Acta, 7, 487 (1951); Roseman, S., and Daffner, I., Anal. Chem., 28, 1743 (1956); Kornberg, A., and Horecker., B. L., in Methods in enzymology, Vol. I, Academic Press, New York, 1955, p. 323; U.S. Pat. No. 4,818,752.

In some embodiments, glucan sulfation and verification of the obtained product may be accomplished by any of the means well known in the art, for example, as described in Alban, S., and Franz, G. (2001), Biomacromolecules 2, 354-361; Alban, et al. (1992) Arzneimittelforschung 42, 1005-1008; or Alban, S., et al. (2001). Carbohydr. Polym. 47, 267-276.

Also provided by the invention is a micelle comprising β-1,6-glucan. In certain embodiments the micelle comprises a complex composed of surfactant molecules comprising β-1,6-glucan, which may be dispersed in a liquid colloid. In certain embodiments the surfactant molecules are amphilic, i.e., they contain both hydrophobic groups (their "tails") and hydrophilic groups (their "heads"). In certain embodiments the hydrophilic component comprises β-1,6-glucan, optionally modified according to any one or more ways described herein. In certain embodiments a micelle in aqueous solution forms an aggregate with the hydrophilic "head" regions in contact with surrounding solvent, sequestering the hydrophobic tail regions in the micelle center. The micelle may be globular and roughly spherical in shape, but in certain embodiments the micelle is an ellipsoid, cylinder, or bilayer.

In some embodiments the micelle is a polymeric micelle such as those described in U.S. Pub. No. 20020035217. In some embodiments the micelle encapsulates an active agent, e.g. a hydrophobic molecule. Exemplary active agents include anti-infective agents such as anti-bacterial, anti-viral, anti-fungal, anti-parasite agents; chemotherapeutic agents for treatment of cancer; immunostimulatory compound, antigen, adjuvant, etc.

The invention further provides β-1,6-glucan that is modified by conjugating a lipid thereto, wherein the modification in some embodiments allows for creation of a micelle comprising β-1,6-glucan having the lipid attached thereto. The lipid may be a straight chain or branched, optionally substituted, hydrocarbon. In some embodiments the lipid comprises a fatty acid. In some embodiments the lipid, e.g. fatty acid, contains between 4 and 26 or between 4 and 40 carbon atoms.

Also provided by the present invention is a particle comprising β-1,6-glucan covalently or noncovalently linked to a particle comprising or consisting essentially of yeast glucan. Also provided is β-1,6-glucan comprising a reactive moiety able to react with a functional group of a yeast glucan to form a covalent bond. The yeast glucan may comprise β-1,6-glucan, β-1,3-glucan, other glucans, or a combination thereof.

Also provided by the invention is a composition comprising β-1,6-glucan and a biodegradable polymer. In some embodiments the biodegradable polymer comprises biologically active subunits. The term "biodegradable" refers to a material, which is degraded, i.e., broken down into smaller fragments, in the biological environment of the cell or subject in which it is found. In one embodiment, biodegradation involves the degradation of a polymer into its component subunits, via, for example, enzymatic or non-enzymatic hydrolysis, digestion, etc. In one embodiment, biodegradation may involve cleavage of bonds (whether covalent or otherwise) in the polymer backbone. In another embodiment, biodegradation may involve cleavage of a bond (whether covalent or otherwise) internal to a side-chain or one that connects a side chain to the polymer backbone. In some embodiments the degradation products are metabolizable by the subject. In some embodiments the degradation products are usable by the subject for synthesis of larger biomolecules. In some embodiments the degradation products are excreted or otherwise eliminated by the subject. In some embodiments the polymer and/or its degradation products are biocompatible in that they are substantially nontoxic and do not produce an unacceptable inflammatory or immune response when administered or otherwise introduced into the body of a subject in amounts consistent with the present invention.

In some embodiments, a biodegradable polymer encapsulating the glucans of this invention comprise particles of this invention. In some embodiments, such polymers may comprise poly(lactic-co-glycolic)acid (PLGA), hydrophobic bioabsorbable polymers such as polyglycolide, polylactide (D, L, DL), polydioxanones, polyestercarbonates, polyhydroxyalkonates, polycaprolactone (polylactones), polyethylene glycol, hydroxypropylmethyl cellulose phthalate, cellulose acetate phthalate, and the Ludragit R, L, and E series of polymers and copolymer mixtures thereof, and copolymers made from two or more precursors of the above, prepared by any means known in the art, for example, as described in U.S. Pat. Nos. 7,060,299, 6,998,115, 6,048,551, incorporated by reference herein in their entirety.

The term "biologically active agent" includes therapeutic agents that provide a therapeutically desirable effect when administered to an animal (e.g. a mammal, such as a human) in effective amounts, it being understood that not all subjects will benefit from the agent. In some embodiments the polymer is a polyanhydride, which optionally comprises biologically active salicylates and alpha-hydroxy acids. Degradation of the polymer releases said biologically active salicylates and/or alpha-hydroxy acids. In some embodiments the β-1,6-glucan is covalently or noncovalently attached to the biodegradable polymer. Suitable polymers and methods for manufacture thereof are described, e.g. in U.S. Publication No. 20030035787 and 20050053577. In certain embodiments the polymer comprises between 10 and 1000, or between 50 and 500, or about 100 monomers. In one embodiment the polymer is Polyaspirin®. Methods of forming a compound in which a β-1,6-glucan is covalently linked to the polymer will be evident to one of skill in the art. The β-1,6-glucan could be covalently attached to a monomer prior to polymerization or could be to conjugated to a functional group of the polymer following polymerization. In some embodiments the β-1,6-glucan is covalently attached via a linking group. Exemplary linking groups are described in U.S. Pub. No. 20050053577, and others will be evident to one of skill in the art.

In some embodiments the composition comprises a particle comprising β-1,6-glucan and the biodegradable polymer. In some embodiments the particle is coated with or impregnated with β-1,6-glucan. In some embodiments the β-1,6-glucan is covalently attached to the polymer. In some embodiments the composition coats an implant or other medical or surgical device as described elsewhere herein.

Further provided are methods of administering a β-1,6-glucan and a biologically active salicylate or alpha-hydroxy acid to a subject, the method comprising administering a composition comprising β-1,6-glucan and a biodegradable polymer comprising said biologically active salicylates and/or alpha-hydroxy acids to the subject or implanting or introducing a device comprising said polymer and said biologically active salicylates and/or alpha-hydroxy acids into a subject.

In some embodiments, this invention provides low molecular weight glucans, having a molecular weight of less than 100 kDa (e.g. less than 80, 70, 60, 50, 40, 30, 25, 20, or 15 kDa). In some embodiments, this invention provides oligosaccharides e.g. containing 85 or fewer (e.g. 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4) glucose monosaccharide units.

In some embodiments of any of the compositions, particles, coated materials, or devices of the invention comprising β-1,6-glucan, the β-1,6-glucan comprises or consists essentially of a low molecular weight glucan. In some embodiments of any method of the invention in which β-1,6-glucan is utilized, the β-1,6-glucan comprises or consists essentially of a low molecular weight glucan. Optionally at least some of the low molecular weight β-1,6-glucan in any embodiment of the invention is enriched for O-acetylated groups.

A common technique in determining linkage type and structure in glucans is carbon-13 nuclear magnetic resonance spectroscopy ($^{13}$C-NMR). The number and relative intensities of $^{13}$C signals in a given spectrum can be used to determine linkage configurations and positions in glucan polymers. For example, the chemical shifts (signals) of carbon atoms engaged in the glycosidic bond are shifted strongly downfield (up to 9 ppm) compared to the corresponding unlinked carbons.

This invention provides, in some embodiments, a composition comprising β-1-6-glucan, wherein the glucan is conjugated to a solid support. In one embodiment, the solid support is a bead or particle.

In one embodiment, the beads or particles to which glucans are conjugated comprise denatured proteins (e.g. human serum albumin (Benacerraf et al., 1957 Brit. J. Exp. Path, 38:35)), insoluble materials (e.g. carbon black, silica, silicon dioxide, polystyrene, latex), metal oxides (e.g. titanium oxides, iron oxides), and India ink (i.e., suspension of colloidal carbon particles) (described in Reichard and Filkins, 1984, The Reticuloendothelial System; A Comprehensive Treatise, pp. 73-101 (Plenum Press), and references therein), hydrogels, (for example as described in US Patent Publication No. 20050191361), sepharose or agarose beads or microparticles. In some embodiments the beads or microparticles are formed from materials that are biodegradable and non-toxic (e.g. a poly(α-hydroxy acid) such as poly(lactide-co-glycolide), a polyhydroxybutyric acid, a polyorthoester, a polyanhydride, a polycaprolactone, etc.). The beads or particles of the present invention may comprise red blood cells (RBCs) that have been purged of their cytoplasm, known as 'Ghost' RBCs, bacteria (as bacteria are cleared by the RES; see, e.g. Benacerraf and Miescher, 1960, Ann NY Acad Sci, 88:184-195), cell fragments, liposomes, bacteriophages, bacteriophage fragments, and viral capsids devoid of the viral nucleic acids (e.g. hepatitis B virus surface antigen particles), etc.

In one embodiment, conjugation to the particle or solid support is via chemically cross-linking the particle/solid to the glucans of this invention. The chemistry of cross-linking is well known in the art. The nature of the crosslinking reagent used to conjugate the glucan and the solid (e.g. bead or particle) can be any suitable reagent known in the art. It is to be understood that any suitable crosslinking agent may be used with care taken that the activity of the glucan is preserved.

In some embodiments, the glucan is linked to a targeting moiety as further herein described. In some embodiments, the term "conjugate" or "linked" and grammatical forms thereof refer to any association between the indicated molecules. In some embodiments, such linkage is covalent, and in some embodiments, such linkage is non-covalent. In some embodiments, such linkage is direct, and in some embodiments, is via a linker molecule.

In some embodiments such linkage will be via any means known in the art, and as described herein. For example, and in some embodiments, linkage may be via amide formation, urethane, imine or disulfide linkage between the respective molecules, or between a linker moiety with the respective molecules. It is to be understood that there is no limitation with respect to the chemical backbone of the linker molecules. In some embodiments, the linker backbone may be biocompatible, non-immunogenic and/or water soluble. In some embodiments, the linker may comprise poly ethylene glycol (PEG), further comprising active chemical groups which facilitate linkage as herein described.

In some embodiments, other linkers, which may readily be used for such purpose comprise alkanes, polyesters, polyimines, poly-acids, proteins, peptides, DNA, RNA, other glucans, lipids, saccharides, polysaccharides, carbon nanotubes, dendrimers, or solid particles, such as, for example, polymers, metals, salts, inorganic materials, etc.

The particle may be a fragment of a bacteriophage or bacteria.

In certain embodiments the size of the particle is appropriate for ingestion by macrophages, neutrophils, or both. The particle can have any of the compositions described herein. In certain embodiments the invention provides a population of particles, wherein at least 50% of the particles have a size appropriate for ingestion by macrophages, neutrophils, or both. The invention provides populations of particles, wherein at least 50%, 75%, or 90% of the particles fall within a desired size range. In certain embodiments the desired size ranges within ±10%, ±20%, ±30%, ±40%, or ±50% of a given value. The value may be, e.g. 20 nm, 100 nm, 500 nm, 1, 5, 10, 20, 50 microns, etc. The particles in any of these embodiments can have any of the compositions described herein. The population can comprise particles having different compositions, in any ratio. The populations of particles may be used for any of the purposes described herein, and methods for such use are an aspect of this invention.

Cross-linking reagents that can be used include, but are not limited to, p-Azidobenzoyl hydrazide, N-(4-[p-Azidosalicylamido]-butyl)-3'(2'-pyridyldithio)-propionamide, Bis(beta-[4-azidosalicylamido]-ethyl)disulfide, 1,4-bismaleimidyl-2,3-dihydroxybutane, 1,6-Bismaleimidohexane, 1,5-Difluoro-2,4-dinitrobenzene, Dimethyl adipimidate-2HCl, Dimethyl suberimidate-2HCl, Dimethyladipodimidate-2HCl, Dimethyl pimelimidate-2HCl, Disuccinimidyl glutarate, Disuccinimidyl tartrate, 1-Ethyl-3-[3-Dimethylanonopropyl]Carbodiimide Hydrochloride, (N-Hydroxysuccinimidyl)-4-Azidosalicylic acid, Sulfosuccinimdyl 2-[7-azido-4-methyl-coumarin-3-acetamidomethyl-1,3-aminopropionate, N-Succinimidyl-4-iodoacetylaminobenzoate, N-Succinimidyl-3-[2-pyridylthio]propionate, and Succinimidyl 6-[3-(2-pyridylathio)-propionamide]hexanoate (Pierce Chemical Co., Rockford, Ill.) In one embodiment, the glucans are derivatized as described in Nature Methods Vol 2 No. 11, p., 845, 2005, or a similar approach. In one embodiment glucans are derivatized with a moiety that provides a free, reactive primary amine using a reagent such as 2,6-diaminopyridine (DAP). The Schiff base azomethine can be reduced, e.g. by sodium cyanoborohydride to a stable secondary amine. In one embodiment, the derivatized glucan is then reacted with an N-hydroxysuccinimide (NHS) ester, such as NHS-biotin.

Other crosslinking reagents comprise aldehyde, imide, cyano, halogen, carboxyl, activated carboxyl, anhydride and maleimide functional groups. In some embodiments, the cross-linking reagent may comprise heterobifunctional crosslinking reagents such as ABH, M2C2H, MPBH and PDPH (Pierce Chemical Co., Rockford, Ill.). See, e.g. Hermanson, G. T. (1996). Bioconjugate Techniques, Academic Press, Inc., for further discussion of cross-linking methods and reagents.

In another embodiment, conjugation of the glucan to the beads or particles may be via use of beads comprising functional groups which can be conjugated according to methods as disclosed by, e.g. Brumeanu et al. (Genetic Engineering News, Oct. 1, 1995, p. 16).

It is also possible to conjugate the beads/particles/solid/targeting moiety to the glucan by non-covalent means. One convenient way for achieving non-covalent conjugation comprises utilizing antibodies to the glucan, which are covalently or non-covalently attached to the particle, bead, etc. In another embodiment, non-covalent conjugation is achieved using biotin-avidin (where "avidin" should be understood to refer to any form of avidin). For example, avidin-coated or conjugated beads may be contacted with glucan derivatized with a biotin moiety.

In some embodiments, preparation of the conjugated glucans includes purification of the final conjugate substantially free of unconjugated reactants. Purification may be achieved by affinity, gel filtration, hydrophobic chromatography, tangential ultrafiltration, diafiltration or ion exchange chromatography based on the properties of either component of the conjugate. For example, purification may reduce the amount of one or more of the unconjugated reactants (e.g. glucan or solid support) to 10% or less, 5% or less, or 1% or less of the amount of unconjugated reactant that was originally present.

In some embodiments, the invention provides a particle comprising β-1-6-glucan, which in some embodiments, is enriched for O-acetylated groups. In some embodiments, the particle comprises at least 50% β-1-6-glucan by weight. In some embodiments, the β-1-6-glucan is homogeneously distributed in the particle. It is to be understood that the particles comprising β-1-6-glucan of this invention, may in turn encompass any embodiment appropriate thereto, as described herein.

In one embodiment, the conjugated glucan is enriched for O-acetylated groups, and in one embodiment, contains at least 25% by weight O-acetylated glucan, or any related embodiment as herein described. In one embodiment, the glucan is conjugated to a microsphere, which, in one embodiment, has a diameter of about 1-100 microns. In one embodiment, the microsphere has a diameter which ranges from about 10-50 microns. In another embodiment, the microsphere has a diameter which ranges from about 5-40 microns. In another embodiment the diameter ranges from 0.1 to 5 microns. In another embodiment the diameter ranges from 0.5 to 1 micron. In another embodiment, the particle or bead is in the nanometer range, e.g. 100 to 500 nm.

In one embodiment, the term "bead" or "particle" or "solid support" refers to a material, which is spherical. In another embodiment, term "bead" or "particle" or "solid support" refers to a material, which is non-spherical. In one embodiment, non-spherical beads or particles possess a longest axis or longest dimension between any two points on their surface within any of the afore-mentioned ranges. In one embodiment, the dimensions of the particle (e.g. diameter) are selected to promote phagocytosis of the particles by phagocytic cells, such as neutrophils, macrophages or dendritic cells.

In one embodiment, the term "bead" or "particle" or "solid support" refers to any solid or gelled, or sol-gel-based material, to which the glucan can be adhered, of a size and composition, which can be taken up by phagocytic cells.

In one embodiment, the compositions of this invention comprise or methods of this invention make use of beads or particles having dimensions and surface density of glucan (e.g. β-1,6-glucan, optionally enriched for O-acetylated groups), that is efficiently phagocytosed by antigen-presenting cells as compared, e.g. with particles having different dimensions and/or surface density of glucan.

In one embodiment, conjugation to the solid support may be accomplished with a direct linkage via reaction with solid supports comprising a reactive functional group.

Linking chemistries to bind the linker to the β-1-6-glucan and/or to bind the linker to the antibody include, inter alia, amide formation, urethane, imine or disulfide linkage.

The chemical backbone for the linker molecules is not limited. In one embodiment, the backbone is biocompatible, non-immunogenic and water-soluble. In one embodiment, the linker is polyethylene glycol (PEG). Other linkers include, inter alia, alkanes, polyesters, polyimines, poly-acids, proteins, peptides, DNA, RNA, glucans, lipids, saccharides, polysaccharides, carbon nanotubes or dendrimers. In one embodiment, the linker is a solid particle, which may be, inter alia, a polymer, a metal, a salt, a natural material or an inorganic material such as silica.

Linkages via a linker group may be made using any known procedure, for example, the procedures described, for example, in U.S. Pat. No. 6,642,363; 4,882,317; or 4,695,624. A useful type of linkage is an adipic acid linker, which may be formed by coupling a free —NH$_2$ group on an aminated glucan with adipic acid (using, for example, diimide activation), and then coupling a protein to the resulting saccharide-adipic acid intermediate. Another type of linkage is a carbonyl linker, which may be formed by reaction of a free hydroxyl group of a modified glucan with CDI followed by reaction with a protein to form a carbamate linkage. Other linkers include B-propionamido, nitrophenyl-ethylamine, haloacyl halides, glycosidic linkages, 6-aminocaproic acid, ADH, C4 to C12 moieties, etc.

In another embodiment, the invention provides a particle comprising β1-6-glucan. In certain embodiments, the particle consists of at least 10%, 20%, 30%, 40%, 50%, 60%, 70%, 80%, 90%, 95%, 96%, 97%, 98%, or 99% β-1-6-glucan by dry weight. In certain embodiments, the particle consists essentially of β-1-6-glucan. In certain embodiments, the particle consists essentially of β-1-6-glucan, exclusive of any solvent component, such as water. In certain embodiments the β-1-6-glucan is enriched for O-acetylated groups. In certain embodiments the particle contains less than 50%, 40%, 30%, 20%, 10%, or 5% β-1-3 glucan by dry weight. The invention further provides a composition containing any of the aforementioned particles comprising or consisting essentially of β-1-6-glucan, optionally enriched for O-acetylated groups. The composition may further contain a pharmaceutically acceptable carrier or adjuvant. The invention further provides a method of modulating the immune response of a mammalian subject comprising administering any of the afore-mentioned particles, or a composition containing any of the aforementioned particles, to the subject. The particle can be prepared using any method known in the art. The particles can be milled or sieved to achieve a desired size. In certain embodiments the β-1-6-glucan is distributed evenly, or homogeneously, in the particle. In certain embodiments "distributed evenly" means that the β-1-6-glucan is not encapsulated within a different material, does not simply coat the surface of a particle comprised of a different material, or is not covalently or non-covalently attached to the surface of a particle composed of a different material. Instead, in certain embodiments the β-1-6-glucan, optionally mixed with another material, is formed into a particle such that the β-1-6-glucan is located throughout substantially the entire volume of the particle. It will be appreciated that the density of the β-1-6-glucan may vary but will generally vary gradually and continuously throughout the particle rather than abruptly.

In another embodiment, this invention provides a composition comprising a β-1-6-glucan physically associated with a targeting moiety, which in one embodiment specifically interacts with or attracts a phagocytic cell.

According to this aspect and in one embodiment, the term "physically associated" refers to the formation of a covalent linkage. In one embodiment, the term "physically associated" refers to strong non-covalent linkages. In some embodiments, such linkages may be effected by any means known to one skilled in the art, including some exemplified and described hereinbelow. Linking agents may be readily applied for such a purpose, and are commercially available, in some embodiments.

The β-1-6-glucan is linked to a targeting moiety, according to this aspect of the invention, and in an embodiment thereof. Such a targeting moiety may comprise any molecule, which specifically interacts with a desired target, which in one embodiment promotes interaction with a phagocytic cell, or, in some embodiments, attracts or recruits a phagocytic cell.

In some embodiments, the targeting moiety is for a particular phagocytic cell type, or in some embodiments, for a particular phagocytic cell, for example, an infected cell, or in some embodiments, a neoplastic cell or in some embodiments, a preneoplastic cell. In some embodiments, for example, targeting of a virally infected cell may be accomplished via linkage of the glucan with a viral co-receptor. In some embodiments, targeting moieties may include integrins or class II molecules of the MHC, which may be up-regulated on infected cells such as professional antigen-presenting cells.

In some embodiments, targeting of an infected cell results in enhanced therapeutic responses to infection in the subject. For example, and in some embodiments, targeting the infected cell enhances phagocytosis and/or cytotoxic responses to the pathogen, or in some embodiments, enhances complement-mediated lysis of the pathogen. In some embodiments, targeting of the infected cell enhances the immune response to the pathogen.

In some embodiments, the targeting moiety specifically interacts with a neoplastic or pre-neoplastic cell, as described herein, and comprising any embodiment thereof. In some embodiments, the use of a β-1-6-glucan linked to a targeting moiety, which targets a neoplastic or preneoplastic cell, promotes host anticancer responses. In some embodiments, such targeting promotes tumor cell lysis, or, in some embodiments, enhances host antitumor responses.

In some embodiments, and without limitation, use of the glucans, β-1-6-glucan linked to a targeting moiety and/or compositions of this invention are suitable, inter alia, for treating tumors that are resistant to complement-mediated lysis.

In some embodiments, and without limitation, use of the glucans, β-1-6-glucan linked to a targeting moiety and/or compositions of this invention target the polysaccharide to an antigen expressed specifically on cancer cells and thereby enhance complement-mediated lysis of the cells.

In some embodiments, targeting to neoplastic or pre-neoplastic cells or tissue, or tumors can be accomplished by targeting a tumor antigen, as herein described. In some embodiments, such cells may express adrenomedullin receptors (ADMR), a calcitonin receptor-like receptor (CRLR), CD117 or any combination of tumor-associated antigens, as herein described.

In one embodiment, the targeting moiety is a peptide which binds to an underglycosylated mucin-1 protein. Mucin-1 (MUC-1) is a transmembrane molecule, which is overexpressed on the cell surface and in intracellular compartments of almost all human epithelial cell adenocarcinomas, including more than 90% of human breast cancers, ovarian, pancreatic, colorectal, lung, prostate, colon and gastric carcinomas. Expression in an underglycosylated form, which exposes an immunogenic epitope that is normally masked, has been demonstrated in non-epithelial cancer cell lines (for example, astrocytoma, melanoma, and neuroblastoma), as well as in hematological malignancies such as multiple myeloma and some B-cell non-Hodgkin lymphomas, constituting more than 50% of all cancers in humans.

According to this aspect, and in one embodiment, by targeting cells expressing adrenomedullin receptors or mucin-1 expressing cells with the linked glucans of this invention, lung, pancreas, ovary, breast and other related cancers may be treated. In some embodiments, by targeting cells expressing CRLR and/or CD117, with the linked glucans of this invention, vascular tumors, gliomas, and/or other related cancers may be treated.

In some embodiments, reference herein to a targeting moiety is to be understood to encompass an antibody, or fragment thereof as described herein, a naturally occurring peptide ligand for the referenced receptor, or a modified form thereof, such as, for example, a truncation product. In some embodiments, reference herein to a targeting moiety is to be understood to encompass artificial peptides, small molecules, and the like.

In some embodiments, many monoclonal antibodies (mAb) are used in various therapies, which comprise for example, Alemtuzumab (Campath), Bevacizumab (Avastin), Cetuximab (Erbitux), Gemtuzumab (Mylotarg), Ibritumomab (Zevalin), Panitumumab (Vectibix), Rituximab (Rituxan), Tositumomab (Bexxar), Trastuzumab (Herceptin), Palivizumab (Synagis). Any of these mAbs may be linked to a glucan of this invention, or comprise a composition as herein described, and comprise a targeting moiety or immune stimulating compound for use in any of the methods as described herein. It is to be understood that any monoclonal antibody or other targeting moiety, or immune stimulating compound may be linked to the glucans of this invention, or comprise compositions of this invention, and such materials are to be considered as part of this invention, and encompassed for use in any methods of this invention.

In some embodiments, this invention provides for the use of the glucans, β-1-6-glucans linked to a targeting moiety and/or compositions of this invention (as described herein, including any embodiment thereof) as a means to determine neoplastic or preneoplastic cell or tissue responsiveness to a treatment regimen. In some embodiments, such method includes obtaining a tumor sample from the subject or biopsy material containing the neoploastic or preneoplastic cells and assessing the sensitivity or resistance of the cells to in vitro lysis and/or determining the level of expression and/or secretion of an endogenous complement control protein.

In some embodiments the tumor cell expresses or overexpresses (e.g. relative to a normal cell of the cell type or tissue of origin of that cell) an endogenous complement control protein such as complement receptor 1 (CR1 or CD35), decay-accelerating factor (DAF or CD55), membrane cofactor protein (MCP of CD46), complement factor H (fH) (or FHL-1) and/or C4b-binding protein (C4BP).

In some embodiments, this invention provides for the use of the glucans, β-1-6-glucans linked to a targeting moiety and/or compositions of this invention (as described herein, including any embodiment thereof) as a means to target pathological vasculature, such as, for example, atherosclerotic vasculature, or in some embodiments, targeting pathologic neo-vasculature such as tumor-associated neovasculature for purposes of enhancing elimination of such vasculature.

According to this aspect of the invention and in some embodiments, the targeting moiety comprises, inter alia, an antibody or antibody fragment or ligand specifically interacting with a component of such vasculature, for example, an agent specifically interacting with VEGF, tissue factor, a clotting factor, vascular cell adhesion molecules, integrins, selectins, or any other marker expressed on or at the surface of endothelial cells.

In one embodiment, the targeting moiety is a peptide, an antibody, an antibody fragment, a receptor, Protein A, Protein G, Protein L, biotin, avidin, streptavidin, a metal ion chelate, an enzyme cofactor, a nucleic acid or a ligand.

In some embodiments, such a targeting moiety may comprise an antibody or antibody fragment. In some embodiments, such an antibody or antibody fragment will specifically interact with a desired target, as herein described, for example, by interacting with a phagocyte, such that linkage of said antibody or fragment with the glucan does not inhibit such interaction.

In some embodiments, the term "antibody" refers to intact molecules as well as functional fragments thereof, such as Fab, F(ab')2, and Fv that are capable of specifically interacting with a desired target as described herein, for example, binding to phagocytic cells. In some embodiments, the antibody fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

In some embodiments, the antibody fragments may be prepared by proteolytic hydrolysis of the antibody or by expression in E. coli or mammalian cells (e.g. Chinese hamster ovary cell culture or other protein expression systems) of DNA encoding the fragment.

Antibody fragments can, in some embodiments, be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., Proc. Nat'l Acad. Sci. USA 69:2659-62, 1972.

Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

In some embodiments, the antibodies or fragments as described herein may comprise "humanized forms" of antibodies. In some embodiments, the term "humanized forms of antibodies" refers to non-human (e.g. murine) antibodies, which are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g. mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

In one embodiment, the targeting moiety is an antibody or fragment thereof, specifically recognized by a neutrophil, for example, and antibody specifically recognizing L-selectin, β2-integrins, complement receptor 1 (CR-1), decay-accelerating factor (DAF), C5a receptor, intercellular adhesion molecule-1 (ICAM-1), ICAM-3 and others as will be appreciated by one skilled in the art.

In some embodiments, phagocytic cells are targeted or engaged via a molecule interacting with Fc receptors, chemokine receptors, CD40, CD80, CD86, MHC class II molecules, CD69, ADAMS, CD14, CD163, CD33, CD63, CD68, CD74, CHIT1, CHST10, CSF1R, DPP4, FABP4, FCGR1A, ICAM2, IL1R2, ITGA1, ITGA2, S100A8, TNFRSF8, and others as will be appreciated by one skilled in the art.

In another embodiment, the targeting moiety may be any appropriate moiety, for example, aptamers, naturally occurring or artificial ligands, or engineered binding proteins may comprise the targeting moieties as described herein, and their physical association with a glucan as herein described can be readily accomplished by any number of means known in the art, including, for example, the methods described hereinbelow, or variations thereof, to suit the particular nature of the targeting moiety chosen.

In one embodiment, the targeting moiety enhances attachment to the cell, or, in another embodiment, enhances homing to the cell. In one embodiment, the targeting moiety enhances attachment following supply of an energy source. In one embodiment, the targeting moiety is chemically attached to the glucan via a chemical cross-linking group, or in another embodiment, forms a stable association with the glucan, or, in another embodiment, forms an association with the glucan, which dissociates following changes in environmental conditions, such as, for example, salt concentration or pH.

In one embodiment, the targeting moiety may be an antibody, which specifically recognizes a molecule of interest, such as a protein or nucleic acid. In another embodiment, the antibody may specifically recognize a reporter molecule attached to a molecule of interest. In another embodiment, the targeting moiety may be an antibody fragment, Protein A, Protein G, Protein L, biotin, avidin, streptavidin, a metal ion chelate, an enzyme cofactor, or a nucleic acid. In another embodiment, the targeting moiety may be a receptor, which binds to a cognate ligand of interest, or associated with a cell or molecule of interest, or in another embodiment, the targeting moiety may be a ligand which is used to attach to a cell via interaction with its cognate receptor.

Linking the targeting moiety to the glucan of this invention may be accomplished by any means known in the art, for example as described further herein in Example 7, or for example, as described in U.S. Pat. No. 5,965,714, or United States Patent Publication No. 20070141084, or Schneerson et al., Proc Natl Acad Sci USA. 2003 Jul. 22; 100 (15):8945-50, Lees et al., Vaccine. 1996 February; 14 (3):190-8, or via the use of a cross-linking agent as described herein, or other methods, as will be appreciated by one skilled in the art.

In some embodiments, glycosylated antibodies are used and the β-1,6-glucan is linked to the glycosylated residue of the antibody, or in another embodiment, linkages may be multiple and involve multiple sites on the antibody, or targeting moiety, as will be understood by one skilled in the art.

In some embodiments, linking the glucan to a targeting moiety results in enhanced phagocytosis and/or killing of the targeted cell or organism. In some embodiments, such lysis may be mediated by any professional antigen presenting cell or killer cell, such as, for example, neutrophils, macrophages, dendritic cells, natural killer cells, cytotoxic T lymphocytes, and others.

In some embodiments, any O-acetylated glucan may be physically associated with a targeting moiety, and comprise the glucans or compositions of this invention, representing an embodiment thereof. Use of such O-acetylated glucans, for example β-1,3-glucans which have been O-acetylated, for modulating immune responses, treating cancer or precancerous lesions, promoting resolution of infection, or any method as herein described is to be considered as part of this invention.

In some embodiments, any of the glucan preparations of this invention may be linked to a labeling agent, such that detection of the glucan is readily accomplished. In one embodiment, the term "a labeling agent" refers to a molecule which renders readily detectable that which is contacted with a labeling agent. In one embodiment, the labeling agent is a marker polypeptide. The marker polypeptide may comprise, for example, green fluorescent protein (GFP), DS-Red (red fluorescent protein), secreted alkaline phosphatase (SEAP), beta-galactosidase, luciferase, or any number of other reporter proteins known to one skilled in the art. In another embodiment, the labeling agent may be conjugated to another molecule which provides greater specificity for the target to be labeled. For example, and in one embodiment, the labeling agent is a fluorochrome conjugated to an antibody which specifically binds to a given target molecule, or in another embodiment, which specifically binds another antibody bound to a target molecule, such as will be readily appreciated by one skilled in the art. In some embodiments, the glucan linked to an antibody incorporates a fluorochrome in the antibody as will be appreciated by one skilled in the art.

In one embodiment, the glucan is enriched for O-acetylated groups, and in one embodiment, the glucan contains at least 25% by weight O-acetylated glucan. In another embodiment, the glucan is isolated or derived from a lichen or a yeast, which in one embodiment is Umbilicariaceae. In one embodiment, the glucan is chemically synthesized or acetylated. In another embodiment, the composition further comprises an adjuvant, an antigen, an immuno-modulatory compound, or a combination thereof. In another embodiment, the phagocytic cell is a professional antigen-presenting cell. In another embodiment, the phagocytic cell is a neutrophil.

In one embodiment, the targeting moiety is an antibody or antibody fragment.

The invention provides a coated material comprising (a) a substrate; and (b) a compound or composition comprising β-1-6-glucan. In certain embodiments the β-1-6-glucan is enriched for O-acetylated glucan. In certain embodiments, the coated material is in the form of, or is a component of, an implant or other surgical or medical device. In certain embodiments the coated material is a coated material described in provisional patent application U.S. Ser. No. 60/817,075, filed Jun. 29, 2006, entitled "Coating of Devices with Effector Compounds", wherein the "effector compound" is or comprises β-1-6-glucan.

The invention provides implants and surgical or medical devices comprising a coated material of the invention. As used herein, the term "medical device" encompasses implants and any device used in the surgical or medical management of a subject, wherein the device is contacted with or introduced into the body of the subject and typically remains in contact with, or at least in part within the body for at least a period of 2 hours, e.g. at least 4, 8, 12, or 24 hours. In certain embodiments, the term "device" refers to a complete device or any part or component thereof. For example, in many applications, a part for a device will be treated in accordance with the present invention and then later assembled with other parts to form a complete device.

In certain embodiments the period is between 1 day and 1 week, 1-4 weeks, 4-8 weeks, 1-6 months, 6-12 months, or longer. In certain embodiments the device is intended to remain in contact with, or within the body for the remainder of the subject's life (unless the device fails or needs to be removed, e.g. as a result of infection). In certain embodiments the invention provides implants and surgical or medical devices, such as catheters, indwelling intravenous or arterial lines, stents, and grafts, coated with or otherwise constructed to contain and/or release any of the compounds or compositions disclosed herein comprising β-1-6-glucan. Optionally the β-1-6-glucan is enriched for O-acetylated groups. In certain embodiments the device coated with or otherwise containing β-1-6-glucan is more resistant to biofilm formation (e.g. by a fungus or bacterium) than an otherwise identical device not coated with or containing the compound or composition. In certain embodiments the implant or other device is as described in provisional patent application U.S. Ser. No. 60/817,075, filed Jun. 29, 2006, entitled "Coating of Devices with Effector Compounds" wherein the effector compound is or comprises β-1-6-glucan.

In certain embodiments the coated material, implant or other device is manufactured as described in provisional patent application U.S. Ser. No. 60/817,075, filed Jun. 29, 2006, entitled "Coating of Devices with Effector Compounds" wherein the effector compound is or comprises β-1-6-glucan.

In one embodiment, the β-1-6-glucan is released slowly, over a course of time (e.g. over 1 day-1 week, 1-4 weeks, 4-12 weeks, 12-24 weeks, 24-36 weeks, 36-48 weeks, etc.). In certain embodiments, by the end of the time period release has substantially ceased. In certain embodiments, at the end of the time period the release rate is less than about 5% of the peak rate of release or less than 5% of the average rate of release during the time period, and/or less than about 5, 10, or 20% of the compound remains associated with the substrate. In other embodiments, the β-1-6-glucan is rapidly released, e.g. at least about 50% of the β-1-6-glucan is released during the first 24 hours. In certain embodiments release is minimal over a time period of interest, e.g. 1 day-1 week, 1-4 weeks, 4-12 weeks, 12-24 weeks, 24-36 weeks, 36-48 weeks, etc.). In certain embodiments at least 50, 60, 70, 80, 90, 95% of more of the β-1-6-glucan remains associated with the substrate at the end of a time period of interest. Release can be measured in vitro, e.g. under conditions of salt concentration, pH, and temperature that approximate physiological conditions in the body of a mammalian subject and/or in vivo. In certain embodiments, the rate of release is controllable, e.g. by appropriate selection of the components of a coating layer and/or their concentration. In certain embodiments the thickness of a coating layer is selected to achieve release over a desired duration. For example, a device having a coating layer of an appropriate thickness or composition may be selected to provide release for the expected duration of use, e.g. the time during which the device is expected to be in intermittent or continuous contact with the subject's body.

Any of the coated materials, implants, or other devices disclosed herein may comprise a β-1-6-glucan and any one or more therapeutic agents useful in treating a medical condition of the subject. "Medical condition" encompasses any acquired or inherited disease, disorder, or injury, etc., for which medical and/or surgical intervention is warranted.

Exemplary inventive implants and other surgical or medical devices include cardiovascular devices (e.g. implantable venous catheters, venous ports, tunneled venous catheters, chronic infusion lines or ports, including hepatic artery infusion catheters, pacemaker wires, implantable defibrillators); neurologic/neurosurgical devices (e.g. ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g. chronic indwelling catheters, feeding tubes, portosystemic shunts, shunts for ascites, peritoneal implants for drug delivery, peritoneal dialysis catheters, implantable meshes for hernias, suspensions or solid implants to prevent surgical adhesions, including meshes); genitourinary devices (e.g. uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, temporary or chronic indwelling catheters, bladder augmentations, or wraps or splints for vasovasostomy); phthalmonlogic implants (e.g. Molteno implants and other implants for neovascular glaucoma or other eye disorders, drug eluting contact lenses for pterygiums, splints for failed dacrocystalrhinostomy, drug eluting contact lenses (e.g. for corneal neovascularity), implants for diabetic retinopathy, drug eluting contact lenses for high risk corneal transplants); otolaryngology devices (e.g. ossicular implants, Eustachian tube splints or stents for glue ear or chronic otitis); plastic surgery implants, and orthopedic implants (e.g. spinal rods, screws, orthopedic prostheses). Other implantable devices of interest herein include pumps, e.g. for delivery of insulin, pain medications, etc. The pump may be an intrathecal pump. Also encompassed is any type of prosthesis, e.g. any substitute for a missing body part. Additionally encompassed are materials useful for sutures.

In certain embodiments the implant or other medical or surgical device is listed in Hunter, T. B. and Taljanovic, M. S., Glossary of Medical Devices and Procedures: Abbreviations, Acronyms, and Definitions *Radiographics.* 23:195-213, 2003.), which provides a nonlimiting set of definitions commonly accepted in the art.

In certain embodiments the device comprises a tube-shaped structure having a lumen, wherein the wall of the structure has an inner and an outer surface, either or both of which is coated with or otherwise adapted to comprise and, optionally, release a compound or composition disclosed herein comprising β-1,6-glucan.

Implants and other surgical or medical devices may be coated with (or otherwise adapted to comprise and, optionally, release) compositions of the present invention in a variety of manners, including for example: (a) by affixing to the implant or device a compound or composition (e.g. by spraying the implant or device with a composition comprising a compound or composition of the invention, by dipping the implant or device into a solution comprising the compound or composition of the invention, or by other covalent or noncovalent means); (b) by coating the implant or device with a substance such as a hydrogel which will in turn absorb the inventive compound or composition; (c) by interweaving a compound- or composition-coated thread or other substrate into the implant or device; (d) by inserting the implant or device into a sleeve or mesh which is comprised of or coated with a compound or composition disclosed herein; (e) constructing the implant or device itself with a compound or composition disclosed herein; or (f) by otherwise adapting the implant or device to release the compound or composition.

In one embodiment the term "coated" refers to the physical attachment, or, in another embodiment, association of a gel, film, foam, particle and/or composition comprising β-1,6-glucan with at least a portion of a surface of a material whose "coating" is desired. In one embodiment, such coating will comprise less than 1% of an exposed surface of the material, or in another embodiment, from 1-10%, or in another embodiment, from 1-25%, or in another embodiment, from 1-50%, or in another embodiment, from 1-75%, or in another embodiment, from 1-100% of at least one surface of the material.

In one embodiment, application of such "coating" will be in a pattern, or on specific regions of the material to suit a particular purpose. For example, and in some embodiments, a tube-shaped device such as a catheter may comprise coating of one material on the lumenally exposed surface of the tube, for example, a coating comprising an anti-inflammatory or anti-proliferative compound, and, in some embodiments, the tube-shaped device may be coated with a different material, for example, a coating comprising a □-1,6-glucan which, in one embodiment, inhibits biofilm formation. In one embodiment, the coating of a material will be on at least one surface of the material, or in another embodiment, on two or more surfaces of the material, or in another embodiment, on every exposed surface of the material, or in another embodiment, on any surface of the material.

In some embodiments, the term "coated material" applies not only to a surface coating of the material, but is to be understood as encompassing embedding and/or impregnating the material, in whole, or in some embodiments, in part, with the gels, films, foams, particles and/or compositions described herein comprising β-1,6-glucan. In some embodiments, the embedding and/or impregnating the material may be according to a desired pattern and/or design, to suit a particular purpose or application. In some embodiments, multiple coatings may be impregnated or embedded in the material, each of which may be applied according to a particular pattern or design, which may be the same, or in another embodiment, different than the patterning of a first coating.

In some embodiments, the embedding and/or impregnating may be to a particular surface of a material, in a particular pattern and/or design, to suit a particular purpose or application. In some embodiments, the embedding and/or impregnating of the material may be to two or more surfaces of the material in the particular pattern and/or design, or such pattern and/or design may vary as a function of the surface to which the material is being embedded and/or impregnated within.

The devices are made of any of a variety of different materials, as appropriate for their intended use. In certain embodiments the devices of this invention can be made at least in part from any suitable thermoplastic or thermosensitive (e.g. thermosetting) polymer. Suitable polymers include, for instance, silicones and urethanes (e.g. polyurethane). In one embodiment, the substrate, material or device can be made at least in part from polyvinyl chloride. In certain embodiments the device is formed at least in part from polyethylene. One of skill in the art will appreciate that these materials are commonly used for tubular devices such as catheters.

In certain embodiments, the compound or composition comprising adheres sufficiently to the implant or other device during storage and at the time of introduction to the body so that the device withstands routine handling (e.g. during insertion) and storage without significant loss of the compound or composition, e.g. with loss not exceeding 10%, 20%, or 30% of the compound or composition. In certain embodiments the compound or composition does not significantly degrade during storage, prior to insertion, or when warmed to body temperature after insertion inside the body (if this is to be performed). In certain embodiments of the invention the inventive implant or device provides a uniform, predictable, prolonged release of the inventive compound or composition into the fluid or tissue surrounding the implant or device once it has been deployed. In certain embodiments, e.g. for vascular stents or other devices that may be exposed to blood, the composition or compound and materials used to form a coating do not render the surface thrombogenic (causing blood clots to form), or cause significant turbulence in blood flow (more than would be expected in the case if the device was uncoated or its surface did not comprise a compound or composition disclosed herein).

In some embodiments, the term "gel" encompasses its ordinary meaning in the art. In one embodiment, the term "gel" refers to a composition comprising a polymer having a fluidity at room temperature between that of a liquid and a solid. In some embodiments, the term "gel" refers to a solid or semisolid colloid system formed of a solid continuous phase and a liquid phase (either discontinuous or continuous or mixed), which, in some embodiments, can be identified by its outward gelatinous appearance, and/or exhibits properties of a solid such as plasticity, elasticity, or rigidity. In some embodiments, the liquid phase can be a 'dispersed' phase, or in other embodiments, continuous. In some embodiments, the gelling component (solid phase) is lipophilic and present in concentrations of less than 10, or in another embodiment, 15, or in another embodiment 20, or in another embodiment, 25, or in another embodiment, 30, or in another embodiment, 40 percent. In some embodiments, the term "gel" may encompass a silica gel, an aluminosilicate gel or other materials, which are primarily solid and/or particulate, microspheroidal, spheroidal, etc., or described with descriptive properties, terms, or expressions which indicates destruction of the two-phase system, such as, pore volume, pore diameter, surface area. In one embodiment, the gel is a hydrogel, which, in certain embodiments comprises at least 70, 80, 90, 95, 98% or more water by weight. In another embodiment, the gel comprises polymers dispersed in solvents other than water or aqueous solutions.

In some embodiments, the term "foam" encompasses its ordinary meaning in the art. In some embodiments, the term "foam" refers to a colloidal suspension of a gas in a liquid. In one embodiment, the term "foam" refers to a composition comprising an internal phase of gas in an external phase of a liquid or solid. In a liquid foam, in some embodiments, a colloidal adsorptive agent forms a film that bounds a gas bubble, with the colloidal dimension in the foam affecting the thickness of the film, not the size of the bubble.

In some embodiments, the term "film" encompasses its ordinary meaning in the art. In one embodiment, the term "film" refers to a layer of material whose dimension is restricted in one dimension. In some embodiments, the average thickness of the film is between 10 µm and 100 µm. In some embodiments, the average thickness of the film is between 1 µm and 10 µm. The thickness of the film can vary or be substantially uniform (e.g. varying by less than about 1, 5, or 10% over a surface in various embodiments).

The invention encompasses precursors to the coated material, e.g. compositions comprising a β-1-6-glucan and a precursor material that can be used to form a coating layer when applied to a substrate or can be used to impregnate a substrate. Optionally the composition comprises a solvent, e.g. one that evaporates to allow formation of a coating layer. In some embodiments the solvent is an aqueous solvent. In some embodiments the solvent is an organic solvent. In some embodiments, the solvent is polar, or slightly polar. In some embodiments, the solvent is non-polar, or essentially non-polar. Suitable solvents may include, inter alia, dimethylsulfoxide (DMSO), acetone, alcohols, methylethyl ketone, toluene, xylene, N,N-dimethyl formamide (DMF), tetrahydrofuran and the like. In some embodiments, the solvent is water.

Also provided are processes for preparing the coated material, implant, or other device of the invention.

The coated substrates, materials and/or devices of this invention may comprise metallic, ceramic, or polymeric materials, or a combination thereof. The substrates, materials and/or devices may have a variety of physical properties. For example, they may be flexible such that they readily conform or bend to adopt a desired shape or configuration under conditions of use, or they may be rigid such that significant force is required to cause an alteration in shape. In some embodiments the device maintains its shape when supported at only one point or end. The surface could be substantially smooth or could be rough and/or comprise crevices.

In some embodiments, the metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646.

In some embodiments, the ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used. Any of these materials may be used to form a substrate or a part of a device of this invention, and may be coated with the gels, foams, films, or other compositions comprising a β-1,6-glucan, as herein described.

Also provided by the present invention are methods of using the devices. The devices may be used in any manner in which conventional counterparts (e.g. counterparts not comprising and/or coated with a compound or composition disclosed herein) are used, such methods being known in the art.

Also provided by the present invention are methods of delivering a compound or composition disclosed herein comprising a β-1,6-glucan to a subject, wherein the method comprises implanting or introducing a coated material or device comprising a compound or composition of the invention into the body of the subject.

In another embodiment, any of the compositions of the invention comprises an adjuvant, an antigen, an immunomodulatory compound, or a combination thereof.

In one embodiment, this invention provides for the combined use of, or compositions comprising β-glucans and an adjuvant. In some embodiments, the adjuvant may include, but is not limited to: (A) aluminium compounds (e.g. aluminium hydroxide, aluminium phosphate, aluminium hydroxyphosphate, oxyhydroxide, orthophosphate, sulphate, etc. [e.g. see chapters 8 & 9 of ref. 96]), or mixtures of different aluminium compounds, with the compounds taking any suitable form (e.g. gel, crystalline, amorphous, etc.), and with adsorption being preferred; (B) MF59 (5% Squalene, 0.5% Tween 80, and 0.5% Span 85, formulated into submicron particles using a microfluidizer); (C) liposomes; (D) ISCOMs, which may be devoid of additional detergent; (E) SAF, containing 10% Squalane, 0.4% Tween 80, 5% pluronic-block polymer L121, and thr-MDP, either micro fluidized into a submicron emulsion or vortexed to generate a larger particle size emulsion; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21, also known as Stimulon™; (H) chitosan; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc.; (K) monophosphoryl lipid A (MPL) or 3-O-deacylated MPL (3dMPL)]; (L) combinations of 3dMPL with, for example, QS21 and/or oil-in-water emulsions; (M) oligonucleotides comprising CpG motifs] i.e. containing at least one CG dinucleotide, with 5-methylcytosine optionally being used in place of cytosine; (N) a polyoxyethylene ether or a polyoxyethylene ester; (O) a polyoxyethylene sorbitan ester surfactant in combination with an octoxynol or a polyoxyethylene alkyl ether or ester surfactant in combination with at least one additional nonionic surfactant such as an octoxynol; (P) an immuno-stimulatory oligonucleotide (e.g. a CpG oligonucleotide) and a saponin; (Q) an immuno-stimulant and a particle of metal salt; (R) a saponin and an oil-in-water emulsion; (S) a saponin (e.g. QS21)+3dMPL+IL12 (optionally+a sterol); (T) *E. coli* heat-labile enterotoxin ("LT"), or detoxified mutants thereof, such as the K63 or R72 mutants; (U) cholera toxin ("CT"), or diphtheria toxin ("DT") or detoxified mutants of either; (V) double-stranded RNA; (W) monophosphoryl lipid A mimics, such as aminoalkyl glucosaminide phosphate derivatives e.g. RC-529]; (X) polyphosphazene (PCPP); or (Y) a bioadhesive such as esterified hyaluronic acid microspheres or a mucoadhesive such as crosslinked derivatives of poly(acrylic acid), polyvinyl alcohol, polyvinyl pyrollidone, polysaccharides and carboxymethylcellulose.

Muramyl peptides include N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)ethylamine MTP-PE), etc.

In another embodiment, this invention provides for the combined use of, or compositions comprising β-glucans and an antigen.

In various embodiments, the antigen may be any molecule recognized by the immune system of the subject as foreign. For example, the antigen may be any foreign molecule, such as a protein (including a modified protein such as a glycoprotein, a mucoprotein, etc.), a nucleic acid, a carbohydrate, a proteoglycan, a lipid, a mucin molecule, or other similar molecule, including any combination thereof. The antigen may, in another embodiment, be a cell or a part thereof, for example, a cell surface molecule. In another embodiment, the antigen may derive from an infectious virus, bacteria, fungi, or other organism (e.g. protists), or part thereof. These infectious organisms may be active, in one embodiment or inactive, in another embodiment, which may be accomplished, for example, through exposure to heat or removal of at least one protein or gene required for replication of the organism. In one embodiment, the antigenic protein or peptide is isolated, or in another embodiment, synthesized.

In one embodiment, the term "antigen" refers to a substance such as a protein, peptide, or any fragment which stimulates or enhances an immune response, following exposure to or contact with the antigen. In one embodiment, the antigen is a "danger" signal interpreted by the immune system of a subject as to initiate or enhance an immune response as a consequence of the signal. In another embodiment, the antigen represents the host's ability to distinguish the presence of a molecule which is "non-self".

In one embodiment, the antigen is derived from a pathogen, an infected cell, a neoplastic or preneoplastic cell. In another embodiment, the antigen is an autoantigen, or a molecule which initiates or enhances an autoimmune response.

In one embodiment, the antigen is derived from a parasitic agent, which resides intracellularly during at least some stages of its life cycle. The intracellular parasites contemplated include for example, protozoa. Protozoa, which infect cells, include: parasites of the genus *Plasmodium* (e.g. *Plasmodium falciparum, P. Vivax, P. ovale* and *P. malariae*), *Trypanosoma, Toxoplasma, Leishmania, Schistosoma*, and *Cryptosporidium*. In another embodiment the parasitic agent resides extracellularly during at least part of its life cycle. Examples include nematodes, trematodes (flukes), and cestodes. In some embodiments, the antigen is derived from byproducts of infection with the protozoa described, for example, egg antigens of the *Schistosoma*, antigens uniquely expressed from *Toxoplasma* cysts, and others, as will be appreciated by one skilled in the art.

In one embodiment, the antigen is derived from a diseased and/or abnormal cell. The diseased or abnormal cells contemplated include: infected cells, neoplastic cells, pre-neoplastic cells, inflammatory foci, benign tumors or polyps, cafe au lait spots, leukoplakia, other skin moles, self-reactive cells, including T and/or NK cells, etc In one embodiment, the antigen is derived from an infectious virus including, inter alia, Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. Ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arenaviridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxviridae (variola viruses, vaccinia viruses, pox viruses); and Iridoviridae (e.g. African swine fever virus); and unclassified viruses (e.g. the etiological agents of spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

In one embodiment, the antigen is derived from bacteria including, inter alia, *Helicobacter pylori*, *Borellia burgdorferi*, *Legionella pneumophilia*, *Mycobacteria* sps (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (*viridans* group), *Streptococcus faecalis*, *Streptococcus bovis*, *Streptococcus* (*anaerobic* sps.), *Streptococcus pneumoniae*, pathogenic *Campylobacter* sp., *Enterococcus* sp., *Chlamydia* sp., *Haemophilus influenzae*, *Bacillus antracis*, *corynebacterium diphtheriae*, *corynebacterium* sp., *Erysipelothrix rhusiopathiae*, *Clostridium perfringens*, *Clostridium tetani*, *Enterobacter aerogenes*, *Klebsiella pneumoniae*, *Pasturella multocida*, *Bacteroides* sp., *Fusobacterium nucleatum*, *Streptobacillus nzoniliformis*, *Treponema pallidium*, *Treponema pertenue*, *Leptospira*, *Actinomyces israelli* and *Francisella tularensis*.

In one embodiment, the antigen is derived from fungi, including, inter alia, *Absidia*, such as *Absidia corymbifera*, *Ajellomyces*, such as *Ajellomyces capsulatus*, *Ajellomyces dermatitidis*, *Arthroderma*, such as *Arthroderma benhamiae*, *Arthroderma fulvum*, *Arthroderma gypseum*, *Arthroderma incurvatum*, *Arthroderma otae*, *Arthroderma vanbreuseghemii*, *Aspergillus*, such as *Aspergillus flavus*, *Aspergillus fumigatus*, *Aspergillus niger*, *Blastomyces*, such as *Blastomyces dermatitidis*, *Candida*, such as *Candida albicans*, *Candida glabrata*, *Candida guilliermondii*, *Candida krusei*, *Candida parapsilosis*, *Candida tropicalis*, *Candida pelliculosa*, *Cladophialophora*, such as *Cladophialophora carrionii*, *Coccidioides*, such as *Coccidioides immitis*, *Cryptococcus*, such as *Cryptococcus neoformans*, *Cunninghamella*, *Epidermophyton*, such as *Epidermophyton floccosum*, *Exophiala*, such *Exophiala dermatitidis*, *Filobasidiella*, such as *Filobasidiella neoformans*, *Fonsecaea*, such as *Fonsecaea pedrosoi*, *Fusarium*, such as *Fusarium solani*, *Geotrichum*, such as *Geotrichum candidum*, *Histoplasma*, such as *Histoplasma capsulatum*, *Hortaea*, such as *Hortaea werneckii*, *Issatschenkia*, such as *Issatschenkia orientalis*, *Madurella*, such *Madurella grisae*, *Malassezia*, such as *Malassezia furfur*, *Malassezia globosa*, *Malassezia obtuse*, *Malassezia pachydermatis*, *Malassezia restricta*, *Malassezia slooffiae*, *Malassezia sympodialis*, *Microsporum*, such as *Microsporum canis*, *Microsporum fulvum*, *Microsporum gypseum*, *Mucor*, such as *Mucor circinelloides*, *Nectria*, such as *Nectria haematococca*, *Paecilomyces*, such as *Paecilomyces variotii*, *Paracoccidioides*, such as *Paracoccidioides brasiliensis*, *Penicillium*, such as *Penicillium marneffei*, *Pichia*, such as *Pichia anomala*, *Pichia guilliermondii*, *Pneumocystis*, such as *Pneumocystis carinii*, *Pseudallescheria*, such as *Pseudallescheria boydii*, *Rhizopus*, such as *Rhizopus oryzae*, *Rhodotorula*, such as *Rhodotorula rubra*, *Scedosporium*, such as *Scedosporium apiospermum*, *Schizophyllum*, such as *Schizophyllum commune*, *Sporothrix*, such as *Sporothrix schenckii*, *Trichophyton*, such as *Trichophyton mentagrophytes*, *Trichophyton rubrum*, *Trichophyton verrucosum*, *Trichophyton violaceum*, *Trichosporon*, such as *Trichosporon asahii*, *Trichosporon cutaneum*, *Trichosporon inkin*, *Trichosporon mucoides*, or others.

In one embodiment, the pathogenic fungus infects human hosts. In one embodiment the pathogenic fungus infects non-human animals.

In some embodiments, the compositions and methods of this invention allow for the combined use of multiple antigens from the same source, multiple antigens from the same class of organism, multiple antigens from different classes of organisms, or any combination thereof.

In another embodiment, this invention provides a method of treating, delaying progression of, or reducing the incidence or severity of an infection in a subject, said method comprising administering to said subject a composition comprising purified β-1-6-glucan. In certain embodiments of the invention the infection is one due to a pathogenic fungus. In certain embodiments of the invention the infection is one due to a pathogenic bacterium, virus, or parasite. In certain embodiments of the invention the subject receives, in addition to a composition of this invention, any agent known in the art to be useful for treating or preventing an infection from which the subject is at risk from which the subject suffers. Thus, in one embodiment, the method comprises administering to a subject (i) a composition of this invention comprising β-1-6-glucan; and (ii) a known anti-fungal, anti-bacterial, anti-viral, or anti-parasitic agent. The composition and anti-fungal agent could be administered in a single composition or separately. In some embodiments, such separate administration may be within up to 24 or up to 48 hours apart, and in some embodiments, less than an hour apart. The composition could be suitable for use in humans, for veterinary applications, or both.

In some embodiments, the particles, glucans, compositions or combinations thereof of this invention stimulate, enhance or facilitate complement fixation.

According to this aspect, and in some embodiments, the coated substrates, materials, particles, beads, glucans and/or devices of this invention may be used in methods of stimulating, enhancing or promoting immune responses, which involve complement fixation, which result in therapeutic effects in the subject. In some embodiments, such infections may comprise infection with any of the pathogens as herein described. In some embodiments, such immune response may be directed to sepsis in the subject. In some embodiments, such immune response may be directed to Chagas disease in a subject, a pulmonary pathogen, or a parasite or helminth. In some embodiments, such immune response is directed against a viral infection, such as HSV.

In some embodiments, the methods according to this aspect of the invention may further comprise administration of an agent which promotes elaboration of the complement cascade. In some embodiments, according to this aspect of the invention, the methods may further comprise administration of an antibody which specifically recognizes the pathogenic agent with which the subject is infected.

In one embodiment, the β-1-6-glucan is enriched for O-acetylated groups, which in one embodiment contains at least 25% by weight O-acetylated glucan and certain embodiments contains between 10% and 20%, or between 20% and 25% by weight O-acetylated glucan. In another embodiment, the composition further comprises an adjuvant, an antigen, a peptide, an immuno-stimulatory compound, a chemotherapeutic or a combination thereof. In one embodiment, the antigen or peptide is derived from the source of the infection. In one embodiment, the immuno-stimulatory compound is a cytokine. In another embodiment, the chemotherapeutic compound is an antibiotic or antiviral compound.

In another embodiment, this invention provides a method of treating, delaying progression of, prolonging remission of, or reducing the incidence or severity of cancer in a subject, said method comprising administering to said subject a composition comprising purified β-1-6-glucan.

In one embodiment, the antigen is a tumor-associated antigen, or in another embodiment, the peptide is derived from a tumor-associated antigen.

In one embodiment, the subject has a hyperplastic or pre-neoplastic lesion. In another embodiment, the subject has cancer.

In one embodiment, cancers associated with the following cancer antigen may be treated or prevented by the methods and compositions of the invention. KS ¼ pan-carcinoma antigen (Perez and Walker, 1990, J. Immunol. 142:32-37; Bumal, 1988, Hybridoma 7(4):407-415), ovarian carcinoma antigen (CA125) (Yu et al., 1991, Cancer Res. 51(2):48-475), prostatic acid phosphate (Tailor et al., 1990, Nucl. Acids Res. 18(1):4928), prostate specific antigen (Henttu and Vihko, 1989, Biochem. Biophys. Res. Comm. 10(2):903-910; Israeli et al., 1993, Cancer Res. 53:227-230), melanoma-associated antigen p97 (Estin et al., 1989, J. Natl. Cancer Instit. 81 (6):445-44), melanoma antigen gp75 (Vijayasardahl et al., 1990, J. Exp. Med. 171(4):1375-1380), high molecular weight melanoma antigen (HMW-MAA) (Natali et al., 1987, Cancer 59:55-3; Mittelman et al., 1990, J. Clin. Invest. 86:2136-2144)), prostate specific membrane antigen, carcinoembryonic antigen (CEA) (Foon et al., 1994, Proc. Am. Soc. Clin. Oncol. 13:294), polymorphic epithelial mucin antigen, human milk fat globule antigen, colorectal tumor-associated antigens such as: CEA, TAG-72 (Yokata et al., 1992, Cancer Res. 52:3402-3408), CO17-1A (Ragnhammar et al., 1993, Int. J. Cancer 53:751-758); GICA 19-9 (Herlyn et al., 1982, J. Clin. Immunol. 2:135), CTA-1 and LEA, Burkitt's lymphoma antigen-38.13, CD19 (Ghetie et al., 1994, Blood 83:1329-1336), human B-lymphoma antigen-CD20 (Reff et al., 1994, Blood 83:435-445), CD33 (Sgouros et al., 1993, J. Nucl. Med. 34:422-430), melanoma-specific antigens such as ganglioside GD2 (Saleh et al., 1993, J. Immunol., 151, 3390-3398), ganglioside GD3 (shitara et al., 1993, Cancer Immunol. Immunother. 36:373-380), ganglioside GM2 (Livingston et al., 1994, J. Clin. Oncol. 12:1036-1044), ganglioside GM3 (Hoon et al., 1993, Cancer Res. 53:5244-5250), tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellstrom et al., 1985, Cancer. Res. 45:2210-2188), differentiation antigen such as human lung carcinoma antigen L6, L20 (Hellstrom et al., 1986, Cancer Res. 46:3917-3923), antigens of fibrosarcoma, human leukemia T cell antigen-Gp37 (Bhattacharya-Chatterjee et al., 1988, J. of Immun. 141:1398-1403), neoglycoprotein, sphingolipids, breast cancer antigen such as EGFR (Epidermal growth factor receptor), HER2 antigen (p185HER2), polymorphic epithelial mucin (PEM) (Hilkens et al., 1992, Trends in Bio. Chem. Sci. 17:359), malignant human lymphocyte antigen-APO-1 (Bernhard et al., 1989, Science 245: 301-304), differentiation antigen (Feizi, 1985, Nature 314: 53-57) such as 1 antigen found in fetal erythrocytes and primary endoderm, I(Ma) found in gastric adenocarcinomas, M18 and M39 found in breast epithelium, SSEA-1 found in myeloid cells, VEP8, VEP9, Myl, VIM-D5, and D156-22 found in colorectal cancer, TRA-1-85 (blood group H), C14 found in colonic adenocarcinoma, F3 found in lung adenocarcinoma, AH6 found in gastric cancer, Y hapten, Ley found in embryonal carcinoma cells, TL5 (blood group A), EGF receptor found in A431 cells, E1 series (blood group B) found in pancreatic cancer, FC10.2 found in embryonal carcinoma cells, gastric adenocarcinoma, CO-514 (blood group Lea) found in adenocarcinoma, NS-10 found in adenocarcinomas, CO-43 (blood group Leb), G49, EGF receptor, (blood group ALeb/Ley) found in colonic adenocarcinoma, 19.9 found in colon cancer, gastric cancer mucins, T5A7 found in myeloid cells, R24 found in melanoma, 4.2, GD3, D1.1, OFA-1, GM2, OFA-2, GD2, M1:22:25:8 found in embryonal carcinoma cells and SSEA-3, SSEA-4 found in 4-8-cell stage embryos. In another embodiment, the antigen is a T cell receptor derived peptide from a cutaneous T cell lymphoma (see Edelson, 1998, The Cancer Journal 4:62).

In another embodiment, the antigenic peptide or protein is derived from HER2/neu or chorio-embryonic antigen (CEA) for suppression/inhibition of cancers of the breast, ovary, pancreas, colon, prostate, and lung, which express these antigens. Similarly, mucin-type antigens such as MUC-1 can be used against various carcinomas; the MAGE, BAGE, and Mart-1 antigens can be used against melanomas. In one embodiment, the methods may be tailored to a specific cancer patient, such that the choice of antigenic peptide or protein is based on which antigen(s) are expressed in the patient's cancer cells, which may be predetermined by, in other embodiments, surgical biopsy or blood cell sample followed by immunohistochemistry.

In another embodiment, this invention provides for the combined use of, or compositions comprising β-glucans and an immuno-modulatory compound.

Examples of useful immuno-modulating proteins include cytokines, chemokines, complement components, immune system accessory and adhesion molecules and their receptors of human or non-human animal specificity. Useful examples include, but are not limited to: GM-CSF, IL-2, IL-12, OX40, OX40L (gp34), lymphotactin, CD40, and CD40L. Further useful examples include, but are not limited to: interleukins for example interleukins 1 to 15, interferons alpha, beta or gamma, tumor necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, TRAP, ICAM-1, 2 or 3 and cytokine receptors. OX40 and OX40-ligand (gp34) are further useful examples of immuno-modulatory proteins. It is to be understood that any compound which may enhance, stimulate or mitigate or abrogate an immune response, in concert with the glucans as herein described in a given immune response may be incorporated in the compositions of this invention, or used in accordance with the methods of this invention, and is to be considered an embodiment thereof.

In another embodiment, this invention provides for the combined use of, or compositions comprising β-glucans and at least one adjuvant, antigen, immuno-modulatory compound, or a combination thereof. In another embodiment, this invention provides for the combined use of, or compositions comprising β-glucans, which may be derived from multiple sources, combinations of such glucans and two or more adjuvants, antigens immuno-modulatory compounds, or a combination thereof. The β-glucans can be any of the β-glucans described herein, in various embodiments of the invention.

Once formulated, the compositions of the invention can be administered directly to the subject. In some embodiments, the subjects to be treated are animals, including for example, livestock. In some embodiments, the animals to be treated are humans. In some embodiments, males and/or females can be treated with the compositions and/or according to the methods of this invention. In some embodiments, the subjects to be treated are children and/or teenagers, and/or adults.

In one aspect of the present invention, neutrophils induce heat shock protein (HSP) expression upon exposure to β-glucan. The greater the exposure to β-glucan, the greater the expression of HSP, and downstream immune modulation, in some embodiments.

Microspheres coated with β-1,6-glucan as opposed to β-1,3-glucan were most effective at inducing HSP expression, ROS production, etc.

HSPs are already associated with peptides that could be presented on MHC class I and II of antigen-presenting cells. In one embodiment, following recognition of β-1,6-glucan in a composition and/or according to a method of this invention, neutrophils in the subject to which the glucan is administered or with which its cells are contacted, express HSPs to signal to other immune cells, leading to presentation of other antigens on antigen-presenting cells.

In one embodiment, this invention provides a method of modulating an immune response in a subject, the method comprising administering to the subject a composition comprising β-1-6-glucan enriched for O-acetylated groups, or any embodiment thereof as herein described. In another embodiment, this invention provides a method of modulating an immune response in a subject, the method comprising administering to the subject a composition comprising β-1-6-glucan conjugated to a solid support, or any embodiment thereof as herein described. In another embodiment, this invention provides a method of modulating an immune response in a subject, the method comprising administering to the subject a composition comprising β-1-6-glucan, or any embodiment thereof as herein described. In one embodiment, β-glucan in the composition comprises at least from about 35-99% by weight, or in another embodiment, from about 45-99% by weight, or in another embodiment, from about 55-99% by weight, or in another embodiment, from about 65-99% by weight, or in another embodiment, from about 75-99% by weight, or in another embodiment, from about 85-99% by weight, or in another embodiment, from about 90-99% by weight, of β-1-6-glucan, as compared to any other β-glucan. In one embodiment, the term "about" refers to a variance of from 1-10%, or in another embodiment, 5-15%, or in another embodiment, up to 10%, or in another embodiment, up to 25% variance from the indicated values, except where context indicates that the variance should not result in a value exceeding 100%.

According to this aspect of the invention, and in one embodiment, modulating the immune response comprises stimulating said immune response, which in one embodiment is an antigen-specific response. In one embodiment, the composition further comprises an immunostimulatory compound, or in another embodiment, a chemotherapeutic compound. In another embodiment, the immune response is directed against an infectious agent, a cancer, a preneoplastic lesion or a combination thereof, and the compositions comprising, or administration of β-1,6-glucan is useful in this context. In one embodiment, according to this aspect of the invention, additional agents may be administered, or in another embodiment, the compositions for use according to this aspect, may comprise an additional agent, which is useful in this context.

In one embodiment, according to this aspect of the invention, the additional agent may comprise an anti-inflammatory agent such as betamethasone, prednisolone, piroxicam, aspirin, flurbiprofen and (+)-N-{4-[3-(4-fluorophenoxy)phenoxy]-2-cyclopenten-1-yl}-N-hyroxyurea; an antiviral such as acyclovir, nelfinavir, or virazole; an antibiotic such as ampicillin and penicillin G or belonging to the family of penicillines, cephalosporins, aminoglycosidics, macrolides, carbapenem and penem, beta-lactam monocyclic, inhibitors of beta-lactamases, tetracyclins, polipeptidic antibiotics, chloramphenicol and derivatives, fusidic acid, lincomicyn, novobiocine, spectinomycin, poly-etheric ionophores, quinolones; an anti-infective such as benzalkonium chloride or chlorhexidine; dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; an antiinflammatory such as diflunisal, ibuprofen, indomethacin, meclofenamate, mefenamic acid, naproxen, oxyphenbutazone, phenylbutazone, piroxicam, sulindac, tolmetin, aspirin and salicylates; antifungal such as amphotericin B, glucan synthesis inhibitors such as caspofungin, micafungin, or anidulafungin (LY303366), econazole, terconazole, fluconazole, voriconazole or griseofulvin; an antiprotozoal such as metronidazole; an imidazole-type anti-neoplastic such as tubulazole; an anthelmintic agent such as thiabendazole or oxfendazole; an antihistamine such as astemizole, levocabastine, cetirizine, or cinnarizine; a decongestant such as pseudoephedrine; antipsychotics such as fluspirilene, penfluridole, risperidone or ziprasidone; an antineoplastic agent such as platinum compounds (e.g. spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g. PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea, procarbazine, and dacarbazine; a mitotic inhibitor such as etoposide, colchicine, and the vinca alkaloids, a radiopharmaceutical such as radioactive iodine and phosphorus product, or any combination thereof.

In one embodiment, modulating the immune response comprises stimulating the immune response, which in one embodiment is an antigen-specific response. According to this aspect of the invention and in one embodiment, the composition further comprises an immuno-stimulatory compound or in another embodiment, a chemotherapeutic compound. In one embodiment, the immune response is directed against an infectious agent, a cancer, a preneoplastic lesion or a combination thereof, or any embodiment, as herein described.

In some embodiments, the compositions and/or methods of this invention are applied to or useful in stimulating an immune system in an individual (animal or human) by the oral or parenteral administration of compositions containing the β-glucans as herein described. In some embodiments, such compositions and/or methods are effective in boosting the immune response, for example, of individuals, or patients, who are injured, immunocompromised or protein malnourished. An immunocompromised individual refers, in some embodiments, to a person who exhibits an attenuated or reduced ability to mount a normal cellular or humoral defense to challenge by infectious agents, e.g. viruses, bacteria, fungi and protozoa. A protein malnourished individual refers, in some embodiments, to a person who has a serum albumin level of less than about 3.2 grams per deciliter (g/dl) and/or unintentional weight loss of greater than 10% of usual body weight.

In some embodiments, the compositions and/or methods of this invention are used to therapeutically or prophylactically treat animals or humans who are at a heightened risk of infection due to imminent surgery, injury, illness, radiation or chemotherapy, or other condition which deleteriously affects the immune system. In some embodiments, the compositions and/or methods of this invention are used to treat patients who have a disease or disorder which causes the normal immune response to be reduced or depressed, such as HIV infection (AIDS) or who are receiving immunosuppressive therapy (e.g. individuals who are transplant candidates or have received a transplant, individuals suffering from an autoimmune disease, etc.). In some embodiments, the compositions and/or methods of this invention are used to pre-initiate a immune response in patients who are undergoing chemotherapy or radiation therapy, or who are at a heightened risk for developing secondary infections or post-operative complications because of a disease, disorder or treatment resulting in a reduced ability to mobilize the body's normal responses to infection.

In another embodiment, modulating the immune response comprises downmodulating or abrogating the immune response. According to this aspect, and in one embodiment, the composition further comprises an immunosuppressant. In one embodiment, the immune response is directed against an autoantigen or in another embodiment, an allergen, or in another embodiment, the immune response is directed against transplanted tissue or in another embodiment, transplanted cells.

In one embodiment, an immune response to a particular antigen may be initially beneficial to the host, such as, for example, a response directed against an antigen from a pathogen that has to invaded the subject. In one embodiment, such an immune response may be too robust, however, such that even after the pathogen has been eradicated, or controlled, the immune response is sustained and causes damage to the host, such as, for example, by causing tissue necrosis, in tissue which formerly was infected with the pathogen. In these and other circumstances, the compositions and/or methods of this invention may be useful in downmodulating an immune response, such that the host is not compromised in any way by the persistence of such an immune response.

In another embodiment, the immune response, whose downmodulation is desired is host versus graft disease. With the improvement in the efficiency of surgical techniques for transplanting tissues and organs such as skin, kidney, liver, heart, lung, pancreas and bone marrow to subjects, perhaps the principal outstanding problem is the immune response mounted by the recipient to the transplanted allograft or organ, often resulting in rejection. When allogeneic cells or organs are transplanted into a host (i.e., the donor and recipient are different individual from the same species), the host immune system is likely to mount an immune response to foreign antigens in the transplant (host-versus-graft disease) leading to destruction of the transplanted tissue. Accordingly, the compositions and/or methods of this invention may be used, in one embodiment, to prevent such rejection of transplanted tissue or organ.

In another embodiment, the immune response, whose downmodulation is desired is graft versus host disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The compositions and/or methods of this invention may be used, in one embodiment, to preventing or ameliorating such disease.

In another embodiment, the immune response, whose down-modulation is desired is any autoimmune response. According to this aspect of the invention, and in one embodiment, the method comprises administering the described compositions herein to a subject suffering from an autoimmune disease or disorder.

In one embodiment, the term "autoimmune disease" refers to the presence of an autoimmune response in a subject. In one embodiment, the term "autoimmune response" refers to an immune response directed against an auto- or self-antigen. In one embodiment, the autoimmune disease is rheumatoid arthritis, multiple sclerosis, diabetes mellitus, myasthenia gravis, pernicious anemia, Addison's disease, lupus erythematosus, Reiter's syndrome, atopic dermatitis, psoriasis or Graves disease.

According to this aspect and in some embodiments, the compositions of this invention may further comprise an immunosuppressant. In some embodiments, the methods of this invention may make use of concurrent or subsequent administration of an immunosuppressant.

In one embodiment the autoimmune disease or disorder is associated with excessive neutrophil activity, neutrophil infiltration, neutrophil degranulation, etc. In one embodiment the disorder is a disorder that affects the skin, According to this aspect, and in one embodiment, the glucans, compositions, conjugates, particles, micelles, etc., as described herein may be applied directly to the skin.

In one embodiment, the composition further comprises a steroid. In some embodiments, such compositions are useful for down-modulating or abrogating an immune response, and find application in any of the embodiments described herein for downmodulating such responses.

In one embodiment, the term "steroid" refers to naturally occurring steroids and their derivatives as well as synthetic or semi-synthetic steroid analogues having steroid-like activity. In one embodiment, the steroid is a glucocorticoid or corticosteroid. For example, many such steroids have a core fused ring structure based on cyclopentanophenanthrene. Examples of specific natural and synthetic steroids include, but are not limited to: aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, 25 methylprednisolone, paramethasone, prednisolone, prednisone, tixocortol or triamcinolone, and their respective pharmaceutically acceptable salts or derivatives. It will be appreciated that combinations of such steroids may also be used in accordance with this invention.

In some embodiments, such compositions are useful for stimulating or enhancing an immune response, and find application in any of the embodiments described herein for stimulating or enhancing such responses. In one embodiment, the steroid is an androgen, or an androgen receptor agonist.

In another embodiment the composition comprises β-1,3-glucans having β-1,6-glucan branches (also referred to as beta 1,3/1,6,-glucan or beta-1,6-branched beta-1,3-glucan) wherein at least some of the β-1,6-glucan branches are enriched for O-acetylated groups. In another embodiment the invention provides a composition comprising (i) β-1,6-glucan enriched for O-acetylated groups; and (ii) β-1,6-branched β-1,3-glucan. In another embodiment, the composition is substantially free of β-1,3-glucan. In certain embodiments the composition contains less than 75%, or less than 50%, or less than 25%, or less than 10%, or less than 5%, or less than 1%, or less than 0.1% β-1,3-glucan by weight. In certain embodiments less than 50%, or less than 25%, or 10%, or less than 5%, or less than 1%, or less than 0.1% of the total glucan in the composition, by weight, is β-1,3-glucan.

It is to be understood that the downmodulation of any immune response, via the compositions and/or methods of this invention of this invention are to be considered as part of this invention, and an embodiment thereof.

In one embodiment, the compositions and/or methods of this invention stimulate and/or enhance the secretion of substances, which mediate the suppressive effects. In one embodiment, the compositions and/or methods of this invention mediate bystander suppression, without a need for direct cell contact. In one embodiment, the substances mediating suppression secreted by the T suppressor cell populations of this invention may include IL-10, TGF-β, or a combination thereof.

In another embodiment, modulating the immune response may comprise shifting the cell type participating in the immune response, cell product elaborated during the immune response and/or the overall character of the response, for example, shifting a Th1 to Th2 type response, or vice versa. In one embodiment, the methods/compositions of this invention provide for eliciting a "Th1" response, in a disease where a so-called "Th2" type response has developed, when the development of a so-called "Th1" type response is beneficial to the subject.

In one embodiment, the term "Th2 type response" refers to a pattern of cytokine expression, elicited by T Helper cells as part of the adaptive immune response, which support the development of a robust antibody response. Typically Th2 type responses are beneficial in helminth infections in a subject, for example. Typically Th2 type responses are recognized by the production of interleukin-4 or interleukin 10, for example.

In another embodiment, the term "Th1 type response" refers to a pattern of cytokine expression, elicited by T Helper cells as part of the adaptive immune response, which support the development of robust cell-mediated immunity. Typically Th1 type responses are beneficial in intracellular infections in a subject, for example. Typically Th1 type responses are recognized by the production of interleukin-2 or interferon γ, for example.

In another embodiment, the compositions and/or methods of this invention are useful in modulating the response such that where a Th1 type response has developed, when Th2 type responses provide a more beneficial outcome to a subject, the methods and/or compositions of this invention provide for a shift to the more beneficial cytokine profile. One example would be in leprosy, where the compositions and/or methods of the present invention stimulate a Th1 cytokine shift, resulting in tuberculoid leprosy, as opposed to lepromatous leprosy, a much more severe form of the disease, associated with Th2 type responses.

In another embodiment, this invention provides a method of inducing expression of heat shock proteins in a cell, e.g. an antigen-presenting cell, the method comprising contacting the antigen-presenting cell with a composition comprising β-1-6-glucan enriched for O-acetylated groups.

In another embodiment, this invention provides a method of inducing expression of heat shock proteins in a cell, e.g. an antigen-presenting cell, the method comprising contacting the antigen-presenting cell with a composition comprising β-1-6-glucan conjugated to a solid support.

As exemplified herein, phagocytosis of particles comprising β-1-6-glucan, but not compositions comprising β-1-3-glucan, promoted heat shock protein (hsp) induction.

In one embodiment, the cell is a neutrophil. In another embodiment, the antigen-presenting cell is a dendritic cell or a macrophage.

According to this aspect of the invention, and in another embodiment, this invention provides a method of inducing expression of heat shock proteins in cells, e.g. antigen-presenting cells, neutrophils, etc., the method comprising contacting the antigen-presenting cells/neutrophils with a composition comprising β-1-6-glucan, wherein at least 25% of the glucose units in at least 5% of the glucan molecules are enriched for O-acetylated groups.

In another embodiment the invention provides a method of stimulating or enhancing antigen presentation, the method comprising contacting an antigen-presenting cell with a composition comprising β-1-6-glucan, wherein said contact promotes or induces antigen presentation by said antigen-presenting cell.

In one embodiment, phagocytic cells undergo apoptosis following uptake of the β-1-6-glucan. According to this aspect of the invention, and in one embodiment, the invention provides a method of promoting or stimulating cellular apoptosis, the method comprising contacting a cell with a composition comprising β-1-6-glucan, wherein the composition induces expression of at least one heat shock protein in said cell and subsequent apoptosis of said cell. According to this aspect and in one embodiment, the cell is from a subject with an infection or autoimmune disease, and promoting apoptosis of such cells provides a therapeutic effect in the subject.

In some embodiments, this invention provides a method of modulating macrophage responsiveness comprising contacting macrophages with neutrophils that have been contacted with a composition comprising β-1-6-glucan enriched for O-acetylated groups.

In another embodiment, the invention provides a method modulating an immune response in a subject, the method comprising administering to the subject a composition comprising a β-1-6-glucan physically associated with a targeting moiety, wherein the targeting moiety specifically interacts with or attracts a phagocytic cell.

In one embodiment, modulating said immune response comprises stimulating said immune response, which in one embodiment is an antigen-specific response. In one embodiment, the composition further comprises an immuno-stimulatory compound, or in another embodiment, the composition further comprises a chemotherapeutic compound. In one embodiment, the immune response is directed against an infectious agent, a cancer, a preneoplastic lesion or a combination thereof, and in another embodiment, the immune response is complement-dependent.

In one embodiment, this invention provides a method of treating, delaying progression of, or reducing the incidence or severity of an infection in a subject, said method comprising administering to said subject a composition comprising a β-1-6-glucan physically associated with a targeting moiety, wherein the targeting moiety specifically interacts with or attracts a phagocytic cell. In one embodiment, the composition further comprises an adjuvant, an antigen, a peptide, an immuno-stimulatory compound, a chemotherapeutic or a combination thereof. In one embodiment, the antigen or peptide is derived from the source of the infection. In another embodiment, the immuno-stimulatory compound is a cytokine. In another embodiment, the chemotherapeutic compound is an antibiotic or antiviral compound.

In one embodiment, this invention provides a method of stimulating or enhancing heat shock protein expression in a cell, the method comprising contacting the cell with comprising a β-1-6-glucan physically associated with a targeting moiety, wherein the targeting moiety specifically interacts with or attracts a phagocytic cell.

In some embodiments, the methods of this invention serve to enhance the activity of a variety of cells of the immune system cells such as macrophages, dendritic cells, etc., in some embodiments, in addition to, or in some embodiments, instead of, neutrophils.

In some embodiments, the methods of this invention serve as a general approach to promoting cellular cytotoxic effects, via use of a ligand, which serves to target the cell or material against which a cytotoxic response is desired, conjugated to a glucan of this invention, which in turn serves, in some embodiments, to promote cytotxicity against the targeted cell or material.

In some embodiments, the glucans as described herein, compositions comprising same, and β-1-6-glucan physically associated with a targeting moiety, and compositions comprising the same may function to enhance complement-mediated lysis in a subject. In some embodiments, such enhancement may involve the phagocytic cell response, for example, enhancing neutrophil or macrophage, or other professional antigen-presenting cell phagocytosis and cytotoxic responses. In some embodiments, such enhancement may be independent of phagocytic cell involvement, for example, by enhancing membrane attack complex formation and/or activity.

In some embodiments, this invention provides a method of treating, delaying progression of, prolonging remission of, or reducing the incidence or severity of cancer in a subject, via contacting a cell in a subject, or administering to the subject a glucan, composition, conjugate, micelle, preparation or particle of this invention.

In some embodiments, the invention is to be understood as encompassing compositions that comprise, and conjugates comprising any compound that facilitates immune cell recruitment, for example cells of the innate immune response, such as neutrophils. Such a compound is referred to herein as, inter alia, a targeting moiety, which facilitates immune cell activation, stimulatory immune responses, cytotoxicity against a desired target, which in some embodiments is specifically targeted through the described moiety, for example, via the specificity dictated by antibody or fragment conjugated or associated with the glucan.

In some embodiments, the invention comprises conjugates and compositions comprising an antibody with a desired specificity to suit a particular application, as described herein, and as will be appreciated by the skilled artisan. In some embodiments, such conjugates and compositions/preparations as described herein may comprise, inter alia, any complement-fixing compound known in the art. In some embodiments, conjugates and compositions/preparations as described herein specifically exclude cobra venom factor, yet make use of any other complement-fixing compound. In some embodiments, the conjugates and compositions/preparations as described herein may comprise any polysaccharide except dextran. In some embodiments, the conjugates and compositions/preparations as described herein may comprise any glucan, including, inter alia, acetylated β-1,6-glucan, β-1,6-glucan, mix of β-1,3-glucan and β-1,6-glucan, β-1,3-glucan, mix of β-1,3-glucan β-1,4-glucan, β-1,4-glucan, acetylated glucans, and/or any glucan comprising any other modification. In some embodiments, the conjugates and compositions/preparations as described herein may comprise any glucan, including genetically engineered forms, for example, β-glucans synthesized in bacteria, yeast, mammalian cells, etc., by recombinant means.

In some embodiments, the conjugates and compositions/preparations as described herein may be applied for the immunization of a subject against *Candida albicans* and other fungal infection.

In any of the afore-mentioned embodiments the contacting may occur either outside the body of a subject or within the body. In one embodiment, cells, such as antigen-presenting cells, which in some embodiments are neutrophils, or macrophages or dendritic cells, are removed from a subject, contacted with the composition, and then administered to the subject at a subsequent point in time. In one embodiment the cells are contacted with the composition for a time sufficient to induce expression of heat shock proteins. In one embodiment the cells are contacted with the composition for a time sufficient to induce production of reactive oxygen species. In one embodiment the subject receives immunosuppressive therapy prior to administration of the cells. For example, a subject may be in need of immunosuppressive therapy for organ transplantation or other purposes, e.g. chemotherapy or radiation therapy for cancer, leukemia, lymphoma, or any type of tumor, wherein the therapy would tend to render the individual immunocompromised. In one embodiment of the invention, prior to administering the immunosuppressive therapy, immune system cells are removed from the subject. The cells (which, in some embodiments, are neutrophils or in other embodiments, other immune system cells, such as other professional antigen-presenting cells, such as macrophages or dendritic cells) are contacted outside the body with a composition of this invention and are then returned to the subject a suitable period of time after the subject has received the immunosuppressive therapy. The suitable period of time could be, e.g. after the therapy has been administered or its cytotoxic effects have diminished, when the subject is at risk of or exhibits symptoms or signs of infection, etc.

It is to be understood that the methods and/or compositions of this invention which by affecting/modulating an immune response, in turn prevent disease, and/or ameliorate disease, and/or alter disease progression are to be considered as part of this invention.

In some embodiments, the term "contacting" or "administering" refers to both direct and indirect exposure to the indicated material.

In some embodiments, the compositions and/or methods of this invention comprise or make use of a non-sterile or sterile carrier or carriers for administration to cells, tissues or organisms, such as a pharmaceutical carrier suitable for administration to an individual. Such carriers may include, but are not limited to, saline, buffered saline, dextrose, water, glycerol, and combinations thereof. The formulation should suit the mode of administration.

The compositions or glucans of this invention may be administered in any effective, convenient manner including, for instance, administration by intravascular (i.v.), intramuscular (i.m.), intranasal (i.n.), subcutaneous (s.c.), oral, rectal, intravaginal delivery, or by any means in which the glucan/composition can be delivered to tissue (e.g. needle or catheter). Alternatively, topical administration may be desired for insertion into epithelial cells. Another method of administration is via aspiration or aerosol formulation. In some embodiments the glucan is administered by implanting or introducing into the body of a subject, an implant or other medical or surgical device that comprises the glucan, e.g. as a component of a coating layer.

In one embodiment, the invention provides a food supplement comprising β-1-6-glucan enriched for O-acetylated groups. In one embodiment, the invention provides a food product comprising β-1-6-glucan enriched for O-acetylated groups. In another embodiment, the invention provides a cosmetic composition comprising β-1-6-glucan enriched for O-acetylated groups.

In some embodiments, a food or food product is any substance that is substantially non-toxic that can be metabolized by an organism to give energy and build tissue. In some embodiments, a food or food product denotes a product intended for ingestion by a mammal, e.g, by humans, which has nutritional value. In some embodiments a food or food product denotes a product regulated as a food or food product by the U.S. Food and Drug Administration (FDA). In some embodiments, a food or food product is a product packaged in a container bearing a label indicating that the product is a food or food product. In some embodiments, a food or food product is a product packaged in a container bearing a label providing nutritional information regarding the product, such as the calorie, fat, or protein content, or the content of one or more vitamins or minerals. In some embodiments a food supplement (also referred to as a "dietary supplement") is any substance that is added to a food or food product. In some embodiments the food supplement comprises, in addition to a glucan of this invention, one or more essential nutrients, such as vitamins, minerals, and protein. In some embodiments, the food supplement is any product intended for ingestion as a supplement to the diet and may comprise, in addition to a glucan of this invention, one or more vitamins, minerals, herbs, botanicals, and other plant-derived substances; amino acids; and concentrates, metabolites, constituents and extracts of these substances. In some embodiments, the food, food product, food supplement, or cosmetic composition is not intended to diagnose, cure, mitigate, treat, or prevent disease. In some embodiments, the food supplement is provided in a container or other packaging material labeled to indicate that the contents are a food or dietary supplement, e.g. in accordance with then current U.S. law and/or FDA guidelines. In some embodiments, the food supplement or product comprises about 0.01 to 30 w/w % of the glucan, and may additionally comprise vitamins, oligosaccharides, dietary ingredients, proteins, or a combination thereof.

In some embodiments, the ratio of the components is not fixed, or in other embodiments, such ratio may range from about 0.01 to 30 w/w % per 100 w/w %. Examples of food comprising aforementioned glucan of this invention therein are various food, beverage, gum, vitamin complex, health improving food and the like.

The composition may additionally comprise one or more than one of organic acid, such as citric acid, fumaric acid, adipic acid, lactic acid, malic acid; phosphate, such as phosphate, sodium phosphate, potassium phosphate, acid pyrophosphate, polyphosphate; natural anti-oxidants, such as polyphenol, catechin, alpha-tocopherol, rosemary extract, vitamin C, licorice root extract, chitosan, tannic acid, phytic acid etc.

In some embodiments, a cosmetic or personal care composition is a composition that enhances or improves the appearance of at least a portion of the body, e.g. hair, nails, skin, etc. In one embodiment, the composition beautifies the body. In one embodiment the composition restores a more youthful appearance. In one embodiment, any composition applied or delivered to a subject is considered a cosmetic is it is administered for purposes of enhancing or improving the appearance of at least a portion of the body, e.g. hair, nails, skin, etc., or for restoring a more youthful appearance. In some embodiments, the cosmetic or personal care compositions of this invention may comprise an emollient, moisturizing agent, soothing agent, ultraviolet A or B blocking agent, retinoid, coloring agent, or fragrance, etc. In some embodiments the cosmetic or personal care composition contains, in addition to a glucan of this invention, any other component recognized in the art as being useful in providing a beneficial effect to the appearance. In some embodiments, the cosmetic or personal care composition is provided in a container labeled to indicate its intended use as a cosmetic and/or labeled to indicate that it is for external use only.

In some embodiments, the compositions of this invention are formulated as a topical ointment, lotion, gel, or cream containing the active ingredient(s) in an amount of, for example, 0.0001 to 50% w/w, e.g. 0.075 to 20% w/w (including active ingredient(s) in a range between 0.1% and 20% in increments of 0.1% w/w such as 0.6% w/w, 0.7% w/w, etc.), often 0.2 to 15% w/w and most often 0.5 to 10% w/w). In some embodiments, when formulated in an ointment, the active ingredients may be employed with either a paraffinic or a water-miscible ointment base. In some embodiments, the active ingredients may be formulated in a cream with an oil-in-water cream base.

In some embodiments, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. In some embodiments, the topical formulations may include a compound that enhances absorption or penetration of the active ingredient(s) through the skin or other affected areas. Examples of such dermal penetration enhancers include dimethyl sulphoxide and related analogs.

In some embodiments, the compositions of this invention may make use of emulgents and/or emulsion stabilizers, such as, for example, Tween60™, Span80™, cetostearyl alcohol, benzyl alcohol, myristyl alcohol, glyceryl mono-stearate and/or sodium lauryl sulfate.

In some embodiments, the choice of suitable oils or fats for the formulation is based on achieving the desired cosmetic properties. Creams are generally non-greasy, non-staining and washable products with suitable consistency to avoid leakage from tubes or other containers. Straight- or branched-chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. In some embodiments, high melting point lipids such as white soft paraffin and/or liquid paraffin or other mineral oils are used.

In some embodiments, the compositions are formulated for use as eye drops wherein the active ingredient(s) is dissolved or suspended in a suitable excipient(s), for example, an aqueous solvent for active ingredient(s) that comprise one or more charges at pH values near neutrality, e.g. about pH 6-8. In some embodiments, the active ingredient(s) is present in such formulations in a concentration of about 0.5-20% w/w, typically about 1-10% w/w, often about 2-5% w/w.

In some embodiments, the compositions of this invention are formulated for topical administration in the mouth, and may include lozenges comprising the active ingredient in a flavored basis, which may comprise sucrose and acacia or tragacanth; pastilles comprising the active ingredient(s) in an inert basis such as gelatin and glycerin, or sucrose and acacia, or others; or mouthwashes comprising the active ingredient in a suitable liquid excipient(s), or others as will be appreciated by one skilled in the art.

Formulations for rectal administration may be presented as a suppository with a suitable base comprising for example cocoa butter or a salicylate.

Formulations suitable for intrapulmonary or nasal administration have a particle size for example in the range of 0.01 to 500 microns (including average particle sizes in a range between 0.01 and 500 microns in 0.1 micron or other increments, e.g. 0.05, 0.1, 0.5, 1, 1.5, 2.0, 2.5, 3.0, 3.5, 4.0, 4.5, 5.0, 6, 7, 8, 9, 10, 20, 25, 30, 35, 50, 75, 100, etc. microns), which is administered by rapid inhalation through the nasal passage or by inhalation through the mouth so as to reach the alveolar sacs. Suitable micronized formulations include aqueous or oily solutions or suspensions of the active ingredient(s). Formulations suitable for aerosol, dry powder or tablet administration may be prepared according to conventional methods and may be delivered with other therapeutic agents such as compounds heretofore used in the treatment or prophylaxis of viral or other infections as described herein. Such formulation may be administered, e.g. orally, parenterally (i.v., i.m., s.c.), topically or by a buccal route. According to this aspect of the invention, and in some embodiments, the β-1,6-glucan utilized in the composition is enriched for O-acetylated glucan, as herein described, conjugated to a particle or bead, as herein described, or a combination thereof.

Formulations suitable for vaginal administration may be presented as pessaries, tampons, creams, gels, pastes, foams or spray formulations containing in addition to the active ingredient(s) such excipients as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampules and vials, and may be stored in a freeze-dried (lyophilized) condition requiring only the addition of the sterile liquid excipient, for example water for injection, immediately prior to use. Extemporaneous injection solutions and suspensions are prepared from sterile powders, granules and tablets of the kind previously described. Unit dosage formulations are those containing a daily dose or unit daily sub-dose, as recited herein, or an appropriate fraction thereof, of the active ingredient(s).

In some embodiments, the β-glucans of this invention, in any of its forms as described herein, will be administered to a subject at a dosage of 0.1 mg to about 50 mg/kg weight of the subject. In some embodiments, the β-glucans of this invention will be administered according to any regimen, in terms of the number of times per day, duration of time, etc., which may be adjusted as a part of a course of therapy for a subject, as will be appreciated by the skilled artisan.

It should be understood that in addition to the ingredients particularly mentioned above the formulations of this invention may include other agents or excipients conventional in the art having regard to the type of formulation in question, for example those suitable for oral administration may include flavoring agents.

It will be apparent to those skilled in the art that various modifications and variations can be made in the compositions, use and preparations of the present invention without departing from the spirit or scope of the invention.

For administration to mammals, and particularly humans, it is expected that in the case of medications, the physician or other qualified healthcare provider may determine the actual dosage and duration of treatment, which will be most suitable for an individual and can vary with the age, weight and response of the particular individual. It will be appreciated that in the case of non-prescription (e.g. "over-the-counter") medications, foods, food products, food supplements, cosmetic and personal care compositions, the amount may be determined at the discretion of the user, optionally with guidance from the labeling or from an appropriate health care provider or other advisor.

EXAMPLES

Materials and methods

Phagocytes

Neutrophils and monocytes were isolated as described [Rubin-Bejerano, I., et al., Proc Natl Acad Sci USA, 2003. 100(19): p. 11007-12] from fresh human blood collected from healthy volunteers in accordance with a protocol approved by the MIT Committee on Use of Humans as Experimental Subjects.

Preparation of *Candida*

The *Candida* strain was the commonly used laboratory strain CAF2-1 (Ca). *Candida* was grown on standard media (YPD), as described [Sherman, supra]. Overnight cultures were used in all experiments (about $3\times10^8$ cells/ml), because the *Candida albicans* population was found to be more homogenous (contain >99% yeast form cells) than in mid-logarithmic phase.

In order to test how neutrophils recognize fungi, and to avoid any alteration of fungi by media or neutrophils or manipulation of neutrophils by the fungi, fungi were inactivated by UV, which kills the cells but does not alter the fungal cell wall structure [Wheeler, R. T. and G. R. Fink, PLoS Pathog, 2006. 2(4): p. e35].

Opsonization of *Candida*

A pool of fresh human serum was generated from ten healthy volunteers, and was used for all experiments. Fungal cells were pre-opsonized in 50% serum in Dulbecco's phosphate-buffered saline without calcium chloride and without magnesium chloride (Gibco) for 15 minutes at 37° C. on a mixer. Cells were then incubated on ice for 5 minutes, washed twice with 0.04 mg/ml of the protease inhibitor AEBSF (Sigma) in the same buffer, and then washed twice with the same buffer without AEBSF. Fungal cells were recounted.

Co-Incubation of Phagocytes with *Candida*

Neutrophils or monocytes were mixed with *Candida albicans* cells at ratio of 1:5 phagocyte:target. Phagocytes were cultured with opsonized fungi, or alone in RPMI1640 at 37° C. for 2 hours, and were frozen in TRI reagent (MRC) at −80° C.

Microarray Procedure

Total RNA was prepared following the TRI reagent protocol, except that for RNA precipitation it was incubated with isopropanol overnight at 4° C. First and second strand synthesis, in vitro transcription, hybridization, and scanning were done as described before [Rubin-Bejerano, I., et al., Proc Natl Acad Sci USA, 2003. 100(19): p. 11007-12]. The microarrays were GeneChip Human Genome U133A 2.0 array (Affymetrix).

Microarray Analysis

Data sets were normalized and floored to 20. Ratios of expression from neutrophils cultured with *Candida* divided by that from the neutrophils alone control were calculated. Induced and repressed genes were defined as those with an expression ratio greater than two standard deviations from the mean for a given experiment. Only genes that were consistently induced or repressed in two experimental duplicates were considered as induced or repressed.

Real Time-PCR (RT-PCR) on Neutrophils Engulfing *Candida*

Total RNA was prepared following the TRI reagent protocol, except that for RNA precipitation it was incubated with isopropanol overnight at 4° C. cDNA was created using High Capacity cDNA Archive Kit (Applied Biosystems). Quantitative RT-PCR was done using TaqMan® Gene Expression Assays (Applied Biosystems) and 7500 Real Time PCR system (Applied Biosystems), following the manufacturer protocol. The following TaqMan® Gene Expression Assays were used: ACTB (Hs99999903_m1), DNAJB1 (Hs00428680_m1), HSPCB (Hs00607336_gH), HSPH1 (Hs00198379_m1), CXCL2 (Hs00236966_m1), and CCL3 (Hs00234142_m1). Fold induction was calculated as the ratio of expression from phagocytes cultured in an experimental condition divided by that from the phagocytes alone control.

Carbohydrates

Laminarin (Sigma) is a pure β-1,3-glucan preparation, and Pustulan (Calbiochem) is a pure β-1,6-glucan preparation. Dextran (Fluka) is an β-1,6-glucan. Glucan from barley (Sigma) is composed of β-1,3-glucan (30%), and β-1,4-glucan (70%). Pustulan was processed as described [Lindberg, B. and J. McPherson, Acta Chem. Scand., 1954. 8: p. 985-988]. When indicated, pustulan was specifically digested using an endo β-1,6-glucanase [Lora, J. M., De la Cruz, J., Llobell, A., Benitez, T. and Pintor-Toro, J. A. Mol Gen Genet. 1995. 247: p. 639-45.]. The enzyme was a kind gift from Dr. Nick Zecherle (Biomarin Pharmaceutical, Inc). The reaction products were analyzed by gel filtration and thin-layer chromatography.

Gel Filtration Chromatography

Pustulan (20 mg) was applied to a BioGel P6 column (1.5×120 cm, BioRad, 200-400 mesh). The column was equilibrated in 0.1 M acetic acid and run at a constant flow rate of 15 ml/h, 1.5 ml fractions were collected and carbohydrate was measured by the phenol-sulfuric acid method. Fractions containing the peaks were dried twice for complete elimination of acetic acid and suspended in water at 10-20 mg/ml. Cytochrome C was used as a marker of the exclusion volume and glucose as a marker of the inclusion volume.

Thin-Layer Chromatography (TLC)

Samples (5 µl) were ascended twice on silica gel 60 plates (Merck, 0.25 mm), 20 cm length. The solvent system was n-butanol/ethanol/water (5:3:2). The samples and standards were visualized by heating the plates at 80° C. after spraying with phenol-sulfuric acid. Standard gentiooligosaccharides were prepared from partial acid hydrolysate of pustulan and isolated by BioGel P4 chromatography as described [[Magnelli, P., Cipollo, J. F., and Abeijon, C. (2002). Anal Biochem 301, 136-150.].

O-deacetylation of Pustulan

Pustulan (3 ml, 15 mg/ml) was adjusted to 0.1 M NaOH and incubated for 1 hr at 37° C. and dialyzed against water.

Preparation of glucan-Coated Microspheres

Polybead polystyrene 6.0 micron microspheres (Polysciences, Inc.) were coated with polysaccharides as described [Schlesinger, L. S., S. R. Hull, and T. M. Kaufman, J Immunol, 1994. 152(8): p. 4070-9]. Pustulan tends to solidify at room temperature.

Pustulan was solubilized in boiling water, and let cool to room temperature prior to its application to beads. Microsphere coating was detected by the phenol-sulfuric acid method, measuring carbohydrates [Duboius, M., et al., Anal. Biochem., 1956. 28: p. 350-356].

Unless stated otherwise, only beads with 6-15 µg glucose per 1 ml ($2 \times 10^8$ beads) were included in the analysis (see Table 1). Short polysaccharides were not found to coat the beads efficiently by this method. Moreover, by this method, acetylated glucans coated the beads better than unacetylated glucans. When not acetylated, more of the glucan was added to the beads to achieve similar levels of coating.

Opsonization of Beads

Beads were opsonized as described above for *Candida*.

Coincubation of Neutrophils with Beads

Beads were coincubated with neutrophils as described above for *Candida*.

Real Time-PCR of Neutrophils Engulfing Beads

RT-PCR was performed as described above for *Candida*. Fold induction was calculated as the ratio of expression from neutrophils cultured with carbohydrate-coated beads over neutrophils cultured with untreated beads.

Reactive Oxygen Species (ROS) Production Assay

| Pus input | Pus coating | PMN expression (fold induction) | | |
|---|---|---|---|---|
| (µg glucose) | (µg glucose/ml) | DNAJB1 | HSPCB | HSPH1 |
| 14,400 | 37.3 | 5.2 | 4.7 | 8.3 |
| 10,800 | 19.6 | 4.6 | 4.9 | 10.3 |
| 7,200 | 9.0 | 7.6 | 7.2 | 21.0 |
| 3,600 | 9.2 | 2.8 | 2.4 | 3.9 |
| 1,800 | 6.6 | 3.3 | 3.0 | 4.9 |
| 900 | 6.6 | 3.3 | 2.8 | 5.9 |

ROS production was assayed using DHR123 (Molecular Probes), which becomes fluorescent when oxidized[28]. $5 \times 10^6$ neutrophils were cultured with indicated beads at ratio of 1:5 in volume of 1 ml for 1 hr at 37° C. 1 µl of DHR123 (D-23806) was added to 200 µl of culture. Following incubation at room temperature for 30 minutes the cells were assayed by Fluorescence-Activated Cell Sorting (FACS).

Identification of Serum Proteins Binding β-1,6-glucan

Beads were coated with equivalent amounts of β-1,3-glucan and β-1,6-glucan, and opsonized as described above. Beads were suspended in 2% SDS 1M ammonium hydroxide buffer, and incubated at 37° C. for 1 hour. The supernatant was loaded on 4-20% acrylamide SDS gel. The gel was stained with silver stain, and bands were cut for analysis by mass spec.

Western Analysis of C3

Western analysis of C3. C3 deposition was assayed using monoclonal antibodies directed against the alpha or the beta chain of C3b (RDI Reasearch Diagnostics).

Killing Assay

Viability of *Candida albicans* was determined using XTT as described before (Meshulam, T., Levitz, S. M., Christin, L., and Diamond, R. D. (1995). J Infect Dis 172, 1153-1156).

Preincubation Experiments

Serum was preincubated with equivalent amount of soluble laminarin or pustulan for 5 minutes at 37° C. The serum was then used to opsonize pustulan-coated beads as described above.

CR3 Blocking Ab

Neutrophils were preincubated with anti-human Mac-1 or isotype control IgG (Bender Med Systems) for 30 minutes on ice before adding to opsonized pustulan-coated beads.

Example 1

β-1,6-glucan Stimulates Neutrophils

The *Candida* strain, CAF2-1, was used to analyze the response of neutrophils to fungi. Microarray experiments showed that neutrophils phagocytosing *Candida* express heat shock proteins (HSPs) (The 10 kDa HSPE1, 40 kDa DNAJB1 DNAJB9, 70 kDa HSPA1A and HSPA9B, 90 kDa HSPCA and HSPCB, and 105/110 kDa HSPH1) (Table 2), along with cytokines and chemokines, such as the IL-8 receptor ligand CXCL2, and CCL3.

TABLE 2

| No. | Affymetrix Probe Set Name | Gene | Exp. 1 | Exp. 2 |
|---|---|---|---|---|
| 1 | 208744_x_at | HSPH1 | 4.3 | 4.9 |
| 1 | 206976_s_at | HSPH1 | 7.2 | 9.6 |
| 2 | 205133_s_at | HSPE1 | 2 | 9.7 |
| 3 | 200064_at | HSPCB | 3 | 6.7 |
| 3 | 214359_s_at | HSPCB | 3.1 | 7.1 |
| 4 | 211969_at | HSPCA | 2.7 | 5.7 |
| 4 | 210211_s_at | HSPCA | 3 | 5.2 |
| 4 | 211968_s_at | HSPCA | 3.6 | 7.2 |
| 5 | 200690_at | HSPA9B | 2.8 | 3.1 |
| 6 | 202581_at | HSPA1A | 10.8 | 12 |
| 7 | 202842_s_at | DNAJB9 | 6.8 | 6.6 |
| 7 | 202843_at | DNAJB9 | 9.1 | 9.7 |
| 8 | 200666_s_at | DNAJB1 | 5.8 | 10.1 |
| 8 | 200664_s_at | DNAJB1 | 5.9 | 11.2 |

Figure 1:
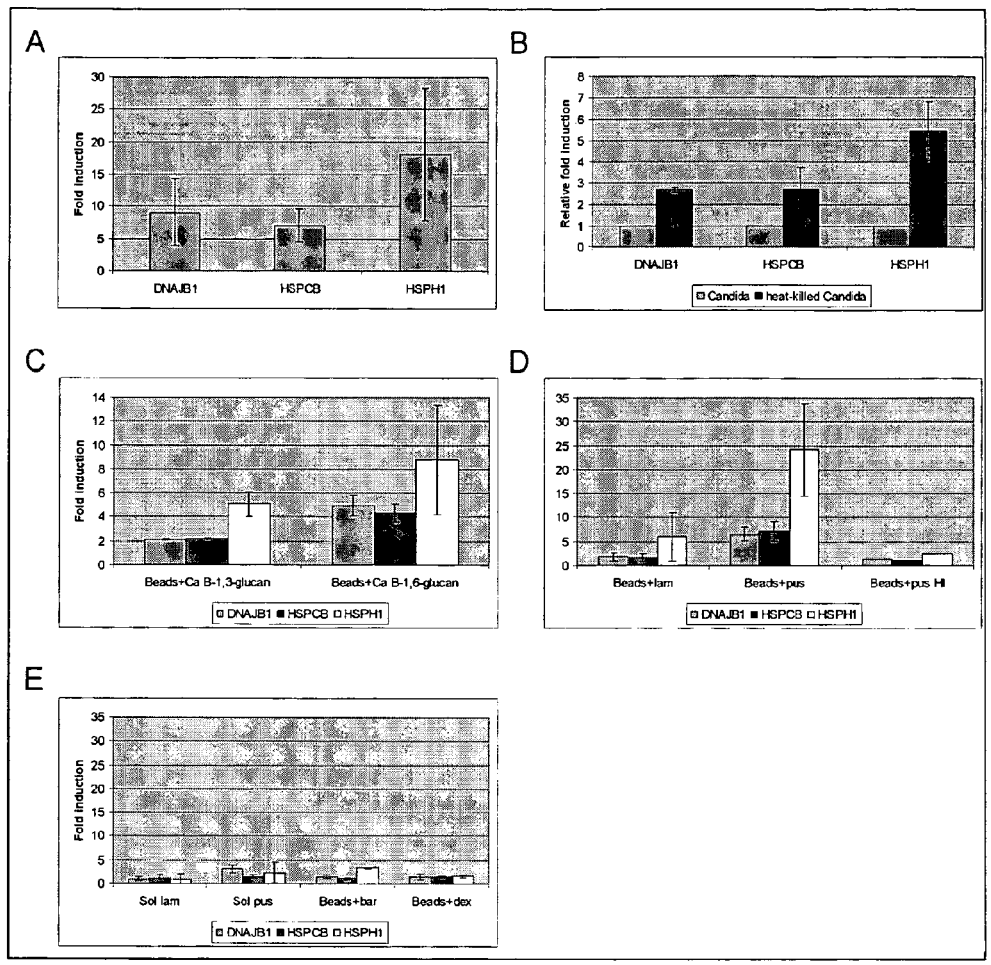
FIG. 1. β-1,6-glucan stimulates expression of heat shock proteins (HSPs) in neutrophils. Induction of HSPs was determined by quantitative real-time PCR. The data represent the average of two (A) or at least three experiments with standard deviation. Candida (Ca) or beads were opsonized with pooled human serum and cultured for 2 hours with neutrophils. (A) Candida albicans elicits HSPs in neutrophils. The fold induction represents the ratio of neutrophils+Candida to neutrophils alone. (B) Heat-killed Candida elicits higher levels of HSPs. Results for heat-killed Candida were normalized to UV-killed Candida. (C-E) β-1,6-glucan stimulates expression of HSPs. Polybead polystyrene 6.0 micron microspheres (beads) were coated with an equivalent amount of one of the following glucans: laminarin (lam, algal β-1,3-glucan), β-1, 6-glucan purified from Candida albicans (Ca β-1,6-glucan), pustulan (pus, lichen β-1,6-glucan), barley glucan (bar, 30% β-1,3-glucan, and 70% β-1,4-glucan), or dextran (dex, α-1, 6-glucan). Beads were opsonized with pooled human serum, or with heat inactivated (HI) pooled human serum (D). The fold induction represents the ratio of neutrophils+glucans-coated beads over neutrophils+untreated beads. (C) Fungal β-1,6-glucan stimulates expression of HSPs. Beads were coated with β-1,3-glucan purified from Candida albicans (Ca β-1,3-glucan), or β-1,6-glucan purified from Candida albicans (Ca β-1,6-glucan). (D) Standard β-1,6-glucan stimulates expression of HSPs. Beads were coated with laminarin (lam, algal β-1,3-glucan), or pustulan (pus, lichen β-1,6-glucan). (E) Soluble β-1,6-glucan and other glucan-coated beads do not stimulate expression of HSPs. Beads were coated with β-glucan isolated from barley (bar, 30% β-1,3-glucan, and 70% β-1,4-glucan), or with dextran (dex, α-1,6-glucan). Neutrophils were cultured with 5 mg/ml of soluble laminarin (sol lam), 5 mg/ml of soluble pustulan (sol pus), or beads. The fold induction represents the ratio of neutrophils+soluble glucans over neutrophils alone, or neutrophils+glucans-coated beads over neutrophils+untreated beads.

Expression of HSPs by neutrophils was corroborated by quantitative RT-PCR (FIG. 1A).

The induction of HSPs was greater if *Candida* was first heated to unmask the underlying β-glucan (FIG. 1B), suggesting that expression of HSPs is proportional to exposed β-glucan.

To assay which of the glucan components was responsible for this induction, neutrophils were presented with various glucan polymers. Glucans in the soluble form elicited only low levels of HSPs in neutrophils (FIG. 1E).

As neutrophils respond best to particulate material, several sources of β-glucan were conjugated to 6 micron polystyrene beads, which are similar in size to *Candida albicans* yeast form cells (5μ). β-1,3-glucan and β-1,6-glucan purified from *Candida* cell walls were utilized (FIG. 1C), as well as non-fungal sources of β-1,3-glucan and β-1,6-glucan that have been used as standards in previous studies (FIG. 1D) [Brown, G. D. et al. Nature 413, 36-7; Palma, A. S. et al. J Biol Chem 281, 5771-9].

Beads coated with pustulan or β-1,6-glucan from *Candida albicans* elicited high levels of HSPs in neutrophils (FIG. 1C,D), whereas beads coated with laminarin or β-1,3-glucan from *Candida albicans* elicited minimal expression of HSPs (FIG. 1C,D), despite efficient coating of the beads. β-glucan from barley, which is composed of β-1,3-glucan (30%) and β-1,4-glucan (70%) also did not elicit HSPs expression (FIG. 1E). Beads coated with α-1,6-glucan (dextran) did not elicit any response (FIG. 1E), suggesting that the neutrophil response is specific to the β configuration. Elicitation of HSPs required heat-labile serum components, as pustulan-coated beads did not elicit HSPs when opsonized with heat-inactivated (HI) serum (FIG. 1D). Acetylated β-1,6-glucan elicited higher levels of HSPs than non-acetylated β-1,6-glucan (compare FIG. 1D to FIG. 1C, and to FIG. 2F), with β-1,6-glucan possessing greater stimulatory capability than β-1,3-glucan (FIG. 1C,D).

Example 2

Elicitation of HSPs by Pustulan is Due to β-1,6-glucan and O-acetylated β-1,6-glucan To confirm that elicitation by pustulan is due to β-1,6-glucan, the pustulan was digested with an endoglucanase specific for the β-1,6-glucan linkage [Lora, J. M. et al. *Mol Gen Genet* 247, 639-45].

Figure 2:
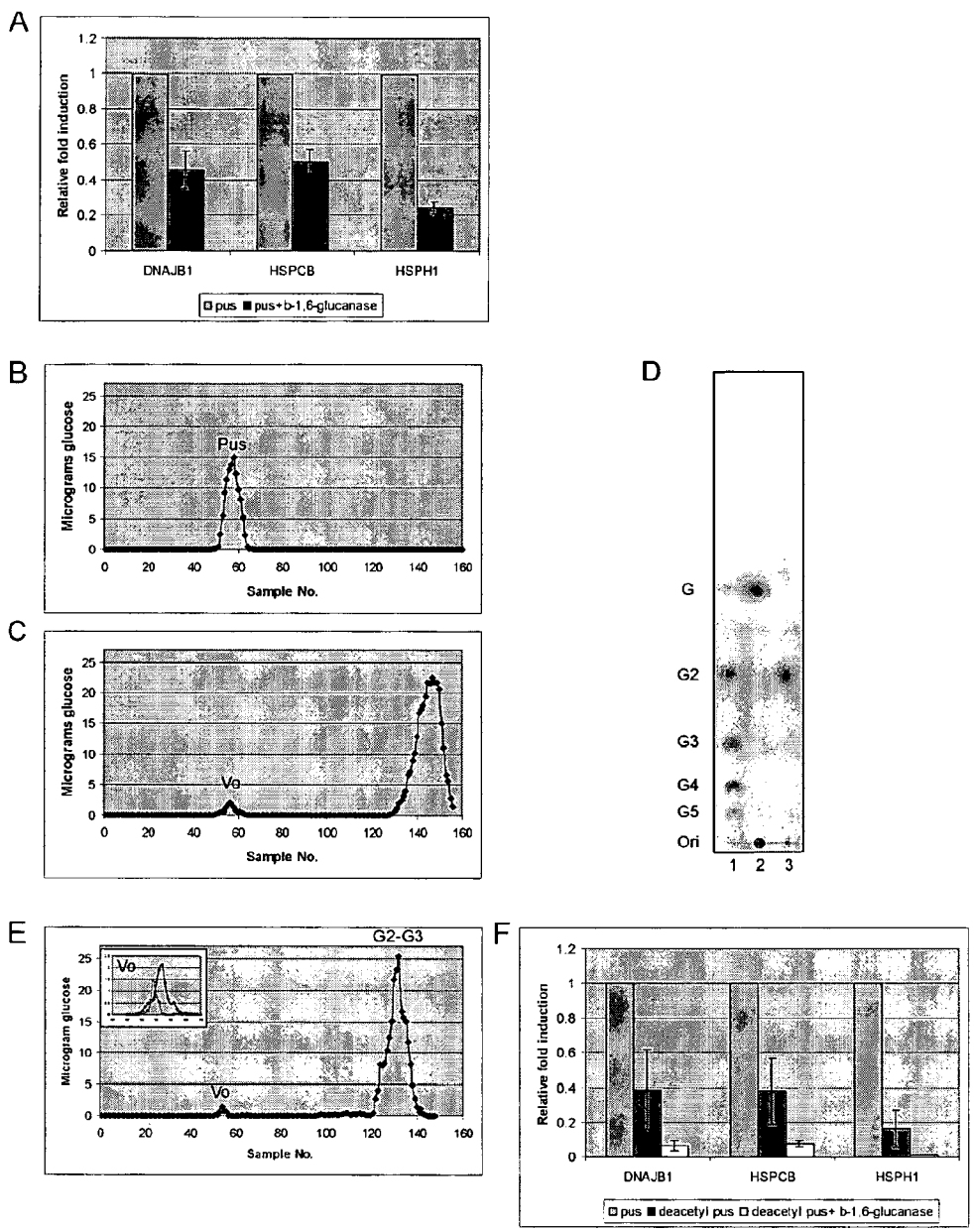
FIG. 2. Elicitation of HSPs by pustulan is due to β-1,6-glucan. Neutrophils were cultured with opsonized beads for 2 hours at 37° C. in A and F. (A) Endo-β-1,6-glucanase reduces the induction of HSPs by pustulan. Beads were coated with an equivalent amount of pustulan (pus) or endo-β-1,6-glucanase digested pustulan. Induction of HSPs with enzyme treated pustulan is relative to that with untreated. The data represent the average of several experiments with standard deviation. (B) Pustulan chromatographed on Biogel P6 column. (C) Pustulan digested first with endo-β-1,6-glucanase and run on a P6 column generated a large and a small peak. The small peak represents a tiny fraction of the original pustulan that was resistant to enzymatic digestion (Vo). (D) The large peak in C was shown by thin layer chromatography to be the expected degradation products, gentiobiose and gentiotriose. Lane 1 contains standard oligosaccharides (G to G5) as controls. Lane 2 is pustulan spiked with glucose (G). Lane 3 is endo-β-1,6-glucanase digested pus. Ori=origin. (E) Chromatography of deacetylated pustulan. The insert is an overlay of the Vo from C and E. (F) Deacetylation of pustulan followed by digestion with endo-β-1,6-glucanase eliminates induction of HSPs. Induction of HSPs in deacetylated pustulan or deacetylated pustulan digested with endo-β-1,6-glucanase is relative to that with untreated pustulan.

The digestion product resulted in ~80% reduction in elicitation of HSPs (FIG. 2A). Analysis of the digestion products of pustulan by P-6 size columns (see Methods) revealed a major peak of small products (FIG. 2 compare B to C), composed of di- and tri-saccharides as determined by TLC (G2-G3, compare lane 2 and 3, FIG. 2D). These short polymers in the G2-G3 fraction did not coat the beads efficiently.

In addition to the expected products of digestion by the β-1,6-glucanase, which constitute the vast majority of the pustulan, there was a small peak that was resistant to the enzyme (FIG. 2C, designated as Vo), corresponding to 4-5% of the starting material. The material in this peak was recognized by the anti-glucan antibody and elicited expression of the HSPs in the neutrophils. In order to determine whether the small peak resistant to enzymatic digestion was a modified form of the polymer, e.g. an acetylated form, the product was deacetylated.

Deacetylation of pustulan prior to fractionation virtually abolished this minor component (FIG. 2E) and rendered this residuum unable to elicit HSPs (FIG. 2F). These experiments show that the pustulan is a polymer of β-1,6-glucose containing a small amount of O-acetylated or otherwise O-modified β-1,6-glucan. The residual induction of HSPs by pustulan digested with the endo-β-1,6-glucanase may be attributed to O-acetylated pustulan that was resistant to the enzyme and coated the beads efficiently.

Example 3

β-1,6-glucan Mediates Efficient Phagocytosis and Production of Reactive Oxygen Species by Neutrophils Polybead polystyrene microspheres (beads) were coated with β-glucans and then opsonized. Phagocytosis of beads coated with laminarin (FIGS. 3A, a and b) or pustulan (FIGS. 3A, c and d) was assessed by time-lapse microscopy.

Figure 3:
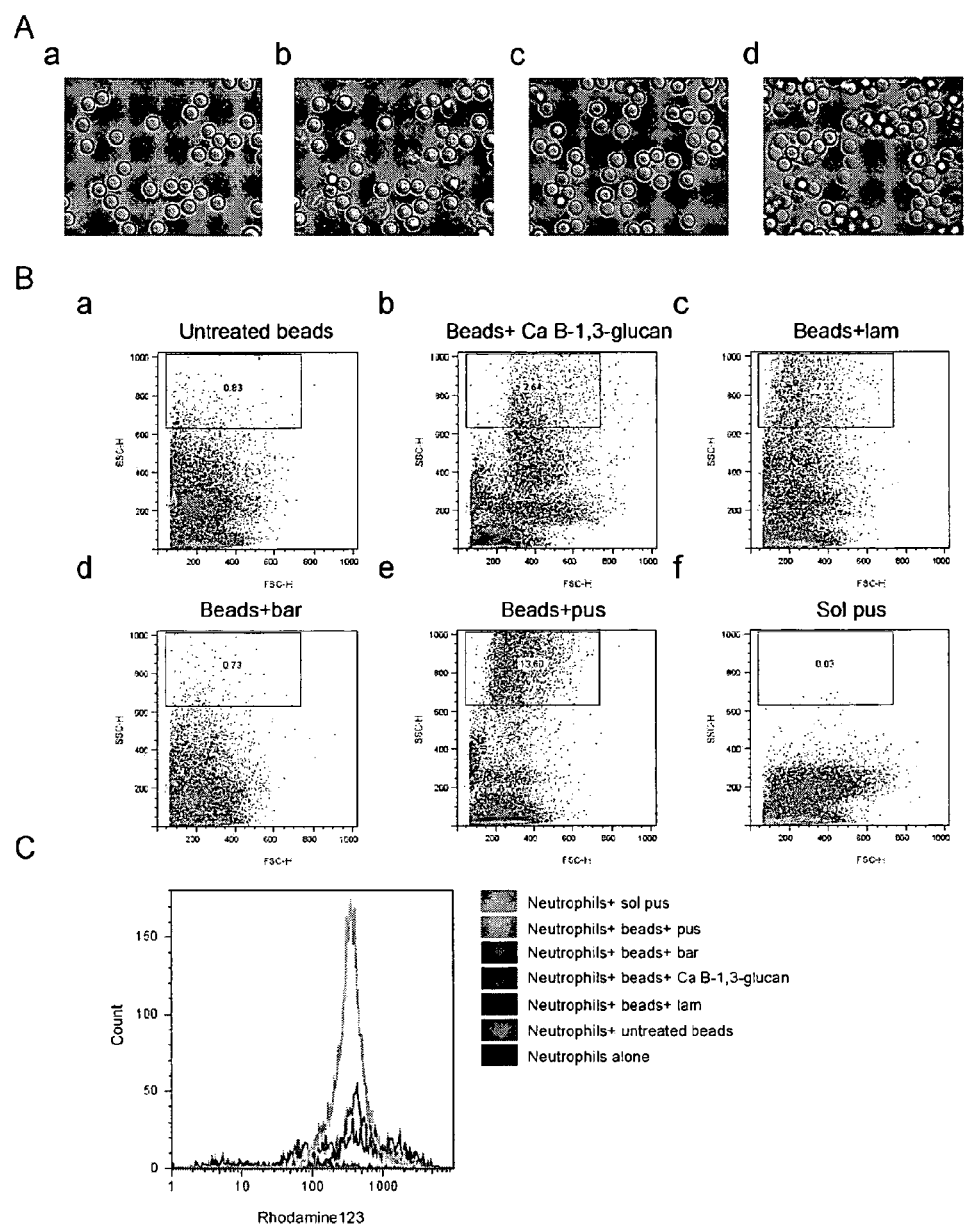
FIG. 3. β-1,6-glucan stimulates phagocytosis and production of reactive oxygen species (ROS) in neutrophils. Polybead polystyrene 6 μm microspheres (beads) were coated with an equivalent amount of the indicated β-glucans and then opsonized. (A) β-1,6-glucan stimulates phagocytosis. Phagocytosis was assessed by time-lapse microscopy for beads that were coated with laminarin (a, and b), or pustulan (c and d). The images at a and c were taken at time 0. Images b and d were taken after culturing with neutrophils for 40 minutes. (B) β-1,6-glucan stimulates phagocytosis. Phagocytosis was assessed by Fluorescence-Activated Cell Sorting (FACS) by the change in side scatter for neutrophils with (a)

Fluorescence-Activated Cell Sorting (FACS) analysis of neutrophils ingesting beads revealed that beads coated with pustulan were more efficiently internalized than beads coated with laminarin, although laminarin promoted internalization better than uncoated beads (FIG. 3B, compare panel e to c and a, respectively).

Since killing of pathogens by neutrophils depends on a burst of reactive oxygen species (ROS) [Babior, B. M. et al. J Clin Invest 52, 741-4], ROS induction by either of the two glucans was evaluated. ROS could not be detected in neutrophils alone or in neutrophils presented with beads that had not been treated (FIG. 3C, red and green, respectively). Low levels were detected with beads coated with laminarin, β-1, 3-glucan from *Candida albicans* or β-glucan from barley (FIG. 3C, blue, brown, and purple, respectively). However, beads coated with pustulan stimulated the generation of significant amounts of ROS (FIG. 3C, light blue). No ROS was detected by adding soluble pustulan (FIG. 3C, pink). These data show that β-1,6-glucan evokes a massive production of ROS, whereas the response to β-1,3-glucan is much lower by comparison.

Similarly, in FIG. 10, β-1,6-glucan is shown to be required for efficient phagocytosis of *Candida albicans*, production of ROS, and expression of HSPs, with samples subjected to β-1,6-glucanase digestion showing reduced efficacy.

Example 4

Complement Deposition on Beads Coated with β-1,6-glucan

As serum is required for phagocytosis and the induction of HSPs by beads coated with β-1,6-glucan (FIG. 1D), it was of interest to determine whether there was a serum component that was differentially deposited on beads coated with β-1,6-glucan or β-1,3-glucan. Beads were coated with laminarin or pustulan and opsonized. Bound proteins were removed from beads and separated by SDS gel electrophoresis. Although a number of serum proteins bound both β-1,3-glucan or β-1,6-glucan, there were two prominent proteins that adhered more avidly to β-1,6-glucan (FIG. 4A). These proteins were extracted from the gel and subjected to analysis by mass spectrometry. The peptides from these bands gave masses that identified both proteins as C3, suggesting that proteolytic fragments of C3 are deposited more avidly on β-1,6-glucan than β-1,3-glucan.

Western analysis revealed that indeed β-1,6-glucan was deposited with more C3 (FIG. 4B). Antibodies specific for the alpha chain detected high molecular weight bands, including bands the size of the complete C3 or C3b (105 and 115 kDa, respectively), as well as a lower molecular doublet the size of C3d (31 and 33 kDa, FIG. 4B a). Beads coated with laminarin had low levels of these C3 fragments (FIG. 4B a). Antibodies specific for the C3 beta chain revealed only the high molecular weight C3/C3b (FIG. 4B b). The 75 kDa chain of C3b or iC3b were not detected (FIG. 4B b).

Example 5

Additional Complement Deposition Studies

To assess further the differences in C3 deposition on β-1, 6-glucan as compared with β-1,3-glucan, serum was preincubated with soluble pustulan or laminarin before using it to opsonize beads coated with pustulan. Preincubation of the serum with soluble pustulan eliminated phagocytosis (FIG. 5A compare c and a) and ROS production (FIG. 5B compare red and blue) by neutrophils, suggesting that serum C3 was titrated out by the soluble β-1,6-glucan. Serum that was preincubated with an equivalent amount of soluble laminarin still mediated phagocytosis (FIG. 5A compare b and a) and ROS production (FIG. 5B compare red and green), suggesting that β-1,3-glucan did not efficiently block the interaction of C3 with beads coated with pustulan.

Western analysis revealed that preincubation with soluble pustulan eliminated most of the C3/C3b and C3d deposition on the pustulan-coated beads (FIG. 5C compare 1 to 3). Preincubation with laminarin eliminated the low molecular weight C3d doublet, but retained the high molecular weight C3/C3b (FIG. 5C compare 2 to 3), suggesting that the remaining C3/C3b was mediating phagocytosis and induction of ROS (FIGS. 5A and B). Preincubation of serum with soluble pustulan reduced *Candida* killing (FIG. 5D).

Example 6

Role of CR3 in Phagocytosis

Complement receptor 3 (CR3) is known to mediate phagocytosis of opsonized yeast and the yeast cell wall preparation zymosan, as well as ROS production, thus CR3 mediated phagocytosis of beads coated with β-1,6-glucan. Anti-human CR3 blocking antibodies reduced the extent of phagocytosis (FIG. 6A compare b to a) and ROS production (FIG. 6B compare red to green), suggesting that CR3 recognized C3b proteolytic fragments (C3d) that are deposited on particulate β-1,6-glucan.

Example 7

β-1,6-glucan Elicits Chemokines in Monocytes

To assess the role of β-1,6-glucans in eliciting chemokines in monocytes, polybead polystyrene microspheres (beads) were coated with equivalent amounts of the β-1,3-glucan laminarin (lam), or the β-1,6-glucan pustulan (pus). Beads were opsonized with pooled human serum. Monocytes were cultured for 2 hours with 5 mg/ml of soluble lam or pus, or with the beads described above. Induction of chemokines was determined by quantitative real-time PCR. Results were averaged and standard deviations were calculated (FIG. 7).

Example 8

β-1,6-glucan Conjugates

In order to determine whether the activity of neutrophils may be enhanced, physical linkage of the polysaccharide to targeting agents such as monoclonal antibodies with appropriate specificity was pursued.

Under such a scenario, deposition of complement on the β-1,6-glucan polysaccharide is expected to recruit neutrophils and enhance engulfment of the whole complex (FIG. 8). Some antibodies are specifically known to bind complement poorly (for example IgG2 and IgG4). The differential ability of human IgG1 and IgG4 to activate complement is determined by the COOH-terminal sequence of the CH2 domain, and this technology would enhance their efficacy.

The linkage between polysaccharide and antibody can be accomplished via any number of means, including protocols described for linking polysaccharides to proteins [e.g. Bystricky S, et al. Glycoconj J. 2000 October; 17 (10):677-80; and Tianhong Chen, et al. Langmuir 2003, 19, 9382-9386]. Another means of such linkage comprises modifying the reducing end of the polysaccharide to comprise an amino group as described [Xia B, et al. Nat Methods. 2005 November; 2(11):845-50; Valdivia A, et al. J Biotechnol. 2006 Apr.

10; 122(3):326-33]. The amino group could then be coupled to the carboxyl terminus of the antibody.

Toward this end, pustulan (a 20 KDa β-1,6-glucan polysaccharide, which has 10-20% O-acetyl groups) was linked to an anti-*Candida albicans* monoclonal antibody following previous methods for linking mannan to BSA [Bystricky S, et al. Glycoconj J. 2000 October; 17 (10):677-80]. The product was dialyzed against water, and complexes larger than 100 kDa were isolated using the appropriate cutoff columns (FIG. 9A). A fraction was isolated that was larger than 100 kDa and exhibited characteristic bands of the antibody and a smear indicative of the presence of the polysaccharide, indicating the two were in the same fraction. Since the molecular weight of the polysaccharide is 20 Kda, this suggests that the polysaccharide and the antibody were linked together.

Sugar quantification was accomplished using a described phenol-sulfuric acid method [Duboius, M., Gilles, K. A., Hamilton, J. K., Rebers, P. A., and Smith, F. (1956). Anal Biochem 28, 350-356]. The presence of polysaccharide in the fraction larger than 100 kDa was thereby confirmed.

The effect of the modified antibody on the production of ROS by neutrophils cultured with *Candida albicans* was assessed. Neutrophils cultured with *Candida albicans* in the presence of the untreated antibody produced low levels of ROS (FIG. 9B). Antibody covalently bound to the polysaccharide, however, elicited high ROS production by neutrophils. Mixing untreated antibody with the polysaccharide without covalently attaching them did not produce a comparable effect, indicating that the polysaccharide must be bound to the antibody to elicit ROS production.

Example 9

In Vivo Protection Medicated by β-1,6-glucan

Since complement activation was mediated by β-1,6-glucan in vitro, it was of interest to determine whether such protective responses could be elicited in vivo, in mouse models. Toward this end, it was first determined whether murine serum activates complement (FIG. 11). Beads coated with pustulan (β-1,6-glucan) and opsonized with murine serum showed complement activation, as compared to those coated with laminarin (β-1,3-glucan). Mice injected with *Candida albicans* cells ($10^6$) iv, followed by injection of $10^5$ β-1,6-glucan-coated beads or untreated beads were evaluated for survival, with treated mice demonstrated significantly prolonged survival as compared to untreated mice.

PLGA beads encapsulating β-1,6-glucan elicited production of reactive oxygen species and protected mice from systemic fungal infection (FIG. 12). PLGA beads encapsulating β-1,6-glucan elicited higher levels of reactive oxygen species (Panel B) and markedly enhanced survival (panel C) as compared to PLGA beads encapsulating β-1,3-glucan.

Example 10

β-1,6-glucan Mediated Immunoglobulin Deposition

Since complement activation was mediated by β-1,6-glucan in vitro, it was of interest to determine whether immunoglobulin deposition was elicited as well. Toward this end, beads treated with pustulan (β-1,6-glucan) and laminarin (β-1,3-glucan), as well as untreated beads were opsonized and evaluated for IgM and IgG deposition (FIG. 13).

Markedly enhanced IgG deposition occurred on pustulan treated beads, as compared to laminarin or untreated beads.

Example 11

An Embodiment of the Production of PLGA Microparticles Containing β-1,6-glucan

The solvent evaporation encapsulation method is commonly used to make biodegradable polymer microparticles of polymers such as PLGA and PLA because these poly acids are highly biocompatible and have favorable biodegradation kinetics. Solvent evaporation encapsulation involves several steps and common variations:

1) The polymer is dissolved in a water-immiscible solvent
2) The medicament is dissolved, dispersed or emulsified in the polymeric solution
3) The resultant solution, dispersion or emulsion is then emulsified in a continuous aqueous phase forming discrete droplets
4) The water-immiscible solvent diffuses though the water phase and evaporates at the water-air interface inducing precipitation of the polymer and encapsulation of the medicament The solvent must be immiscible with water and be a suitable solvent for the medicament, or be immiscible with another solvent which is a suitable solvent for the medicament such that a primary emulsion of polymer and drug can be made, or there must be another method of dispersing the medicament in the polymer solution.

Solubility of β-1,6-glucan in Candidate Solvents

The solubility of β-1,6-glucan was determined in a number of solvents potentially useful in multiple solvent microemulsion protocols by adding ~10 mg/mL of solid β-1,6-glucan to the solvents at room temperature and observing degree of dissolution. Water miscible solvents include water, DMSO, methanol and ethanol. Water-immiscible solvents include acetone, methylene chloride and ethyl acetate. β-1,6-glucan demonstrated solubility>10 mg/mL in only DMSO, but was soluble at lower concentrations in water.

Generation of β-1,6-glucan Encapsulating Microparticles with Standard Protocols

Using a standard protocol for a W/O/W emulsion, β-1,6-glucan was encapsulated using water as the inner phase, methylene chloride as the oil phase and water as the outer phase. Concentrations of 25 mg/mL in the inner aqueous phase were achieved by first dissolving β-1,6-glucan in DMSO and then adding to water. The resulting particles (labeled 2%) were tested on neturophils and did not demonstrate activity.

Generation of β-1,6-glucan Encapsulating Nanoparticles with Nano-Precipitation

Nanoprecipitation is a simple method which is useful for making polymer nanoparticles which entrap drug. Nanoprecipitation techniques typically include the following steps:

1.) Dissolution of the polymer and drug in a solvent
2.) Slow addition under vigorous mixing of this polymer/drug solution to a non-solvent. The non-solvent should be miscible with the solvent, but the polymer and the drug should not be soluble in the non-solvent Since β-1,6 glucan and PLGA are highly soluble in DMSO and non-soluble in water, nanoparticles over a range of glucan/PLGA ratios should be possible. The following conditions were tested:

| β-1,6-glucan | PLGA | Size (nm) |
|---|---|---|
| 90% | 10% | 35,650 |
| 80% | 20% | 124 |
| 50% | 50% | 199 |
| 25% | 75% | 206 |
| 10% | 90% | 194 |
| 0% | 100% | 201 |

At concentrations above 80% β-1,6-glucan particles would no longer form. The resulting particles were tested on neutrophils and did not demonstrate activity.

Development of β-1,6-glucan Nanosuspension-Emulsion Protocol: Modification of Standard W/O/W Protocol Generation of β-1,6-glucan Nanosuspension β-1,6-glucan was dissolved in dimethyl sulfoxide at room temperature (50 mg/mL) and diluted with an equal volume of deionized water. This mixture was added to a solution of PLGA in dichloromethane under sonication with a probe sonicator.

The DMSO/water/glucan solution was miscible with the PLGA/Dichloromethane solution and formed a single phase. When DMSO/water/glucan solution was injected into dichloromethane under stirring (not sonication) precipitation of the β-1,6-glucan occurred and the precipitate formed a stringy gel (during nanoprecipitation procedure). Under sonication the precipitation appeared to generate a cloudy solution which was likely a nano suspension or emulsion which was suspended in a secondary external emulsion.

The suspension generated above was added to a solution of 1% polyvinyl alcohol in water and homonogized to generate polymer microparticles. Evaporation of dichloromethane proceeded during 3 hours of stirring at atmospheric conditions.

The resulting particles were washed 3 times with deionozed water and lyophilized to give a dry powder.

Example 12

β-1,6-glucan Conjugates can Improve Efficacy of Monoclonal Antibodies

Some monoclonal antibodies (mAb) have good affinity to their target, but do not elicit a good immune response. Some mAb could become more efficacious if they had better complement-fixing properties. In some embodiments of this invention the above-described limitations in mAb use are addressed in term of changes in effect of conjugating β-1,6-glucan to mAb, for example on their complement-dependent cytotoxicity (CDC) properties.

The β-1,6-glucan polysaccharide is conjugated directly to an Fc portion of a mAb, for example by oxidation of the polysaccharide and/or antibody with sodium meta-periodate. Various diamine linkers, including PEG diamines, as well as biotin-avidin/streptavidin-based conjugation, are tested. Conjugates are monitored to ensure that they retain specificity to the target, retain complement-fixing properties of the polysaccharide, and are soluble.

Conjugates may comprise, for example, an anti-*Candida* mAb, or other mAb directed against cell wall structures such as different mannans and glucans are tested.

β-1,6-glucan is conjugated to a set of syngeneic monoclonal antibodies having the same specificity to a target cell (same Fab region), but different conserved regions (Fc) which have different complement-fixing properties. The polysaccharide is conjugated to IgG2a and IgG2b, and the capacity of these antibodies to carry out CDC and/or ADCC in vitro is tested using dyes that are excluded by live cells (such as propidium iodide) or by radio isotopes that are released by dead cells (such as 51-chromium, ToxiLight, which detects adenylate kinase, etc.).

The polysaccharide-conjugated antibodies are compared to the respective unconjugated antibodies (mixed with the polysaccharide without covalent binding), or the syngeneic IgG1, for increased CDC. Antibodies showing enhanced CDC in association with the conjugated polysaccharide are tested in vivo in a model for these cells. Mice are injected with the target cells followed by the unconjugated antibodies, the conjugated antibodies, or isotype control antibodies and monitored for survival.

Conjugation of the polysaccharides to FDA-approved mAb (including Alemtuzumab (Campath), Bevacizumab (Avastin), Cetuximab (Erbitux), Gemtuzumab (Mylotarg), Ibritumomab (Zevalin), Panitumumab (Vectibix), Rituximab (Rituxan), Tositumomab (Bexxar), Trastuzumab (Herceptin), Palivizumab (Synagis)) are tested, as well, for increased mAb efficacy. Other mAb which may be tested may comprise such mAB, which have been shown to lack adequate immune stimulation in clinical trials in protection studies, whose immune stimulatory capacity may be enhanced by their conjugation to the glucans of this invention.

Example 13

β-1,6-glucan Conjugates for Cancer Treatment

Breast cancer is the second leading cause of cancer death among women in the western world and the leading cause of death among women between the ages of 30 and 70. The highest mortality is restricted to patients whose regional lymph nodes are involved. Early detection, followed by surgery, provides good prognosis. In patients with occult lymph node metastasis, adjuvant chemotherapy or hormonal therapy for breast cancer have proven to be effective, yet may patients will succumb to metastasis.

A number of tumor-associated antigens have been described for breast carcinomas. The MUC-1 mucin, a high molecular weight glycoprotein, is highly expressed on breast carconimas. BA-46 is a transmembrane-associated glycoprotein of the human milk fat globule membrane (HMFG) that is overexpressed in human breast carcinomas. Anti-BA-46 radio-conjugated monoclonal antibodies have successfully targeted human breast tumors transplanted into mice.

The effect of conjugating β-1,6-glucan to MUC-1 and BA-46-derived peptides on their ability to induce CTL which preferentially recognize breast tumor-derived peptides is tested.

The β-1,6-glucan polysaccharide is conjugated directly to the MUC-1 and BA-46-derived peptides. Conjugates are monitored to ensure that they retain specificity to the target, retain complement-fixing properties of the polysaccharide, and are soluble.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A composition comprising β-1-6-glucan linked to a targeting moiety that targets a neoplastic cell, a pre-neoplastic cell or a component thereof wherein said targeting moiety is an antibody or antigen-binding fragment thereof.

2. The composition of claim 1, wherein said β-1-6-glucan is isolated or derived from a lichen, a fungus, or a yeast.

3. The composition of claim 1, wherein said β-1-6-glucan is genetically engineered, or chemically synthesized or acetylated.

4. The composition of claim 1, wherein the composition is a pharmaceutical composition, a food or food product, a food supplement, or a cosmetic composition.

5. A composition comprising β-1-6-glucan linked to an antibody or antigen-binding fragment thereof.

6. The composition of claim 1, wherein said targeting moiety is a monoclonal antibody or a human antibody.

7. The composition of claim 1, wherein said targeting moiety is a humanized antibody.

8. The composition of claim 1, wherein said targeting moiety is selected from the group consisting of Alemtuzumab, Bevacizumab, Cetuximab, Gemtuzumab, Ibritumomab, Panitumumab, Rituximab, Tositumomab, Trastuzumab, and Palivizumab.

9. The composition of claim 1, wherein said targeting moiety is a Fab fragment, Fab' fragment, (Fab')$_2$ fragment, Fv fragment, a single chain antibody or a peptide coding for a single complementarity-determining region.

10. A composition comprising β-1-6-glucan linked to a targeting moiety that binds to a tumor antigen wherein said targeting moiety is an antibody or antigen-binding fragment thereof.

11. The composition of claim 1, wherein said targeting moiety is linked to said β-1-6-glucan via a covalent linkage.

12. The composition of claim 1, wherein said targeting moiety is linked to said β-1-6-glucan via a non-covalent linkage.

13. The composition of claim 1, wherein said targeting moiety is linked to said β-1-6-glucan via a linker molecule.

14. The composition of claim 1, wherein the composition is substantially free of β-1-3-glucan.

15. The composition of claim 1, wherein at least 90% of the dry weight of glucan contained in the composition is β-1-6-glucan.

16. The composition of claim 1, wherein said β-1-6-glucan is processed.

17. The composition of claim 1, wherein said β-1-6-glucan is isolated or derived from Umbilicariaceae.

18. The composition of claim 1, wherein said targeting moiety is an antibody or antigen-binding fragment thereof that is linked to said β-1-6-glucan via a covalent linkage.

19. The composition of claim 1, wherein the composition promotes complement-mediated lysis of the neoplastic or pre-neoplastic cell when contacted in vitro with the neoplastic cell or pre-neoplastic cell in the presence of serum.

20. The composition of claim 1, wherein the composition promotes deposition of C3 or a C3 proteolytic fragment when contacted in vitro with the neoplastic cell or pre-neoplastic cell in the presence of serum.

21. The composition of claim 20, wherein the C3 proteolytic fragment is selected from the group consisting of C3b, C3d and a combination thereof.

22. The composition of claim 1, wherein the composition promotes deposition of IgG when contacted in vitro with the neoplastic cell or pre-neoplastic cell in the presence of serum.

23. The composition of claim 1, wherein the composition promotes recruitment of neutrophils when contacted in vitro with the neoplastic cell or pre-neoplastic cell in the presence of serum and neutrophils.

24. The composition of claim 5, wherein the composition promotes complement-mediated lysis of a cell that is targeted by the antibody or antigen-binding fragment thereof when contacted in vitro with the cell in the presence of serum.

25. The composition of claim 5, wherein the composition promotes deposition of C3 or a C3 proteolytic fragment when contacted in vitro, in the presence of serum, with a cell that is targeted by the antibody or antigen-binding fragment thereof.

26. The composition of claim 25, wherein the C3 proteolytic fragment is selected from the group consisting of C3b, C3d and a combination thereof.

27. The composition of claim 5, wherein the composition promotes deposition of IgG when contacted in vitro, in the presence of serum, with a cell that is targeted by the antibody or antigen-binding fragment thereof.

28. The composition of claim 5, wherein the composition promotes recruitment of neutrophils when contacted in vitro, in the presence of serum and neutrophils, with a cell that is targeted by the antibody or antigen-binding fragment thereof.

29. The composition of claim 10, wherein the composition promotes complement-mediated lysis of a cell that expresses the tumor antigen when contacted in vitro with the cell in the presence of serum.

30. The composition of claim 10, wherein the composition promotes deposition of C3 or a C3 proteolytic fragment when contacted in vitro, in the presence of serum and neutrophils, with a cell that expresses the tumor antigen.

31. The composition of claim 30, wherein the C3 proteolytic fragment is selected from the group consisting of C3b, C3d and a combination thereof.

32. The composition of claim 10, wherein the composition promotes deposition of IgG when contacted in vitro, in the presence of serum, with a cell that expresses the tumor antigen.

33. The composition of claim 10, wherein the composition promotes recruitment of neutrophils when contacted in vitro, in the presence of serum, with a cell that expresses the tumor antigen.

34. The composition of claim 1, wherein less than 10% of the total glucan in the composition, by weight, is β-1-3-glucan.

35. The composition of claim 5, wherein less than 10% of the total glucan in the composition, by weight, is β-1-3-glucan.

36. The composition of claim 5, wherein the composition is substantially free of β-1-3-glucan.

37. The composition of claim 5, wherein at least 90% of the dry weight of glucan contained in the composition is β-1-6-glucan.

38. The composition of claim 10, wherein less than 10% of the total glucan in the composition, by weight, is β-1-3-glucan.

39. The composition of claim 10, wherein the composition is substantially free of β-1-3-glucan.

40. The composition of claim 10, wherein at least 90% of the dry weight of glucan contained in the composition is β-1-6-glucan.

41. The composition of claim 5, wherein said antibody is a monoclonal antibody or a human antibody.

42. The composition of claim 5, wherein said antibody is a humanized antibody.

43. The composition of claim 5, wherein said antibody is selected from the group consisting of Alemtuzumab, Bevacizumab, Cetuximab, Gemtuzumab, Ibritumomab, Panitumumab, Rituximab, Tositumomab, Trastuzumab, and Palivizumab.

44. The composition of claim 5, wherein said antibody or antigen-binding fragment thereof is linked to said β-1-6-glucan via a covalent linkage.

45. The composition of claim 10, wherein said antibody or antigen-binding fragment thereof is linked to said β-1-6-glucan via a covalent linkage.

\* \* \* \* \*

UNITED STATES PATENT AND TRADEMARK OFFICE
CERTIFICATE OF CORRECTION

| | | |
|---|---|---|
| PATENT NO. | : 8,580,253 B2 | Page 1 of 1 |
| APPLICATION NO. | : 12/513830 | |
| DATED | : November 12, 2013 | |
| INVENTOR(S) | : Rubin-Bejerano et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 955 days.

Signed and Sealed this
Thirty-first Day of March, 2015

Michelle K. Lee
*Director of the United States Patent and Trademark Office*